US011905287B2

(12) United States Patent
Gallagher et al.

(10) Patent No.: US 11,905,287 B2
(45) Date of Patent: *Feb. 20, 2024

(54) 4-SUBSTITUED CYTISINE ANALOGUES

(71) Applicant: The University of Bristol, Bristol (GB)

(72) Inventors: Timothy Charles Gallagher, Bristol (GB); Hugo Rego Campello, Bristol (GB)

(73) Assignee: THE UNIVERSITY OF BRISTOL (GB)

(*) Notice: Subject to any disclaimer, the term of this patent is extended or adjusted under 35 U.S.C. 154(b) by 0 days.

This patent is subject to a terminal disclaimer.

(21) Appl. No.: 18/178,176

(22) Filed: Mar. 3, 2023

(65) Prior Publication Data
US 2023/0203038 A1    Jun. 29, 2023

Related U.S. Application Data

(63) Continuation of application No. 16/326,615, filed as application No. PCT/GB2017/052438 on Aug. 17, 2017, now Pat. No. 11,667,638.

(30) Foreign Application Priority Data

Aug. 19, 2016  (GB) .................................... 1614235
Jun. 16, 2017  (GB) .................................... 1709642

(51) Int. Cl.
*C07D 471/18*  (2006.01)
*B01J 31/18*  (2006.01)
*B01J 31/24*  (2006.01)

(52) U.S. Cl.
CPC ......... *C07D 471/18* (2013.01); *B01J 31/1815* (2013.01); *B01J 31/1825* (2013.01); *B01J 31/2409* (2013.01)

(58) Field of Classification Search
None
See application file for complete search history.

(56) References Cited

U.S. PATENT DOCUMENTS

| 5,242,916 | A | 9/1993 | Lippiello et al. |
| 11,667,638 | B2* | 6/2023 | Gallagher ............ C07D 471/18 514/233.2 |
| 2013/0005689 | A1 | 1/2013 | Cannizzaro et al. |
| 2016/0199315 | A1 | 7/2016 | Takagi et al. |

FOREIGN PATENT DOCUMENTS

| CN | 102639530 A | 8/2012 |
| CN | 103509021 | 8/2016 |
| EP | 1586320 | 10/2005 |
| JP | 2000505809 A | 5/2000 |
| JP | 2014520809 A | 8/2014 |
| WO | WO 98/18798 | 5/1998 |
| WO | WO 2005/000806 | 1/2005 |
| WO | WO 2007/100430 | 9/2007 |
| WO | WO 2007/115092 | 10/2007 |
| WO | WO 2008/011484 | 1/2008 |
| WO | WO 2014/001348 | 1/2014 |

OTHER PUBLICATIONS

Chellappan, S.K., et al., "Synthesis and Pharmacological Evaluation of Novel 9- and 10-Substituted Cytisine Derivatives—Nicotinic Ligands of Enhanced subtype Selectivity," Journal of Medicinal Chemistry 49(9):2673-2676, May 2006. (Author Manuscript provided, PMCID: PMC2504867, available in PMC Aug. 11, 2008, 15 pages.).
Durkin, P., et al., "Lactam Enolate-Pyridone Addition: Synthesis of 4-Halocytisines," Synlett 18:2789-2791, 2010.
International Preliminary Report on Patentability dated Feb. 19, 2019, issued in corresponding International Application No. PCT/GB2017/052438, filed Aug. 17, 2017, 11 pages.
International Search Report and Written Opinion dated Apr. 18, 2018, issued in corresponding International Application No. PCT/GB2017/052438, filed Aug. 17, 2017, 18 pages.
Kozikowski, A.P., et al., "Chemical Medicine: Novel 10-Substituted Cytisine Derivatives with Increased Selectivity for α4β2 Nicotinic Acetylcholine Receptors," ChemMedChem 2:1157-1161, 2007.
Miura, W., et al., "Iridium-Catalyzed Site-Selective C—H Borylation of 2-Pyridones," Synthesis 49:4745-4752, 2017.
Search Report dated May 18, 2018, issued in GB Application 1713217.6, filed Aug. 17, 2017, 5 pages.

* cited by examiner

*Primary Examiner* — Joseph R Kosack
(74) *Attorney, Agent, or Firm* — Perkins Coie LLP

(57) ABSTRACT

Disclosed are novel analogs of cytisine, a process for their preparation, pharmaceutical compositions containing them, and their use in the prevention of or treatment of CNS disorders including addictive disorders.

17 Claims, No Drawings

4-SUBSTITUED CYTISINE ANALOGUES

RELATED APPLICATIONS

This application is a continuation of U.S. patent application Ser. No. 16/326,615, filed on Feb. 19, 2019, which is a 35 USC § 371 National Stage application of International Application No. PCT/GB2017/052438, filed on Aug. 17, 2017, which claims the benefit of United Kingdom Patent Application Nos. 1709642.1, filed on Jun. 16, 2017 and 1614235.8, filed on Aug. 19, 2016, the disclosure of which are incorporated herein by reference in their entireties.

TECHNICAL FIELD

The present invention relates to novel analogs of cytisine, and their use in medicine, for example in the treatment of addiction. The present invention also provides improved synthetic routes for the preparation of analogs of cytisine.

BACKGROUND

Nicotinic acetylcholine receptors (nAChRs) are ligand-gated ion channels that are expressed in various parts of the brain and elsewhere in the central nervous system of humans. nAChRs are involved in a range of physiological functions, such as cognitive function, learning and memory, sleep, anxiety, arousal, reward, motor control and other neural functions. nAChRs have also been implicated in a number of pathological conditions such as Parkinson's disease, Alzheimer's disease, depression, epilepsy, autism and schizophrenia. nAChRs have also been implicated in addiction and dependence to a range of substances, for example nicotine addiction (Schalling and Waller, Acta Physiologica Scandinavica. Supplementum, 1980, volume 479, pages 53-56), alcohol addiction (Holgate et al., Brain Science, 2015, September 5(3), pages 258-274), drug dependence (Rahman et al., Frontiers in Neuroscience, 2014, volume 8, article 426).

Numerous subtypes of nAChRs are known to exist. Muscle-type nicotinic receptors (located in the neuromuscular junction) are known to be formed by five different substructures, named α, β, γ, δ, plus the recently discovered additional subunit E.

Neuronal-type nAChRs (located in the CNS, the peripheral ganglia, and the adrenal medulla) display only two classes of subunits, named as α2-α9 and β2-β4, which can assemble into homomeric or heteromeric combinations. Although a large number of neuronal subtypes have been identified, the heteromeric combinations (α4)₃(β2)₂, α3β4 and the homomeric α7 appear to play prominent roles in the brain. Among them, the heteromeric combination α4β2 is the predominant subtype in the CNS, accounting for approximately 90% of the receptors and binding ACh with high affinity. α7 homomeric combination is the other major subtype, binding ACh with low affinity.

The heteromeric combination α4β2 can be assembled into two different stoichiometries: (α4)₂(β2)₃ and (α4)₃(β2)₂, commonly referred as A2B3 and A3B2 respectively. The main α4β2 subtype is proposed to have a structure A2B3, being formed by two α4 and three β2 subunits; and it is the main subtype involved in addiction.

Nicotine is believed to activate this α4β2 receptor subtype, and thereby increasing the release of dopamine in the nucleus accumbens and prefrontal cortex, specific parts of the human brain which have been linked to drug-dependency.

Additionally, the α4β2 receptor subtype has also been implicated in alcohol dependency (Mitchell et al., Pyschopharmacology, October 2012, 223, 3, pages 299 to 306) and drug addiction (Crunelle et al., European Neuropsychopharmacology, February 2010, 20, 2, pages 69 to 79).

Compounds with the ability to modulate nAChRs have been found to be effective in treating conditions associated with those receptors. For example, studies suggest that transdermally administered nicotine may be able to improve cognitive function in people suffering from age associated memory impairment (see, for example, White et al., Psychopharmacology, February 2004, 171, 4, pages 465 to 471). However, there are certain disadvantages to the use of nicotine, even when administered transdermally. For example, it is known to be addictive and, in the 2014 US Surgeon General's report, it was stated that nicotine negatively affects pregnancy outcomes and fetal brain development.

In the field of smoking cessation therapy, nicotine has been used to assist smokers give up smoking, and products to deliver nicotine via oral routes (e.g. tablets or chewing gum) or transdermally have been developed and are well known.

Alternative compounds which modulate nAChRs have also found use in the treatment of addictions. Varenicline has been commercialised under the brand name Chantix® in the US and Champix® in Europe by Pfizer and is approved for use in smoking cessation therapy. Additionally, the drug has been trialed in the treatment of alcohol and drug dependence (Mitchell et al., Pyschopharmacology, October 2012, 223, 3, pages 299 to 306, and Crunelle et al., European Neuropsychopharmacology, February 2010, 20, 2, pages 69 to 79).

Mihalak et al. (Molecular Pharmacology, 2006, September, 70(3), pages 801 to 805) found that varenicline is a partial agonist at α4β2 receptors, is a low potency agonist at α3β4 receptors, is a partial agonist at α3β2 and α6 receptors, and is a potent agonist at α7 receptors.

A further drug used in smoking cessation therapy is cytisine. Cytisine is a naturally occurring, pyridone-containing alkaloid known to be a partial agonist of nAChRs. Pharmacologically, cytisine shows a high degree of similarity to nicotine and has already been used successfully as a smoking cessation aid for many years. The chemical structure of cytisine (or more specifically, the (−) enantiomer of cytisine) is shown below:

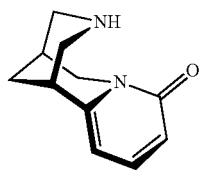

While cytisine is a safe and efficacious therapy for smoking cessation, there have been attempts to produce functionalised derivatives of that compound.

Conventionally, several different numbering systems for cytisine have been used. For the purposes of this discussion, and the disclosure of the present invention, the following numbering system will be used:

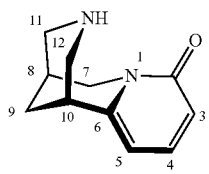

Kozikowski et al., in two papers (Journal of Medicinal Chemistry, 2006, 49, pages 2673 to 2676 and ChemMedChem, 2007, 2, pages 1157 to 1161) summarised work conducted previously on the introduction of substituents on the cytisine structure (principally at the 3- and 5-positions), as well as disclosing the synthesis of reportedly novel racemic analogues, including substituents at the 3-, 4- or 7-positions.

In the 2006 paper by Kozikowski et al., racemic 4-substituted compounds were reported as not showing agonist activity at the α4β2 receptor subtype, despite high selectivity for this subtype. The results presented in the 2006 paper indicated that 4-substituted analogs of cytisine are weak antagonists of α4β2 receptor subtype.

Thus, the work done by Kozikowski et al. indicated that the activity of 4-substituted cytisine analogs was significantly different to the known addiction therapies cytisine and varenicline.

More recently, work by other teams has focused on substitutions at other positions on the cytisine structure. For example, in International Patent Publication No. WO2014/001348, analogs of cytisine having the general structure shown below were synthesised:

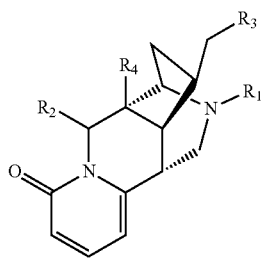

Additionally, in Chinese Patent Publication No. 103509021, cytisine analogs including substituents at the 5-position and/or at the nitrogen atom on the piperidine ring.

Rouden et al., (Chemical Reviews, 2014, 114, pages 712 to 778) have prepared a comprehensive review of all of the different research into functionalised derivatives of cytisine.

Despite the substantial investigations into cytisine analogs, and their potential to provide pharmaceutical agents with improved properties as compared to cytisine and/or other nAChR binding drugs, no such compound, to the inventors' knowledge, has been brought forward into clinical trials, let alone approved as pharmaceutical products. Thus, there remains a need for pharmaceutical agents having improved properties as compared to cytisine, for example improved safety and/or efficacy as medicinal agents, for example in the treatment of addiction.

Thus, according to a first aspect of the present invention, there is provided a compound of formula (I):

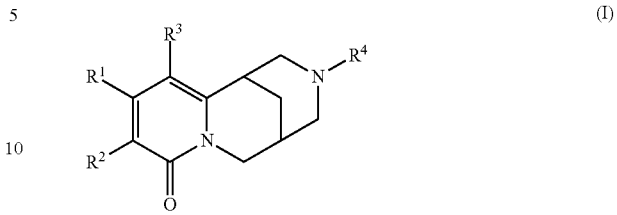

or a pharmaceutically acceptable salt, solvate and/or ester thereof, wherein $R^1$ to $R^4$ are as defined below. The invention also provides pharmaceutical compositions comprising such compounds, as well as the use of those compounds and compositions in medicine.

A further aspect of the present invention, described below in more detail is a synthetic process for conveniently preparing 4-substituted cytisine analogs.

The compounds and compositions of the invention are useful in medicine. For example, they may be used to prevent, treat or ameliorate symptoms of CNS disorders including addictive disorders such as nicotine, alcohol, drug addiction.

The compounds of this aspect of the invention have been identified by the inventors as having use in therapeutic applications, particularly in the treatment of addiction and/or dependence on drugs, alcohol and/or tobacco. While a limited number of 4-substituted analogues of cytisine have previously been disclosed, the limited binding data relating to those compounds that was made available did not demonstrate their applicability for use in medicine and the authors of those disclosures concluded that those compounds exhibited weak potency as modulators of receptors associated with neurological conditions including dependency and addiction. For example, Rouden et al., in Chemical Reviews, 2014, 114, pages 712 to 778, concluded (on page 732 of that document) that the 4-cytisine analogues tested exhibited 'no agonist activity and exhibited very low potencies in inhibiting nicotine activated channel function at both the α4β2 and α3β4 receptors'. Surprisingly and unexpectedly, however, the inventors have found that these compounds may exhibit advantages not previously realised, on the basis of newly generated data which is discussed below in greater detail.

Compounds having a wide range of substituents at the 4-position of cytisine have been identified as being of therapeutic benefit by the inventors.

As described herein, the compounds of the invention may be substituted with one or more substituents, as described herein, or as exemplified by particular compounds disclosed herein.

As used herein the term "aliphatic" encompasses the terms alkyl, alkenyl, alkynyl, each of which being optionally substituted as set forth below.

As used herein, an "alkyl" group refers to a saturated aliphatic hydrocarbon group containing 1-12 (e.g., 1-8, 1-6, or 1-4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic) carbonyl, (cycloaliphatic)carbonyl, or (heterocycloaliphatic)

carbonyl], nitro, cyano, amido [e.g., (cycloalkylalkyl)carbonylamino, arylcarbonylamino, aralkylcarbonylamino, (heterocycloalkyˆcarbonylamino, (heterocycloalkylalkyˆ-carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, or heterocycloaliphaticamino], sulfonyl [e.g., aliphatic-$SO_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, or hydroxy.

As used herein, an "alkenyl" group refers to an aliphatic carbon group that contains 2-12 (e.g., 2-8, 2-6, or 2-4) carbon atoms and at least one double bond. Like an alkyl group, an alkenyl group can be straight or branched. Examples of an alkenyl group include, but are not limited to allyl, vinyl, isoprenyl 1-propenyl, 2-propenyl, 1-butenyl, 2-butenyl, 3-butenyl, 1-pentenyl, 2-pentenyl, 3-pentenyl, 4-pentenyl, 5-pentenyl, 1-hexenyl, 2-hexenyl, 3-hexenyl, 4-hexenyl, 5-hexenyl and 6-hexenyl. An alkenyl group can be optionally substituted with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, heterocycloaliphaticamino, or aliphaticsulfonylamino], sulfonyl [e.g., alkyl-$SO_2$—, cycloaliphatic-$SO_2$—, or aryl-$SO_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroaralkoxy, alkoxycarbonyl, alkylcarbonyloxy, or hydroxy.

As used herein, an "alkynyl" group refers to an aliphatic carbon group that contains 2-12 (e.g., 2-8, 2-6, or 2-4) carbon atoms and has at least one triple bond. An alkynyl group can be straight or branched. Examples of an alkynyl group include, but are not limited to, propargyl, butynyl, acetylenyl, 1-propynyl, 2-propynyl, 1-butynyl, 2-butynyl, 3-butynyl, 1-pentynyl, 2-pentynyl, 3-pentynyl, 4-pentynyl, 5-pentynyl, 1-hexynyl, 2-hexynyl, 3-hexynyl, 4-hexynyl, 5-hexynyl and 6-hexynyl. An alkynyl group can be optionally substituted with one or more substituents such as aroyl, heteroaroyl, alkoxy, cycloalkyloxy, heterocycloalkyloxy, aryloxy, heteroaryloxy, aralkyloxy, nitro, carboxy, cyano, halo, hydroxy, sulfo, mercapto, sulfanyl [e.g., aliphaticsulfanyl or cycloaliphaticsulfanyl], sulfinyl [e.g., aliphaticsulfinyl or cycloaliphaticsulfinyl], sulfonyl [e.g., aliphatic-$SO_2$—, aliphaticamino-$SO_2$—, or cycloaliphatic-$SO_2$—], amido [e.g., aminocarbonyl, alkylaminocarbonyl, alkylcarbonylamino, cycloalkylaminocarbonyl, heterocycloalkylaminocarbonyl, cycloalkylcarbonylamino, arylaminocarbonyl, arylcarbonylamino, aralkylcarbonylamino, (heterocycloalkyl)carbonylamino, (cycloalkylalkyl)carbonylamino, heteroaralkylcarbonylamino, heteroarylcarbonylamino or heteroarylaminocarbonyl], urea, thiourea, sulfamoyl, sulfamide, alkoxycarbonyl, alkylcarbonyloxy, cycloaliphatic, heterocycloaliphatic, aryl, heteroaryl, acyl [e.g., (cycloaliphatic)carbonyl or (heterocycloaliphatic)carbonyl], amino [e.g., aliphaticamino], sulfoxy, oxo, carboxy, carbamoyl, (cycloaliphatic)oxy, (heterocycloaliphatic)oxy, or (heteroaryl)alkoxy.

As used herein, an "aryl" group used alone or as part of a larger moiety as in "aralkyl", "aralkoxy", or "aryloxyalkyl" refers to monocyclic (e.g., phenyl); bicyclic (e.g., indenyl, naphthalenyl, tetrahydronaphthyl, tetrahydroindenyl); and tricyclic (e.g., fluorenyl tetrahydrofluorenyl, tetrahydroanthracenyl, anthracenyl) ring systems in which the monocyclic ring system is aromatic or at least one of the rings in a bicyclic or tricyclic ring system is aromatic. The bicyblic and tricyclic groups include benzofused 2-3 membered carbocyclic rings. For example, a benzofused group includes phenyl fused with two or more $C_{4-8}$ carbocyclic moieties. An aryl is optionally substituted with one or more substituents including aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic ring of a benzofused bicyclic or tricyclic aryl); nitro; carboxy; amido; acyl [e.g., (aliphatic)carbonyl; (cycloaliphatic)carbonyl; ((cycloaliphatic)aliphatic)carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphatic-$SO_2$— or amino-$SO_2$—]; sulfinyl [e.g., aliphatic-S(O)— or cycloaliphatic-S(O)—]; sulfanyl [e.g., aliphatic-S—]; cyano; halo; hydroxy; mercapto; sulfoxy; urea; thiourea; sulfamoyl; sulfamide; or carbamoyl. Alternatively, an aryl can be unsubstituted.

Non-limiting examples of substituted aryls include haloaryl [e.g., mono-, di (such as p,m-dihaloaryl), and (trihalo)aryl]; (carboxy)aryl [e.g., (alkoxycarbonyl)aryl, ((aralkyl)carbonyloxy)aryl, and (alkoxycarbonyl)aryl]; (amido)aryl [e.g., (aminocarbonyl)aryl, (((alkylamino)alkyl)aminocarbonyl)aryl, (alkylcarbonyl)aminoaryl, (arylaminocarbonyl)aryl, and (((heteroaryl)amino)carbonyl)aryl]; aminoaryl [e.g., ((alkylsulfonyl)amino)aryl or ((dialkyl)amino)aryl; (cyanoalkyl)aryl; (alkoxy)aryl; (sulfamoyl)aryl [e.g., (aminosulfonyl)aryl]; (alkylsulfonyl)aryl; (cyano)aryl; (hydroxy alkyl)aryl; ((alkoxy)alkyl)aryl; (hydroxy)aryl, ((carboxy)alkyl)aryl; (((dialkyl)amino)alkyl)aryl; (nitroalkyl)aryl; (((alkylsulfonyl)amino)alkyl)aryl; ((heterocycloaliphatic)carbonyl)aryl; ((alkylsulfonyl)alkyl)aryl; (cyanoalkyl)aryl; (hydroxyalkyl)aryl; (alkylcarbonyl)aryl; alkylaryl; (trihaloalkyl)aryl; p-amino-m-alkoxycarbonylaryl; p-amino-m-cyanoaryl; p-halo-m-aminoaryl; or (m-(heterocycloaliphatic)-o-(alkyl))aryl.

As used herein, an "araliphatic" such as an "aralkyl" group refers to an aliphatic group (e.g., a $C_{1-4}$ alkyl group) that is substituted with an aryl group. "Aliphatic," "alkyl," and "aryl" are defined herein. An example of an araliphatic such as an aralkyl group is benzyl.

As used herein, an "aralkyl" group refers to an alkyl group (e.g., a $C_{1-4}$ alkyl group) that is substituted with an aryl group. Both "alkyl" and "aryl" have been defined above. An example of an aralkyl group is benzyl. An aralkyl is optionally substituted with one or more substituents such as aliphatic [e.g., alkyl, alkenyl, or alkynyl, including carboxyalkyl, hydroxyalkyl, or haloalkyl such as trifluoromethyl], cycloaliphatic [e.g., cycloalkyl or cycloalkenyl], (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxy carbonyl, alkylcarbonyloxy, amido [e.g., aminocarbonyl, alkylcarbonylamino, cycloalkylcarbonylamino, (cycloalkylalkylcarbonylamino, arylcarbonylamino, aralkylcarbonylamino, (heterocycloalkyl)carbonylamino, (heterocycloalkylalkyl)carbonylamino, heteroarylcarbonylamino, or heteroaralkylcarbonylamino], cyano, halo, hydroxy, acyl, mercapto, alkylsulfanyl, sulfoxy, urea, thiourea, sulfamoyl, sulfamide, oxo, or carbamoyl.

As used herein, a "bicyclic ring system" includes 8-12 (e.g., 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic aryls, and bicyclic heteroaryls.

As used herein, a "carbocycle" or "cycloaliphatic" group encompasses a "cycloalkyl" group and a "cycloalkenyl" group, each of which being optionally substituted as set forth below.

As used herein, a "cycloalkyl" group refers to a saturated carbocyclic mono- or bicyclic (fused or bridged) ring of 3-10 (e.g., 5-10) carbon atoms. Examples of cycloalkyl groups include cyclopropyl, cyclobutyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2]octyl, bicyclo[3.3.1]nonyl, bicyclo[3.3.2.]decyl, bicyclo[2.2.2]octyl, adamantyl, or ((aminocarbonyl)cycloalkyl)cycloalkyl.

A "cycloalkenyl" group, as used herein, refers to a non-aromatic carbocyclic ring of 3-10 (e.g., 4-8) carbon atoms having one or more double bonds. Examples of cycloalkenyl groups include cyclopentenyl, 1,4-cyclohexa-di-enyl, cycloheptenyl, cyclooctenyl, hexahydro-indenyl, octahydro-naphthyl, cyclohexenyl, cyclopentenyl, bicyclo[2.2.2]octenyl, or bicyclo[3.3.1]nonenyl.

A cycloalkyl or cycloalkenyl group can be optionally substituted with one or more substituents such as phosphor, aliphatic [e.g., alkyl, alkenyl, or alkynyl], cycloaliphatic, (cycloaliphatic) aliphatic, heterocycloaliphatic, (heterocycloaliphatic) aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic)aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl], cyano, halo, hydroxy, mercapto, sulfonyl [e.g., alkyl-SO$_2$— and aryl-SO$_2$—], sulfinyl [e.g., alkyl-S(O)—], sulfanyl [e.g., alkyl-S—], sulfoxy, urea, thiourea, sulfamoyl, sulfamide, oxo, or carbamoyl.

As used herein, the term "heterocycle" or "heterocycloaliphatic" encompasses a heterocycloalkyl group and a heterocycloalkenyl group, each of which being optionally substituted as set forth below.

As used herein, a "heterocycloalkyl" group refers to a 3-10 membered mono- or bicylic (fused or bridged) (e.g., 5- to 10-membered mono- or bicyclic) saturated ring structure, in which one or more of the ring atoms is a heteroatom (e.g., N, O, S, or combinations thereof). Examples of a heterocycloalkyl group include aziridinyl, piperidyl, piperazyl, tetrahydropyranyl, tetrahydrofuryl, thietanyl, oxolanyl, dioxanyl, dioxolanyl, thianyl, dithianyl, trithianyl, thiomorpholinyl, 1,3-dioxolanyl, imidazolidinyl, oxazolidyl, oxiranyl, oxetanyl, isoxazolidyl, morpholinyl, pyrrolidonyl, pyrazolidinyl, tetrahydrothiophenyl, oxathionlanyl, pyranyl, thiomorpholyl, octahydrobenzofuryl, octahydrochromenyl, octahydrothiochromenyl, octahydroindolyl, octahydropyridinyl, decahydroquinolinyl, octahydrobenzo[b]thiopheneyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.0$^{3,7}$]nonyl. A monocyclic heterocycloalkyl group can be fused with a phenyl moiety to form structures, such as tetrahydroisoquinoline, which would be categorized as heteroaryls.

A "heterocycloalkenyl" group, as used herein, refers to a mono- or bicylic (e.g., 5- to 10-membered mono- or bicyclic) non-aromatic ring structure having one or more double bonds, and wherein one or more of the ring atoms is a heteroatom (e.g., N, O, or S). Monocyclic and bicyclic heterocycloaliphatics are numbered according to standard chemical nomenclature.

A heterocycloalkyl or heterocycloalkenyl group can be optionally substituted with one or more substituents such as phospho, aliphatic [e.g., alkyl, alkenyl, or alkynyl], cycloaliphatic, (cycloaliphatic)aliphatic, heterocycloaliphatic, (heterocycloaliphatic)aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic) aliphatic)carbonylamino, (aryl)carbonylamino, (araliphatic)carbonylamino, (heterocycloaliphatic)carbonylamino, ((heterocycloaliphatic) aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic) carbonyl, (araliphatic)carbonyl, (heterocycloaliphatic)carbonyl, ((heterocycloaliphatic)aliphatic)carbonyl, or (heteroaraliphatic)carbonyl], nitro, cyano, halo, hydroxy, mercapto, sulfonyl [e.g., alkylsulfonyl or arylsulfonyl], sulfinyl [e.g., alkylsulfinyl], sulfanyl [e.g., alkylsulfanyl], sulfoxy, urea, thiourea, sulfamoyl, sulfamide, oxo, or carbamoyl.

A "heteroaryl" group, as used herein, refers to a monocyclic, bicyclic, or tricyclic ring system having 4 to 15 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo [b]thiophenyl, quinolinyl, or isoquinolinyl). Some examples of heteroaryl are azetidinyl, pyridyl (e.g. 2-pyridyl, 3-pyridyl, 4-pyridyl), pyridazinyl, pyrimidinyl, pyrazinyl, triazinyl, 1H-indazolyl, furyl, pyrrolyl, thienyl, thiazolyl, thiophenyl, oxazolyl, isoxazolyl, isothiazolyl, thiazolyl, oxadiazolyl, thiadiazolyl, imidazolyl, diazolyl, triazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo [b]thiophenyl, indazolyl, benzimidazolyl, benzthiazolyl, puryl, cinnolyl, quinolyl, quinazolyl, cinnolyl, phthalazyl, quinazolyl, quinoxalyl, isoquinolyl, 4H-quinolizyl, benzo-1,2,5-thiadiazolyl, or 1,8-naphthyridyl.

Without limitation, monocyclic heteroaryls include furyl, thiophenyl, 2H-pyrrolyl, pyrrolyl, oxazolyl, thazolyl, imidazolyl, pyrazolyl, isoxazolyl, isothiazolyl, 1,3,4-thiadiazolyl, 2H-pyranyl, 4H-pyranyl, pyridyl, pyridazyl, pyrimidyl, pyrazolyl, pyrazyl, or 1,3,5-triazyl. Monocyclic heteroaryls are numbered according to standard chemical nomenclature.

Without limitation, bicyclic heteroaryls include indolizyl, indolyl, isoindolyl, 3H-indolyl, indolinyl, benzo[b]furyl. benzo[b]thiophenyl, quinolinyl, isoquinolinyl, indolizinyl, isoindolyl, indolyl, benzo[b]furyl, benzo[b]thiophenyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

A heteroaryl is optionally substituted with one or more substituents such as aliphatic [e.g., alkyl, alkenyl, or alkynyl]; cycloaliphatic; (cycloaliphatic) aliphatic; heterocycloaliphatic; (heterocycloaliphatic)aliphatic; aryl; heteroaryl; alkoxy; (cycloaliphatic)oxy; (heterocycloaliphatic) oxy; aryloxy; heteroaryloxy; (araliphatic)oxy; (heteroaraliphatic)oxy; aroyl; heteroaroyl; amino; oxo (on a non-aromatic carbocyclic or heterocyclic ring of a bicyclic or tricyclic heteroaryl); carboxy; amido; acyl [e.g., (aliphatic)carbonyl; (cycloaliphatic)carbonyl; ((cycloaliphatic)aliphatic)carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphaticsulfonyl or aminosulfonyl]; sulfinyl [e.g., aliphaticsulfinyl]; sulfanyl [e.g., aliphaticsulfanyl]; nitro; cyano; halo; hydroxy; mercapto; sulfoxy; urea; thiourea; sulfamoyl; sulfamide; or carbamoyl. Alternatively, a heteroaryl can be unsubstituted.

Non-limiting examples of substituted heteroaryls include (halo)heteroaryl [e.g., mono- and di-(halo)heteroaryl]; (carboxy)heteroaryl [e.g., (alkoxycarbonyl)heteroaryl]; cyanoheteroaryl; aminoheteroaryl [e.g., ((alkylsulfonyl)amino) heteroaryl and ((dialkyl)amino)heteroaryl]; (amido) heteroaryl [e.g., aminocarbonylheteroaryl, ((alkylcarbonyl) amino)heteroaryl, ((((alkyl)amino)alkyl)aminocarbonyl) heteroaryl, (((heteroaryl)amino)carbonyl)heteroaryl, ((heterocycloaliphatic)carbonyl)heteroaryl, and ((alkylcarbonyl)amino)heteroaryl]; (cyanoalkyl)heteroaryl; (alkoxy) heteroaryl; (sulfamoyl)heteroaryl [e.g., (aminosulfonyl)heteroaryl]; (sulfonyl)heteroaryl [e.g., (alkylsulfonyl) heteroaryl]; (hydroxyalkyl)heteroaryl; (alkoxyalkyl) heteroaryl; (hydroxy)heteroaryl; ((carboxy)alkyl)heteroaryl; (((dialkyl)amino)alkyl]heteroaryl; (heterocycloaliphatic) heteroaryl; (cycloaliphatic)heteroaryl; (nitroalkyl)heteroaryl; (((alkylsulfonyl)amino)alkyl)heteroaryl; ((alkylsulfonyl)alkyl)heteroaryl; (cyanoalkyl)heteroaryl; (acyl) heteroaryl [e.g., (alkylcarbonyl)heteroaryl]; (alkyl) heteroaryl, and (haloalkyl)heteroaryl [e.g., trihaloalkylheteroaryl].

A "heteroaraliphatic" (such as a heteroaralkyl group) as used herein, refers to an aliphatic group (e.g., a $C_{1-4}$ alkyl group) that is substituted with a heteroaryl group. "Aliphatic," "alkyl," and "heteroaryl" have been defined above.

A "heteroaralkyl" group, as used herein, refers to an alkyl group (e.g., a $C_{1-4}$ alkyl group) that is substituted with a heteroaryl group. Both "alkyl" and "heteroaryl" have been defined above. A heteroaralkyl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino. (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, "cyclic moiety" and "cyclic group" refer to mono-, bi-, and tricyclic ring systems including cycloaliphatic, heterocycloaliphatic, aryl, or heteroaryl, each of which has been previously defined.

As used herein, a "bridged bicyclic ring system" refers to a bicyclic heterocyclicaliphatic ring system or bicyclic cycloaliphatic ring system in which the rings are bridged. Examples of bridged bicyclic ring systems include, but are not limited to, adamantanyl, norbornanyl, bicyclo[3.2.1] octyl, bicyclo[2.2.2]octyl, bicyclo[3.3.1]nonyl, bicyclo [3.2.3]nonyl, 2-oxabicyclo[2.2.2]octyl, 1-azabicyclo[2.2.2] octyl, 3-azabicyclo[3.2.1]octyl, and 2,6-dioxa-tricyclo [3.3.1.0$^{3,7}$]nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl) carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "amido" encompasses both "aminocarbonyl" and "carbonylamino". These terms when used alone or in connection with another group refer to an amido group such as —N($R^X$)—C(O)—$R^Y$ or —C(O)—N($R^X$)$_2$, when used terminally, and —C(O)— N($R^X$)— or —N($R^X$)—C (O)— when used internally, wherein $R^X$ and $R^Y$ are defined below. Examples of amido groups include alkylamido (such as alkylcarbonylamino or alkylaminocarbonyl), (heterocycloaliphatic)amido, (heteroaralkyl)amido, (heteroaryl) amido, (heterocycloalkyl)alkylamido, arylamido, aralkylamido, (cycloalkyl)alkylamido, or cyclo alkylamido.

As used herein, an "amino" group refers to —$NR^XR^Y$ wherein each of $R^X$ and $R^Y$ is independently hydrogen, aliphatic, cycloaliphatic, (cycloaliphatic)aliphatic, aryl, araliphatic, heterocycloaliphatic, (heterocycloaliphatic)aliphatic, heteroaryl, carboxy, sulfanyl, sulfinyl, sulfonyl, (aliphatic)carbonyl, (cycloaliphatic)carbonyl, ((cycloaliphatic) aliphatic)carbonyl, arylcarbonyl, (araliphatic)carbonyl, (heterocycloaliphatic)carbonyl, ((heterocycloaliphatic)aliphatic)carbonyl, (heteroaryl)carbonyl, or (heteroaraliphatic) carbonyl, each of which being defined herein and being optionally substituted. Examples of amino groups include alkylamino, dialkylamino, or arylamino. When the term "amino" is not the terminal group (e.g., alkylcarbonylamino), it is represented by —$NR^X$—. $R^X$ has the same meaning as defined above.

As used herein, an "acyl" group refers to a formyl group or $R^X$—C(O)— (such as alkyl-C(O)—, also referred to as "alkylcarbonyl") where $R^X$ and "alkyl" have been defined previously. Acetyl and pivaloyl are examples of acyl groups.

As used herein, an "aroyl" or "heteroaroyl" refers to an aryl-C(O)— or a heteroaryl-C(O)—. The aryl and heteroaryl portion of the aroyl or heteroaroyl is optionally substituted as previously defined.

As used herein, an "alkoxy" group refers to an alkyl-O— group where "alkyl" has been defined previously.

As used herein, a "carbamoyl" group refers to a group having the structure —O—CO—NR$^X$R$^Y$ or —NR$^X$—CO—O—R$^Z$, wherein R$^X$ and R$^Y$ have been defined above and R$^Z$ can be aliphatic, aryl, araliphatic, heterocycloaliphatic, heteroaryl, or heteroaraliphatic.

As used herein, a "carboxy" group refers to —COOH, —COOR$^X$, —OC(O)H, —OC(O)R$^X$, when used as a terminal group; or —OC(O)— or —C(O)O— when used as an internal group.

As used herein, a "haloaliphatic" group refers to an aliphatic group substituted with 1-3 halogen atoms. For instance, the term haloalkyl includes the group —CF$_3$.

As used Herein, a "mercapto" group refers to —SH.

As used herein, a "sulfo" group refers to —SO$_3$H or —SO$_3$R$^X$ when used terminally or —S(O)$_3$— when used internally.

As used herein, a "sulfamide" group refers to the structure —NR$^X$—S(O)$_2$—NR$^Y$R$^Z$ when used terminally and —NR$^X$—S(O)$_2$—NR$^Y$— when used internally, wherein R$^X$, R$^Y$, and R$^Z$ have been defined above.

As used herein, a "sulfonamide" group refers to the structure —S(O)$_2$—NR$^X$R$^Y$ or —NR$^X$—S(O)$_2$—R$^Z$ when used terminally; or —S(O)$_2$—NR$^X$— or —NR$^X$—S(O)$_2$— when used internally, wherein R$^X$, R$^Y$, and R$^Z$ are defined above.

As used herein a "sulfanyl" group refers to —S—R$^X$ when used terminally and —S— when used internally, wherein R$^X$ has been defined above. Examples of sulfanyls include aliphatic-S—, cycloaliphatic-S—, aryl-S—, or the like.

As used herein a "sulfinyl" group refers to —S(O)—R$^X$ when used terminally and —S(O)— when used internally, wherein R$^X$ has been defined above. Exemplary sulfinyl groups include aliphatic-S(O)—, aryl-S(O)—, (cycloaliphatic(aliphatic))—S(O)—, cycloalkyl-S(O)—, heterocycloaliphatic-S(O)—, heteroaryl-S(O)—, or the like.

As used herein, a "sulfonyl" group refers to —S(O)$_2$—R$^X$ when used terminally and —S(O)$_2$— when used internally, wherein R$^X$ has been defined above. Exemplary sulfonyl groups include aliphatic-S(O)$_2$—, aryl-S(O)$_2$—, (cycloaliphatic(aliphatic))—S(O)$_2$—, cycloaliphatic-S(O)$_2$—, heterocycloaliphatic-S(O)$_2$—, heteroaryl-S(O)$_2$—, (cycloaliphatic(amido(aliphatic)))—S(O)$_2$— or the like.

As used herein, a "sulfoxy" group refers to —O—SO—R$^X$ or —SO—O—R$^X$, when used terminally and —O—S(O)— or —S(O)—O— when used internally, where R$^X$ has been defined above.

As used herein, a "halogen" or "halo" group refers to fluorine, chlorine, bromine or iodine.

As used herein, an "alkoxycarbonyl," which is encompassed by the term carboxy, used alone or in connection with another group refers to a group such as alkyl-O—C(O)—.

As used herein, an "alkoxyalkyl" refers to an alkyl group such as alkyl-O-alkyl-, wherein alkyl has been defined above.

As used herein, a "carbonyl" refer to —C(O)—.

As used herein, an "oxo" refers to =O.

As used herein, the term "phospho" refers to phosphinates and phosphonates. Examples of phosphinates and phosphonates include —P(O)(R$^P$)$_2$, wherein R$^P$ is aliphatic, alkoxy, aryloxy, heteroaryloxy, (cycloaliphatic)oxy, (heterocycloaliphatic)oxy, aryl, heteroaryl, cycloaliphatic or amino.

As used herein, an "aminoalkyl" refers to the structure (R$^X$)$_2$N-alkyl-.

As used herein, a "cyanoalkyl" refers to the structure (NC)-alkyl-.

As used herein, a "urea" group refers to the structure —NR$^X$—CO—NR$^Y$R$^Z$ and a "thiourea" group refers to the structure —NR$^X$—CS—NR$^Y$R$^Z$ when used terminally and —NR$^X$—CO—NR$^Y$— or —NR$^X$—CS—NR$^Y$— when used internally, wherein R$^X$, R$^Y$, and R$^Z$ have been defined above.

As used herein, an "aliphatic chain" refers to a branched or straight aliphatic group (e.g., alkyl groups, alkenyl groups, or alkynyl groups). A straight aliphatic chain has the structure —[CH$_2$]$_v$—, where v is 1-12. A branched aliphatic chain is a straight aliphatic chain that is substituted with one or more aliphatic groups. A branched aliphatic chain has the structure —[CQQ]$_v$-. where each Q is independently a hydrogen or an aliphatic group; however, Q shall be an aliphatic group in at least one instance. The term aliphatic chain includes alkyl chains, alkenyl chains, and alkynyl chains, where alkyl, alkenyl, and alkynyl are defined above.

The phrase "optionally substituted" is used interchangeably with the phrase "substituted or unsubstituted." As described herein, compounds of the invention can optionally be substituted with one or more substituents, such as are illustrated generally above, or as exemplified by particular classes, subclasses, and species of the invention. As described herein, the variables R$^1$, R$^2$, R$^3$ and R$^4$, and other variables contained in formulae described herein encompass specific groups, such as alkyl and aryl. Unless otherwise noted, each of the specific groups for the variables R$^1$, R$^2$, R$^3$ and R$^4$ and other variables contained therein can be optionally substituted with one or more substituents described herein.

Each substituent of a specific group may be further optionally substituted with one to three of halo, cyano, oxo, alkoxy, hydroxy, amino, nitro, aryl, cycloaliphatic, heterocycloaliphatic, heteroaryl, haloalkyl, and alkyl. For instance, an alkyl group can be substituted with alkylsulfanyl and the alkylsulfanyl can be optionally substituted with one to three of halo, cyano, oxo, alkoxy, hydroxy, amino, nitro, aryl, haloalkyl, and alkyl. As an additional example, the cycloalkyl portion of a (cycloalkyl)carbonylamino can be optionally substituted with one to three of halo, cyano, alkoxy, hydroxy, nitro, haloalkyl, and alkyl. When two alkoxy groups are bound to the same atom or adjacent atoms, the two alkoxy groups can form a ring together with the atom(s) to which they are bound.

Compounds of the present invention are useful nAChRs and are useful in medicine, including for the treatment of CNS disorders such as addiction disorders.

Compounds

According to the present invention, there is provided a compound of formula (I):

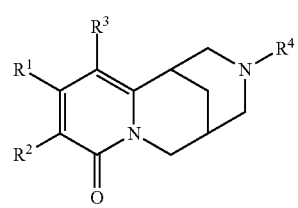

(I)

or a pharmaceutically acceptable salt, solvate and/or ester thereof, wherein:

R$^1$ is
hydroxyl;
halogen;

optionally substituted aliphatic;
optionally substituted cycloaliphatic;
optionally substituted heterocycloaliphatic;
optionally substituted aryl;
optionally substituted heteroaryl;
—(CH$_2$)m-NR$^6$R$^7$R$^8$, wherein
   R$^6$ and R$^7$ are each independently selected from the group consisting of hydrogen, halo, hydroxy, oxo, amino, amido, nitro, cyano, alkoxy, N-alkyl amino, N,N-dialkyl amino, phospho, carbonyl, carboxy, sulfoxy, sulfinyl, sulfonyl, sulfanyl, sulfamide, sulfo, mercapto, carbamoyl, methyl pivalate, trimethylsilyl, urea, thiourea optionally substituted aryl, optionally substituted heteroaryl, optionally substituted alkyl, optionally substituted cycloaliphatic, optionally substituted heterocycloaliphatic, optionally substituted heteroaryl, optionally substituted haloalkyl, optionally substituted aroyl, optionally substituted heteroaroyl, optionally substituted acyl, optionally substituted alkenyl, optionally substituted alkynyl, optionally substituted aralkyl, optionally substituted cycloalkyl, optionally substituted cycloalkenyl, optionally substituted heterocycloalkyl or optionally substituted heterocycloalkenyl or
   one of R$^6$ or R$^7$ is —CO—R$^9$, and the other of R$^6$ or R$^7$ is as defined above,
   R$^8$ is selected from the group consisting of hydrogen, halo, hydroxy, oxo, amino, amido, nitro, cyano, alkoxy, N-alkyl amino, N,N-dialkyl amino, phospho, carbonyl, carboxy, sulfoxy, sulfinyl, sulfonyl, sulfanyl, sulfamide, sulfo, mercapto, carbamoyl, methyl pivalate, trimethylsilyl, urea, thiourea optionally substituted aryl, optionally substituted heteroaryl, optionally substituted alkyl, optionally substituted cycloaliphatic, optionally substituted heterocycloaliphatic, optionally substituted heteroaryl, optionally substituted haloalkyl, optionally substituted aroyl, optionally substituted heteroaroyl, optionally substituted acyl, optionally substituted alkenyl, optionally substituted alkynyl, optionally substituted aralkyl, optionally substituted cycloalkyl, optionally substituted cycloalkenyl, optionally substituted heterocycloalkyl or optionally substituted heterocycloalkenyl, or is absent,
   R$^9$ is selected from the group consisting of hydrogen, halo, hydroxy, oxo, amino, amido, nitro, cyano, alkoxy, N-alkyl amino, N,N-dialkyl amino, phospho, carbonyl, carboxy, sulfoxy, sulfinyl, sulfonyl, sulfanyl, sulfamide, sulfo, mercapto, carbamoyl, methyl pivalate, trimethylsilyl, urea, thiourea optionally substituted aryl, optionally substituted heteroaryl, optionally substituted alkyl, optionally substituted cycloaliphatic, optionally substituted heterocycloaliphatic, optionally substituted heteroaryl, optionally substituted haloalkyl, optionally substituted aroyl, optionally substituted heteroaroyl, optionally substituted acyl, optionally substituted alkenyl, optionally substituted alkynyl, optionally substituted aralkyl, optionally substituted cycloalkyl, optionally substituted cycloalkenyl, optionally substituted heterocycloalkyl or optionally substituted heterocycloalkenyl,
   and m is 0, 1, 2, 3, 4 or 5,
—(CH$_2$)$_m$—O—(CH$_2$)$_n$—R$^{10}$, wherein
   R$^{10}$ is selected from the group consisting of hydrogen, halo, hydroxy, oxo, amino, amido, nitro, cyano, alkoxy, N-alkyl amino, N,N-dialkyl amino, phospho, carbonyl, carboxy, sulfoxy, sulfinyl, sulfonyl, sulfanyl, sulfamide, sulfo, mercapto, carbamoyl, methyl pivalate, trimethylsilyl, urea, thiourea optionally substituted aryl, optionally substituted heteroaryl, optionally substituted alkyl, optionally substituted cycloaliphatic, optionally substituted heterocycloaliphatic, optionally substituted heteroaryl, optionally substituted haloalkyl, optionally substituted aroyl, optionally substituted heteroaroyl, optionally substituted acyl, optionally substituted alkenyl, optionally substituted alkynyl, optionally substituted aralkyl, optionally substituted cycloalkyl, optionally substituted cycloalkenyl, optionally substituted heterocycloalkyl or optionally substituted heterocycloalkenyl, and
   m and n are each independently 0, 1, 2, 3, 4 or 5,
—CN
—COOR$^{12}$, wherein
   R$^{12}$ is selected from the group consisting of hydrogen, halo, hydroxy, oxo, amino, amido, nitro, cyano, alkoxy, N-alkyl amino, N,N-dialkyl amino, phospho, carbonyl, carboxy, sulfoxy, sulfinyl, sulfonyl, sulfanyl, sulfamide, sulfo, mercapto, carbamoyl, methyl pivalate, trimethylsilyl, urea, thiourea optionally substituted aryl, optionally substituted heteroaryl, optionally substituted alkyl, optionally substituted cycloaliphatic, optionally substituted heterocycloaliphatic, optionally substituted heteroaryl, optionally substituted haloalkyl, optionally substituted aroyl, optionally substituted heteroaroyl, optionally substituted acyl, optionally substituted alkenyl, optionally substituted alkynyl, optionally substituted aralkyl, optionally substituted cycloalkyl, optionally substituted cycloalkenyl, optionally substituted heterocycloalkyl or optionally substituted heterocycloalkenyl,
—(CH$_2$)$_o$—CO—(CH$_2$)$_p$—R$^{13}$, wherein
   R$^{13}$ is selected from the group consisting of hydrogen, halo, hydroxy, oxo, amino, amido, nitro, cyano, alkoxy, N-alkyl amino, N,N-dialkyl amino, phospho, carbonyl, carboxy, sulfoxy, sulfinyl, sulfonyl, sulfanyl, sulfamide, sulfo, mercapto, carbamoyl, methyl pivalate, trimethylsilyl, urea, thiourea optionally substituted aryl, optionally substituted heteroaryl, optionally substituted alkyl, optionally substituted cycloaliphatic, optionally substituted heterocycloaliphatic, optionally substituted heteroaryl, optionally substituted haloalkyl, optionally substituted aroyl, optionally substituted heteroaroyl, optionally substituted acyl, optionally substituted alkenyl, optionally substituted alkynyl, optionally substituted aralkyl, optionally substituted cycloalkyl, optionally substituted cycloalkenyl, optionally substituted heterocycloalkyl or optionally substituted heterocycloalkenyl, and
   o and p are each independently 0, 1, 2, 3, 4 or 5,
an amino acid or ester thereof,
acyl chloride,
a protecting group, or
cytisine,
R$^2$, R$^3$ and R$^4$ are each independently selected from the group consisting hydrogen, halo, hydroxy, oxo, amino, amido, nitro, cyano, alkoxy, N-alkyl amino, N,N-dialkyl amino, phospho, carbonyl, carboxy, sulfoxy, sulfinyl, sulfonyl, sulfanyl, sulfamide, sulfo, mercapto, carbamoyl, methyl pivalate, trimethylsilyl, urea, thiourea optionally substituted aryl, optionally substituted heteroaryl, optionally substituted alkyl, optionally substituted cycloaliphatic, optionally substituted heterocycloaliphatic, optionally substituted heteroaryl, optionally substituted haloalkyl, optionally substituted aroyl, optionally substituted heteroaroyl, optionally substituted acyl, optionally substituted alkenyl, optionally substituted alkynyl, optionally substituted aralkyl, optionally substituted cycloalkyl, optionally substituted cycloalkenyl, optionally substituted heterocycloalkyl or optionally substituted heterocycloalkenyl, amino acid or cytisine, or $R^4$ may be a protecting group, or a group having the structure —$(CH_2)$v-FORMULA 1, wherein v is 0, 1, 2, 3, 4, 5 or 6 and FORMULA 1 is a compound of Formula (I) as described herein.

provided that, when $R^2$, $R^3$, and $R^4$ are hydrogen, $R^1$ is not methyl, ethyl, ethenyl, hydroxymethyl, fluoromethyl, —$CH_2$—O-cyclohexylmethyl, —$CH_2$—O-benzyl, —$CH_2$—O—$CH_2$—$C_6H_4$—$CF_3$, —$CH_2$—$C_6H_4$—F, —$CH_2$—O—$CH_2$—$CH_2$—$CH_3$, —COOMe, —$CONH_2$, —$NH_2$, or —NH—CO—$CH_3$, or when the compound is for use in medicine, and $R^2$, $R^3$, and $R^4$ are hydrogen, $R^1$ is not methyl, hydroxymethyl, fluoromethyl, bromine, fluorine, chlorine, tolyl, —$CH_2$—O-cyclohexylmethyl, —$CH_2$—O-benzyl, —$CH_2$—O—$CH_2$—$C_6H_4$—$CF_3$, —$CH_2$—$C_6H_4$—F, —$CH_2$—O—$CH_2$—$CH_2$—$CH_3$, —COOMe, —$CONH_2$, —$NH_2$, or —NH—CO—$CH_3$.

As explained above, the substituent at the $R^1$ position may be an optionally substituted aliphatic; optionally substituted cycloaliphatic; optionally substituted heterocycloaliphatic; optionally substituted aryl; optionally heteroaryl.

In embodiments of the invention, the substituent at the $R^1$ position may be a $C_{1-8}$, a $C_{1-4}$ or $C_{3-8}$ alkyl group, which may or may not be substituted, for example, propyl, isopropyl, butyl or tert-butyl. In certain embodiments of the invention, the substituent at the $R^1$ position may be a substituted $C_{1-2}$ alkyl group or a $C_{3-8}$ optionally substituted alkyl group. In such embodiments, the $C_{1-2}$ alkyl group may be a substituent other than hydroxymethyl or fluoromethyl.

Examples of substituted alkyl groups that are envisaged as being employed at substituents at the $R^1$ position in the compounds of the present invention include substituted methyl groups, for example aminomethyl, halogenated methyl e.g. chloromethyl, dichloromethyl, trichloromethyl, difluoromethyl, trifluoromethyl bromomethyl, dibromomethyl or tribromomethyl; substituted ethyl groups, for example 1- or 2-aminoethyl, hydroxyethyl, halogenated ethyl e.g. 2,2,2-trichloroethyl, 2,2,2-tribromoethyl or 2,2,2-trifluoroethyl; substituted propyl groups, for example 1-, 2- or 3-aminomethyl; hydroxypropyl; or halogenated propyl.

In embodiments of the invention, the substituent at the $R^4$ position may be unsubstituted or substituted aryl. For example, the substituent may be a phenyl group, or may be a substituted phenyl group, for example a halogenated phenyl group, such as chlorophenyl, bromophenyl, fluorophenyl, perchlorophenyl, perbromophenyl, perfluorophenyl; or tolyl, aniline, phenol, styrene, benzonitrile, anisole, acetophenone, benzaldehyde or benzoic acid groups.

In alternative embodiments, the substituent at the $R^1$ position may be an optionally substituted heteroaryl, such as benzyloxy pyridine, pyridone (e.g. 2-pyridone), pyridine (e.g. 2-pyridine, 3-pyridine or 4 pyridine), phenyltriazole, optionally substituted triazole, and triazole methylpivalate groups.

The $R^1$ substituent may alternatively be an optionally substituted cycloalkyl or heterocycloalkyl, such as cyclopentyl, cyclohexyl, morpholinyl, piperidyl, piperazyl, tetrahydrofuryl, oxolanyl or dioxanyl.

Examples of optionally substituted alkenyl groups that may be included at the $R^1$ position include $C_{2-8}$ alkenyl, such as vinyl, acrylate or —C=C—$C_6H_5$ groups.

Optionally substituted alkynyl groups that may be present at the $R^1$ position include $C_{2-8}$ alkynyl: —C≡C—$C_6H_5$ or —C≡C-trimethylsilyl groups.

Additionally, other groups that may be employed as $R^1$ substituents in the compounds of the present invention include the following groups:

—$(CH_2)_m$—$NR^6R^7R^8$, where $R^6$, $R^7$ and $R^8$ are as defined above. In such embodiments, the compounds of the invention may include amine, N-alkyl amine, N,N-dialkyl amine and amide groups as substituents at the $R^1$ position. Examples of such groups that are envisaged for inclusion at that position include amine, methylamine, ethylamine, propylamine, isopropylamine, benzylamine, dimethylamine, trimethylammonium methyl, dimethylamino methyl, benzamido and acetamido groups. In embodiments of the invention, where m is zero and $R^8$ is absent, $R^6$ and $R^7$ may not both be hydrogen and/or neither of $R^6$ or $R^7$ may be an oxo.

—$(CH_2)_n$—O—$(CH_2)_o$—$R^{10}$, wherein $R^{10}$ is as defined above. In such embodiments, the compounds of the invention may include groups including ether linkages at the $R^1$ position. Examples of such groups that are envisaged for inclusion at that position include methoxy, ethoxy, propoxy, benzyloxy or trifluoromethylbenzyloxy groups. In embodiments of the invention, the proviso applies that the substituent at $R^1$ is not a propoxymethyl group (i.e. —$CH_2$—O—$CH_2$—$CH_2CH_3$), an alkoxymethyl group, or a group having the following structure: —$CH_2$—O—$CH_2$—$C_6H_4$—$R^{12}$ or —$CH_2$—O—$CH_2$—$C_6H_{10}$—$R^{12}$, wherein $R^{12}$ is hydrogen, trifluoromethyl, substituted phenyl, halo or fluorine.

—CN

—$COOR^{12}$, wherein $R^{12}$ is as defined above. In such embodiments, the compounds of the invention may include carboxylic acid groups or esters at the $R^1$ position, for example ethyl ester, propyl ester, isopropyl ester, butyl ester or phenyl ester. In embodiments of the invention, the substituent at $R^1$ may be a substituent other than a $C_{1-3}$ alkyl ester group, or a methyl ester group.

—$(CH_2)_p$—CO—$(CH_2)_q$—$R^{13}$, wherein $R^{13}$ is as defined above. In such embodiments, the compounds of the invention may include ketone or aldehyde groups at the $R^1$ position, for example acetophenone. In certain embodiments, the substituent at $R^1$ is a substituent other than —CO—$NH_2$.

an amino acid, for example a naturally occurring amino acid or ester thereof, e.g. alanine, arginine, asparagine, aspartate, cysteine, glutamine, glutamate, glycine, histidine, isoleucine, leucine, lysine, methionine, phenylalanine, proline, serine, threonine, tryptophan, tyrosine, valine, or methyl, ethyl, propyl or isopropyl esters thereof.

In embodiments of the invention in which the compounds of the invention include an amino acid or ester thereof at the $R^1$ position, the amino acid (or ester) may be bonded to the pyridine ring on the cytisine basic structure via any atom (e.g. via an oxygen, carbon, sulphur or nitrogen atom), for example, via the oxygen atom in the acid unit thus forming an amide of an amino cytisine, or via the nitrogen atom in the amine unit.

acyl chloride.
- a protecting group, e.g. a tert-Butyloxycarbonyl (Boc), formyl, acetyl (Ac), succinyl (Suc), methoxysuccinyl (MeOSuc), benzyloxycarbonyl (Cbz), or fluorenylmethoxycarbonyl (Fmoc) or a protected boryl protecting group, optionally having the structure (RO)$_2$B— such as (pinacolato)borane (BPin) and (catecholato) borane (BCat). In embodiments of the invention, any protecting group commonly employed in organic synthesis, may be employed, for example those outlined in Gross and Mienhoffer, eds., The Peptides, Vol. 3, Academic Press, New York, 1981, pp. 3-88; Green and Wuts, Protective Groups in Organic Synthesis, 3rd edition, John Wiley and Sons, Inc., New York, 1999, the contents of which are incorporated by reference.
- cytisinyl. In embodiments, the compound of the invention may be a cytisine-cytisine dimer. The cytisine compounds may be coupled directly to each other, e.g. via the carbon atoms at the 3-, 4- or 5-position of each respective compound. Alternatively, the two cytisine structures may be coupled via a linker, for example via a carbon, oxygen, or nitrogen atom. Where a linker is employed, this may itself bear a functionalising group, e.g. $C_{1-6}$ alkyl.

The substituents at positions $R^2$ to $R^4$ are as defined above. In embodiments of the invention, $R^2$ and $R^3$ or each of $R^2$, $R^3$ and $R^4$ may be hydrogen. Alternatively, $R^2$ may be halogen while $R^3$ and $R^4$ are hydrogen. In some embodiments of the invention, the substituent at $R^4$ may be a substituent other than $C_{2-6}$ alkyl.

In embodiments of the invention, the substituent at position $R^4$ may be a protecting group, e.g. tert-Butyloxycarbonyl (Boc) formyl, acetyl (Ac), succinyl (Suc), methoxysuccinyl (MeOSuc), benzyloxycarbonyl (Cbz), or fluorenylmethoxycarbonyl (Fmoc). or a borylated protecting group, optionally having the structure B(OR)$_2$ such as (pinacolato)borane (BPin) and (catecholato)borane (BCat). In embodiments of the invention, any protecting group commonly employed in organic synthesis, may be employed, for example those outlined in Gross and Mienhoffer, eds., The Peptides, Vol. 3, Academic Press, New York, 1981, pp. 3-88; Green and Wuts, Protective Groups in Organic Synthesis, 3rd edition, John Wiley and Sons, Inc., New York, 1999, the contents of which are incorporated by reference.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a 13C- or 14C-enriched carbon are within the scope of this invention.

Exemplary compounds of the present invention include, but are not limited to the following compounds:
4-Bpincytisine
4-Hydroxycytisine
(+)4-Hydroxycytisine
(−)4-Methoxycytisine
4-Methoxycytisine
4-(N-Benzylamino)cytisine
(+)4-(N-Benzylamino)cytisine
(−)4-(2,2,2-Trifluoroethyl)cytisine
4-(2,2,2-Trifluoroethyl)cytisine
(−)4-(Perfluorophenyl)cytisine
4-(Perfluorophenyl)cytisine
(−)4-(2-Pyridinyl)cytisine
4-(2-Pyridinyl)cytisine
(−)4-(3-Pyridinyl)cytisine
4-(3-Pyridinyl)cytisine
(−)4-(4-Pyridinyl)cytisine
4-(4-Pyridinyl)cytisine
4-(4-(2-Benzyloxy)pyridine)cytisine
4-(4-(2-Pyridone))cytisine
(+)4-(4-(2-Pyridone))cytisine
(−)4-Chlorocytisine
(−)4-Iodocytisine
(+)4-Iodocytisine
(−)4-Trifluoromethylcytisine
4-Trifluoromethylcytisine
(−)4-Bromocytisine
(+)4-Aminocytisine
(−)4-Fluorocytisine
4-(N-Methylamino)cytisine
(+)4-(N-Methylamino)cytisine
4-(N, N'-dimethylamino)cytisine
(+)4-(N, N'-dimethylamino)cytisine
4-(N-Benzoylamino)cytisine
(+)4-(N-Benzoylamino)cytisine
(+)4-(N-Acetylamino)cytisine
4-(N-morpholine)cytisine
(+)4-(N-morpholine)cytisine
4-(N-(L-proline methyl ester)cytisine
(+)4-(N-(L-proline methyl ester)cytisine
(−)4-(N-(L-proline)cytisine
4-(N-(L-proline)cytisine
(−)4-(Carboxymethyl)cytisine
(−)4-Carboxylic acid cytisine
4-Carboxylic acid cytisine
(−)4-(Hydroxymethyl)cytisine
(−)4-((Trifluoromethyl)benzyl)oxycytisine
(−)4-Methylcytisine
(−)4-Vinylcytisine
(+)4-Vinylcytisine
(−)4-Ethylcytisine
(+)4-p-Tolylcytisine
(−)4-(N-2-pyridone)cytisine
4-(N-2-pyridone)cytisine
4-(Trimethylsilylacetylene)cytisine
(−)4-(Acetylenyl)cytisine
4-(Acetylenyl)cytisine
4-(Phenylacetylene)cytisine
(+)4-(Phenylacetylene)cytisine
4-(E-2-Propenoate methyl ester)cytisine
(+)4-(E-2-Propenoate methyl ester)cytisine
4-(E-(2-phenylethenyl))cytisine
(+)4-(E-(2-phenylethenyl))cytisine
4-(1-(4-phenyl)-NH-1, 2, 3, triazolyl)cytisine
(+)4-(1-(4-phenyl)-NH-1, 2, 3, triazolyl)cytisine
(−)4-(1,2,3-Triazol-1-yl)methylpivalate)cytisine
(+)4-(1,2,3-Triazol-1-yl)methylpivalate)cytisine
4-(NH-1, 2, 3-triazolyl)cytisine
(+)4-(NH-1, 2, 3-triazolyl)cytisine
4-(N-Ethylamino)cytisine
(+)4-(N-Ethylamino)cytisine 4-(N-Isopropylamino)cytisine
(+)4-(N-Isopropylamino)cytisine
(−)4-Cyanocytisine
4-Cyanocytisine
(−)4-(Carboxyamido)cytisine
(−)4-Aminomethylcytisine
4-Aminomethylcytisine
(−)4-(N-methyl-aminomethyl)cytisine
4-(N-methyl-aminomethyl)cytisine
(1R, 5S, 10S, 11aR)-10-(aminomethyl)decahydro-8H-1,5-methanopyrido[1,2-a][1,5]diazocine-8-one
Amino Bis(cytisine) derivative
Methylamino Bis(cytisine) derivative
(−)4-Tetrazoylcytisine
4-Tetrazoylcytisine
(−)4-(Trimethylammonium)methylcytisine
4-(Trimethylammonium)methylcytisine
(−)4-(N-acetyl)aminomethylcytisine
4-(N-acetyl)aminomethylcytisine
4-(N-Piperazine)cytisine
(+)4-(N-Piperazine)cytisine
(−)3-(Trifluoromethyl)-4-bromocytisine
3-(Trifluoromethyl)-4-bromocytisine
3-Bromo-4-iodocytisine
(+)3-Bromo-4-iodocytisine
3-Bromo-4-N-methylaminocytisine
(+)3-Bromo-4-N-methylaminocytisine
Syntheses While there have been limited disclosures in the prior art of 4-substituted cytisine compounds, no convenient synthesis of such compounds has been proposed previously. To the inventors' knowledge, no synthetic route for obtaining 4-substituted analogs of cytisine which starts from cytisine has been previously disclosed. Instead, such compounds had to be produced from a total synthesis starting from monocyclic materials. See for example, Scheme 1 of Kozikowski et al., ChemMedChem, 2007, 2, pages 1157 to 1161 and Gallagher et al., Synlett, 2010, pages 2798-2791.

According to a further aspect of the present invention, there is provided a process for producing 4-substituted cytisine analogs, comprising
i) providing a compound of Formula IIa

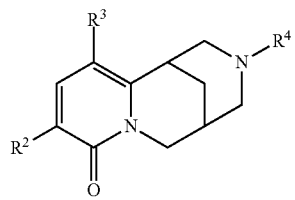

wherein $R^2$, $R^3$ and $R^4$ are each independently selected from the group consisting of hydrogen, halo, hydroxy, oxo, amino, amido, nitro, cyano, alkoxy, N-alkyl amino, N,N-dialkyl amino, phospho, carbonyl, carboxy, sulfoxy, sulfinyl, sulfonyl, sulfanyl, sulfamide, sulfo, mercapto, carbamoyl, methyl pivalate, trimethylsilyl, urea, thiourea optionally substituted aryl, optionally substituted heteroaryl, optionally substituted alkyl, optionally substituted cycloaliphatic, optionally substituted heterocycloaliphatic, optionally substituted heteroaryl, optionally substituted haloalkyl, optionally substituted aroyl, optionally substituted heteroaroyl, optionally substituted acyl, optionally substituted alkenyl, optionally substituted alkynyl, optionally substituted aralkyl, optionally substituted cycloalkyl, optionally substituted cycloalkenyl, optionally substituted heterocycloalkyl or optionally substituted heterocycloalkenyl, amino acid or cytisine, or $R^4$ may be a protecting group, or a group having the structure —$(CH_2)_v$-FORMULA 1, wherein v is 0, 1, 2, 3, 4, 5 or 6 and FORMULA 1 is a compound of Formula (I) as described herein;
ii) producing a compound of Formula IIb

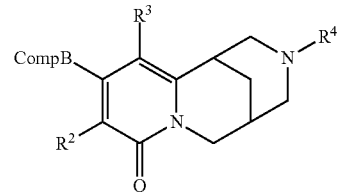

wherein $R^2$, $R^3$ and $R^4$ are as defined above, and BComp is a borylated complex, by contacting the compound of Formula IIa with a borylating agent;
iii) replacing BComp with $R^1$ to produce a compound of Formula I:

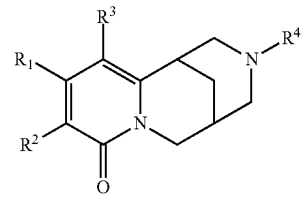

wherein $R^1$ is
hydroxyl;
halogen;
optionally substituted aliphatic;
optionally substituted cycloaliphatic;
optionally substituted heterocycloaliphatic;
optionally substituted aryl;
optionally substituted heteroaryl;
—$(CH_2)_m$—$NR^6R^7R^8$, wherein
$R^6$ and $R^7$ are each independently selected from the group consisting of hydrogen, halo, hydroxy, oxo, amino, amido, nitro, cyano, alkoxy, N-alkyl amino, N,N-dialkyl amino, phospho, carbonyl, carboxy, sulfoxy, sulfinyl, sulfonyl, sulfanyl, sulfamide, sulfo, mercapto, carbamoyl, methyl pivalate, trimethylsilyl, urea, thiourea optionally substituted aryl, optionally substituted heteroaryl, optionally substituted alkyl, optionally substituted cycloaliphatic, optionally substituted heterocycloaliphatic, optionally substituted heteroaryl, optionally substituted haloalkyl, optionally substituted aroyl, optionally substituted heteroaroyl, optionally substituted acyl, optionally substituted alkenyl, optionally substituted alkynyl, optionally substituted aralkyl, optionally substituted cycloalkyl, optionally substituted cycloalkenyl, optionally substituted heterocycloalkyl or optionally substituted heterocycloalkenyl or
one of $R^6$ or $R^7$ is —CO—$R^9$, and the other of $R^6$ or $R^7$ is as defined above,
$R^8$ is selected from the group consisting of hydrogen, halo, hydroxy, oxo, amino, amido, nitro, cyano, alkoxy, N-alkyl amino, N,N-dialkyl amino, phospho, carbonyl, carboxy, sulfoxy, sulfinyl, sulfonyl, sulfanyl, sulfamide, sulfo, mercapto, carbamoyl, methyl pivalate, trimethylsilyl, urea, thiourea optionally substituted aryl, optionally substituted heteroaryl, optionally substituted alkyl, optionally substituted cycloaliphatic, optionally substituted heterocycloaliphatic, optionally substituted heteroaryl, optionally substituted haloalkyl, optionally substituted aroyl, optionally substituted heteroaroyl, optionally substituted acyl, optionally substituted alkenyl, optionally substituted alkynyl, optionally substituted aralkyl, optionally substituted cycloalkyl, optionally substituted cycloalkenyl, optionally substituted heterocycloalkyl or optionally substituted heterocycloalkenyl, or is absent, $R^9$ is selected from the group consisting of hydrogen, halo, hydroxy, oxo, amino, amido, nitro, cyano, alkoxy, N-alkyl amino, N,N-dialkyl amino, phospho, carbonyl, carboxy, sulfoxy, sulfinyl, sulfonyl, sulfanyl, sulfamide, sulfo, mercapto, carbamoyl, methyl pivalate, trimethylsilyl, urea, thiourea optionally substituted aryl, optionally substituted heteroaryl, optionally substituted alkyl, optionally substituted cycloaliphatic, optionally substituted heterocycloaliphatic, optionally substituted heteroaryl, optionally substituted haloalkyl, optionally substituted aroyl, optionally substituted heteroaroyl, optionally substituted acyl, optionally substituted alkenyl, optionally substituted alkynyl, optionally substituted aralkyl, optionally substituted cycloalkyl, optionally substituted cycloalkenyl, optionally substituted heterocycloalkyl or optionally substituted heterocycloalkenyl, and m is 0, 1, 2, 3, 4 or 5, —$(CH_2)_m$—O—$(CH_2)_n$—$R^{10}$, wherein $R^{10}$ is selected from the group consisting of hydrogen, halo, hydroxy, oxo, amino, amido, nitro, cyano, alkoxy, N-alkyl amino, N,N-dialkyl amino, phospho, carbonyl, carboxy, sulfoxy, sulfinyl, sulfonyl, sulfanyl, sulfamide, sulfo, mercapto, carbamoyl, methyl pivalate, trimethylsilyl, urea, thiourea optionally substituted aryl, optionally substituted heteroaryl, optionally substituted alkyl, optionally substituted cycloaliphatic, optionally substituted heterocycloaliphatic, optionally substituted heteroaryl, optionally substituted haloalkyl, optionally substituted aroyl, optionally substituted heteroaroyl, optionally substituted acyl, optionally substituted alkenyl, optionally substituted alkynyl, optionally substituted aralkyl, optionally substituted cycloalkyl, optionally substituted cycloalkenyl, optionally substituted heterocycloalkyl or optionally substituted heterocycloalkenyl, and m and n are each independently 0, 1, 2, 3, 4 or 5,

—CN

—$COOR^{12}$, wherein $R^{12}$ is selected from the group consisting of hydrogen, halo, hydroxy, oxo, amino, amido, nitro, cyano, alkoxy, N-alkyl amino, N,N-dialkyl amino, phospho, carbonyl, carboxy, sulfoxy, sulfinyl, sulfonyl, sulfanyl, sulfamide, sulfo, mercapto, carbamoyl, methyl pivalate, trimethylsilyl, urea, thiourea optionally substituted aryl, optionally substituted heteroaryl, optionally substituted alkyl, optionally substituted cycloaliphatic, optionally substituted heterocycloaliphatic, optionally substituted heteroaryl, optionally substituted haloalkyl, optionally substituted aroyl, optionally substituted heteroaroyl, optionally substituted acyl, optionally substituted alkenyl, optionally substituted alkynyl, optionally substituted aralkyl, optionally substituted cycloalkyl, optionally substituted cycloalkenyl, optionally substituted heterocycloalkyl or optionally substituted heterocycloalkenyl, —$(CH_2)_o$—CO—$(CH_2)_p$—$R^{13}$, wherein $R^{13}$ is selected from the group consisting of hydrogen, halo, hydroxy, oxo, amino, amido, nitro, cyano, alkoxy, N-alkyl amino, N,N-dialkyl amino, phospho, carbonyl, carboxy, sulfoxy, sulfinyl, sulfonyl, sulfanyl, sulfamide, sulfo, mercapto, carbamoyl, methyl pivalate, trimethylsilyl, urea, thiourea optionally substituted aryl, optionally substituted heteroaryl, optionally substituted alkyl, optionally substituted cycloaliphatic, optionally substituted heterocycloaliphatic, optionally substituted heteroaryl, optionally substituted haloalkyl, optionally substituted aroyl, optionally substituted heteroaroyl, optionally substituted acyl, optionally substituted alkenyl, optionally substituted alkynyl, optionally substituted aralkyl, optionally substituted cycloalkyl, optionally substituted cycloalkenyl, optionally substituted heterocycloalkyl or optionally substituted heterocycloalkenyl, and o and p are each independently 0, 1, 2, 3, 4 or 5, an amino acid or ester thereof, acyl chloride, a protecting group, or cytisinyl.

The starting material may be any compound encompassed within Formula IIa as outlined above. However, one advantage of the present invention is that the process can advantageously be operated using cytisine as a starting material. Thus, in embodiments, all of $R^2$, $R^3$ and $R^4$ may be hydrogen. Alternatively, the substituent at position $R^4$ may be a protecting group, or a group having the structure —$(CH_2)$v-FORMULA 1, wherein v is 0, 1, 2, 3, 4, 5 or 6 and FORMULA 1 is a compound of Formula (I) as described herein.

Thus, in embodiments, the compound of Formula IIa may comprise a protecting group at $R^4$ and the process of the invention may comprise the step of adding the protecting group to a compound of Formula IIa (which encompasses cytisine). Those skilled in the art will be familiar with techniques for adding protecting groups to secondary amines and any process step for doing so is encompassed within the scope of the invention. For example, in embodiments where the protecting group to be added at the $R^4$ position is Boc (tert-butoxyl carbonyl), the process involves the step of providing a Boc containing reagent (e.g. $(Boc)_2O$) and contacting it with cytisine in an appropriate solvent (e.g. one containing tetrahydrofuran and sodium tricarbonate).

Thus, in embodiments of the invention, the protecting group present at the $R^4$ position may be Boc. Alternative protecting groups that may be used include formyl, acetyl (Ac), succinyl (Suc), methoxysuccinyl (MeOSuc), benzyloxycarbonyl (Cbz), or fluorenylmethoxycarbonyl (Fmoc), or a borylated protecting group, optionally having the structure $(RO)_2B$—$B(OR)_2$ such as bis(pinacolato)diborane ($B_2Pin_2$) and bis(catecholato)diborane ($B_2Cat_2$). In embodiments of the invention, any protecting group commonly employed in organic synthesis, may be employed, for example those outlined in Gross and Mienhoffer, eds., The Peptides, Vol. 3, Academic Press, New York, 1981, pp. 3-88; Green and Wuts, Protective Groups in Organic Synthesis, 3rd edition, John Wiley and Sons, Inc., New York, 1999, the contents of which are incorporated by reference.

The borylated agent employed in step ii) of the process of the present invention may be any borylating agent known to one skilled in the art of borylation chemistry. For example, the borylating agent may be a dialkyloxyborane or an alkylborane. Examples of dialkyloxyboranes include bis (pinacolato)diborane ($B_2Pin_2$) and bis(catecholato)diborane ($B_2Cat_2$) as well as any other borylating agent having the general formula $(RO)_2$—B—B—$(OR)_2$ or $HB(OR)_2$, for example those disclosed in Hartwig et al, Chemical Reviews, 2010, 110, pages 890-931, the contents of which are incorporated by reference. Examples of alkylborane borylating agents include 9-borabicyclo(3.3.1)nonane (9-BBN), B-alkyl-9-oxa-10-borabicyclo[3.3.2]decane (OBBD), disiamylborane, thexylborane and $HB(cHex)_2$.

In embodiments of the invention, the molar ratio of borylating agent:starting material of Formula IIa may range from about 10 or less:about 1, about 7 or less:about 1, or about 5 or less:about 1. Additionally or alternatively, the molar ratio of borylating agent:starting material of formula IIa may range from about 0.1 or more:about 1, about 0.2 or more:about 1, about 0.3 or more:about 1, about 0.4 or more:about 1, or about 0.5 or more:about 1.

In certain embodiments of the invention, the borylating agent may be in molar excess as compared to the starting material of Formula IIa. This may be preferable in certain embodiments in which cytisine is employed as the starting material of formula IIa.

In alternative embodiments of the invention, the starting material of Formula IIa may be in molar excess as compared to the borylating agent. This may be preferable in certain embodiments in which certain analogs of cytisine (e.g. N-boc cytisine) are employed as the starting material of formula IIa.

The reaction in step ii) of the process of the present invention may be catalysed using catalysts known to those skilled in the art. In embodiments of the invention, step ii) is catalysed, for example using a transition metal catalyst. In preferred embodiments, the catalyst used contains iridium, palladium, zinc, nickel and/or rhodium atoms, which may be provided in the form of an organic co-ordination complex. Specific examples of catalysts that may be used in the process of the present invention include $Ir[(COD)(OMe)]_2$, $PdCl_2$, $Pd/P(t-bu)_3$, $Pd(dba)_2$, $NiCl_2$, $[RhCl(cod)]_2$, or $Et_2Zn$. Iodine may also or alternatively be used as a catalyst.

Step ii) of the process of the present invention may be carried out in a solvent. Any solvent which is capable of permitting the borylation process to proceed may be employed in the process of the present invention. Examples of solvents that may be employed include esters (e.g. ethyl acetate), ethers (e.g. dioxane, tetrahydrofuran), ketones (e.g. 2-butanone), sulfoxides (e.g. DMSO) aromatics (e.g. toluene), fluorinated aromatics (e.g. trifluorotoluene) and alkanes (e.g. cyclohexane, n-pentane, n-hexane).

In the process of the present invention, a ligand may be employed in step ii).

Examples of ligands that may be employed include aromatic or heteroaromatic compounds which may be monocyclic or multicyclic, for example phenanthroline compounds including, but not limited to, phenanthroline (phen), dimethylphenanthroline (me2phen) tetramethyl-1,10-phenanthroline (me4phen) and/or bathophenanthroline (bathophen); bipyridyl compounds such as bipyridyl (bpy), di-tert-butyl-2,2'-bipyridyl (dtbpy), 2,2'-bipyridine (bpy), dimethoxy-2,2'-bipyridyl (MeO-bpy); and/or other compounds such as 1,1'-bis(diphenylphosphino)ferrocene (dppf), bis(2-di-tert-butylphosphinophenyl)ether, 1,3-bis(diphenylphosphino)propane (dppp), 1,2-bis(diphenylphosphino)ethane (dppe), hexamethylbenzene (C6Me6), neocuproine, and xantphos. Other examples include 1,2-bis (dimethylphosphino)ethane (dmpe) and those disclosed in Hartwig et al, Chemical Reviews, 2010, 110, pages 890-931, the contents of which are incorporated by reference, and also the compounds illustrated below:

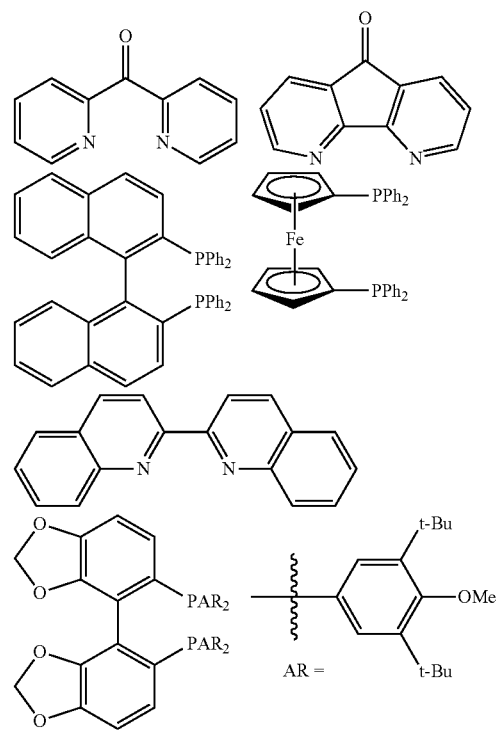

Alternatively, examples of ligands that may be employed include aromatic or heteroaromatic compounds which may be multicyclic, for example tetramethyl-1,10-phenanthroline (Me4phen), di-tert-butyl-2,2'-bipyridyl (dtbpy), 2,2'-bipyridine (bpy), 1,1'-bis(diphenylphosphino)ferrocene (dppf), bis(2-di-tert-butylphosphinophenyl)ether, 1,3-bis(diphenylphosphino)propane (dppp), 1,2-bis(diphenylphosphino)ethane (dppe), hexamethylbenzene (C6Me6) and xantphos. Other examples include 1,2-bis(dimethylphosphino)ethane (dmpe) and those disclosed in Hartwig et al, Chemical Reviews, 2010, 110, pages 890-931, the contents of which are incorporated by reference.

The inventors of the process of the invention have found that the molar ratio of ligand (where used) to starting material of formula IIa can impact on the rate of conversion to the borylated compound of formula IIb. In embodiments of the invention, the molar ratio of ligand:starting material of Formula IIa is less than about 2:1, less than about 1.5:1, less than about 1:1, less than about 0.75:1, less than about 0.5:1, less than about 0.1:1, less than about 0.05:1 to at least about 0.001:1.

Borylation step ii) may be conducted at any temperature provided that the borylation proceeds at an acceptable rate. In embodiments of the invention, the reaction may be carried out at a temperature of about 0° C., about 10° C., about 20° C., about 30° C., about 40° C. or about 50° C. to about 100° C., about 120° C., or about 150° C.

The inventors of the process of the invention have found that the molar ratio of borylating agent to starting material of formula IIa can impact on the rate of conversion to the borylated compound of formula IIb. In embodiments of the invention, the molar ratio of borylating agent:starting material of Formula IIa is at least about 0.5:1, at least about 0.75:1, at least about 1:1, at least about 1.5:1, at least about 2:1, at least 2.5:1 or at least 3:1 optionally to about 5:1, or about 10:1.

The selective and efficient synthesis of 4-substituted analogues of cytisine has been achieved regardless of the order in which the starting material, solvent, catalyst, ligand and/or borylating agent are added.

In certain embodiments of the invention, the borylating agent and the starting material of Formula IIa are added simultaneously or substantially simultaneously into a reaction zone. In such embodiments, the reaction zone may or may not have been pre-loaded with solvent, catalyst and/or ligand.

In alternative embodiments of the invention, the borylating agent may be added to the reaction zone (optionally pre-loaded with solvent, catalyst and/or ligand) prior to the starting material of Formula IIa being added. In such embodiments, the borylating agent may be present in the reaction zone (optionally with solvent, catalyst and/or ligand) for a period of time, e.g. about 1 or more, about 2 or more, or about 5 or more minutes, prior to the addition of the starting material of Formula IIa.

One advantage of the process of the present invention is that the crude product obtained in step ii) does not require purification prior to step iii) being commenced. Thus, in embodiments of the invention, no purification step is carried out between steps ii) and iii).

This advantage of the process of the present invention enables step ii) and at least the commencement of step iii) to be performed in the same reaction zone, i.e. as a 'one-pot' synthesis. Thus, in such embodiments, step iii) may be commenced in the same reaction zone in which the borylated compound of Formula IIb was prepared.

In step iii) BComp is removed from the 4-position on the cytisine ring and replaced with substituent $R^1$, defined as discussed above. For the avoidance of doubt, the replacement of BComp with $R^1$ does not have to take place in a single substitution step, although this may be desirable and, as is demonstrated in the examples that follow, can be achieved.

In embodiments of the invention, in step iii) BComp may firstly be replaced with one or more intermediate $R^1$ substituents before the final $R^4$ substituent is located at the 4-position on the cytisine ring. In embodiments of the invention, the intermediate $R^1$ substituent may be a halo (e.g. bromo, chloro or iodo), benzyloxypyridine, alkyl ester (e.g. methyl ester), alkenyl (e.g. vinyl), alkynyl (acetylene), trimethylsilylacetylene, 1, 2, 3-triazol-1-yl)methyl pivalate, cyano, aminomethyl, N-Boc-aminomethyl or (benzyloxy) carbonyl)piperazin-1-yl.

For brevity, full details of how the borylated compound of Formula IIb to each of the compounds of Formula I optionally via one or more intermediate $R^1$ substituents are not provided here, as those skilled in the art will recognise and appreciate how such substitutions may be carried out. The examples which follow provide further details of reaction conditions which can be employed in this regard.

In embodiments, the process of the present invention may comprise an additional step of conducting a substitution at the $R^2$, $R^3$ and/or $R^4$ positions on the cytisine ring. For example, where substitutions at the 3- or 5-positions on the cytisine ring are required, this can be carried out. Such a step can be achieved using any techniques and reagents known to those skilled in the art. In the event that guidance is needed regarding how such substitutions can be carried out, reference is made to the examples which follow in which such steps are exemplified. Additionally or alternatively, reference can be made to Rouden et al., (Chemical Reviews, 2014, 114, pages 712 to 778) including to the articles referred to therein, which provide additional guidance in this regard.

Additionally or alternatively, in embodiments where a protecting group is located at the $R^4$ position, the process of the present invention may include the step of deprotecting the nitrogen atom at position 13- of the cytisine ring. This deprotection step may be conducted after the completion of step ii), before the commencement of step iii), during step iii) or after the completion of step iii). The skilled person will be familiar with deprotection techniques. However, in the event that any guidance in this connection is required, reference may be made to the examples which follow.

As can be seen from the foregoing, the process of the present invention advantageously, and for the first time, permits the convenient preparation of 4-substituted cytisine analogs from cytisine itself, rather than requiring a lengthy total synthesis of such compounds.

A further advantage of the present invention is that steps ii) and step iii) do not involve any chiral rearrangement of the molecule and thus, the process is stereoselective. This provides a further advantage over the art, which resulted in the formation of racemic analogs of cytisine.

Formulations, Administration and Uses

Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will be appreciated that certain of the compounds of present invention can exist in free form for treatment, or where appropriate, as a pharmaceutically acceptable derivative or a prodrug thereof. According to the present invention, a pharmaceutically acceptable derivative or a prodrug includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any salt or salt of an ester of a compound of this invention that, upon administration to a recipient, is capable of providing, either directly or indirectly, a compound of this invention or an inhibitorily active metabolite or residue thereof.

Pharmaceutically acceptable salts are well known in the art. For example, S. M. Berge, et al. describes pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^*(C_{1-4}alkyl)_4$ salts. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, micro emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polys accarides, polyethylene glycol, phospholipids or combinations thereof to impart controlled release characteristics in the composition.

PREPARATIONS AND EXAMPLES

Extraction of (-)—Cytisine from *Laburnum anagyroides* Seeds

As explained above, the process of the present invention advantageously commences from cytisine, a naturally occurring compounds which can be isolated from *laburnum* trees. While cytisine is commercially available, and those skilled in the art will be familiar with processes for extracting cytisine from natural sources, the following process is provided for completeness.

Powdered *Laburnum anagyroides* seeds (332 g), DCM (465 mL), MeOH (135 mL) and $NH_4OH$ (50 mL, 35% aq. sol.) were stirred vigorously for 3 days at r.t. with a mechanic stirrer (400 rpm). The mixture was filtered and the solids were washed with DCM (4×200 mL) until the filtrate was colourless. The filtrate was acidified with 3M HCl (330 mL) to pH 1 and the mixture was stirred for 2 h (350 rpm). The two layers were separated and the aqueous layer was slowly basified to pH 9-10 with $NH_4OH$ (70 mL, 35% aq.sol.). The mixture was stirred for 2 h, and extracted with DCM (10×70 mL). The combined organic layers were dried over $Na_2SO_4$, filtered and concentrated in vacuo yielding cytisine (4.76 g) as brown-yellow solid. Recrystallisation from toluene (5 mL) yielded (-)-cytisine (4.27 g, 1.3%) as a solid.

Addition of Protecting Group —N-Boc Cytisine (56)

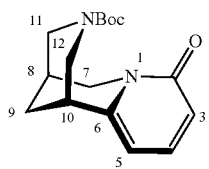

56

To a solution of (-)-cytisine (6.41 g, 33.7 mmol) and $(Boc)_2O$ (9.3 mL, 40.4 mmol) in THF (135 mL) and water (70 mL) was added an aqueous solution of $Na_2CO_3$ (4.28 g, 40.4 mmol, 1 M). The mixture was stirred for 3 days, and then diluted with EtOAc (200 mL) and brine (70 mL). The aqueous layer was extracted with EtOAc (3×150 mL) and the combined organic layers were washed with brine (150 mL), dried over $Na_2SO_4$, filtered and concentrated in vacuo. The crude reaction mixture was purified by flash column chromatography on silica gel [DCM/MeOH (3% MeOH)] to give 56 (9.10 g, 93%) as a colourless solid.

$R_f$: 0.28 [DCM/MeOH (5% MeOH)]; mp: 154-155° C. (lit: 156-157° C.); $^1$H NMR (400 MHz, $CDCl_3$, $\delta_H$): 7.26 (dd, 1H, J=9.0, 7.0 Hz, C4-H), 6.41 (d, 1H, J=9.0 Hz, C3-H), 6.04 (br s, 1H, C5-H), 4.40-4.08 (m, 3H, C7-$H_a$, C11-H, C12-H), 3.81 (dd, 1H, J=15.5, 6.5 Hz, C7-$H_b$), 3.12-2.91 (m, 3H, C11-H, C12-H, C10-H), 2.40 (br s, 1H, C8-H), 2.00-1.90 (m, 2H, C9-H), 1.31-1.20 (m, 9H, Boc); $^{13}$C NMR (100 MHz, $CDCl_3$, $\delta_C$): 163.3 (CO), 154.4/154.3 (C6, rotamers), 149.3/148.7 (CO Boc, rotamers), 138.9/138.4 (C4, rotamers), 117.0 (C3), 105.6/104.9 (C5), 80.2/79.6 (q Boc, rotamers), 51.5/50.5/49.2 (C11, C12, rotamers), 48.8 (C7), 34.8 (C10), 28.0 (3C, Boc), 27.5 (C8), 26.1 (C9). The spectroscopic properties of this compound were consistent with the data available in literature.

Removal of Protecting Group

As will be exemplified below, a wide range of 4-substituted cytisine derivatives can be prepared according to the process of the present invention. For such compounds, it may be desirable to remove the Boc protecting group. In the examples below, the Boc protecting group where present on the 4-substituted cytisine analogs was removed by one of the two following processes General Procedure A The cytisine derivative was dissolved in a solution 0.5 M HCl in MeOH (concentration of the substrate 0.1 M) and the reaction mixture was stirred for 72 h at r.t. Then, the solvent was removed in vacuo. The residue was dissolved in the minimum amount of MeOH and 10 times the MeOH volume of acetone was added slowly. The solution was stirred for 2 h. After, the precipitate was collected by filtration and washed with cold acetone.

General Procedure B

The cytisine derivative was dissolved in a solution 4.0 M HCl in dioxane (concentration of the substrate 0.1 M) and the reaction mixture was stirred for 72 h at r.t. Then, the solvent was removed in vacuo. The residue was dissolved in the minimum amount of MeOH and 10 times the MeOH volume of acetone was added slowly. The solution was stirred for 2 h. After, the precipitate was collected by filtration and washed with cold acetone.

Example 1—N-Boc 4-Bpincytisine (58)

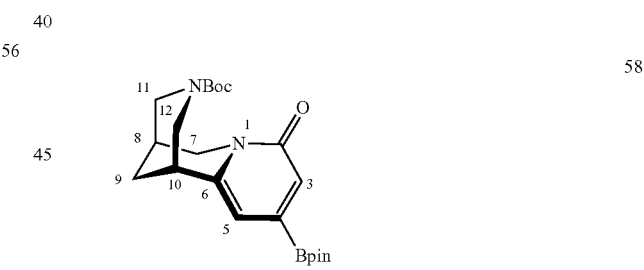

58

A Schlenk tube was charged with N-Boc-cytisine, 56 (290 mg, 1.00 mmol), bis-(iridium-cycloctadienyl-methoxide) (6.6 mg, 0.01 eq.), 4,4'-2,2'-di-tert-butylbispyridine (5.4 mg, 0.02 eq.) and bis (pinacolato)-diborane (177 mg, 0.7 eq.). The Schlenk tube was placed under vacuum and backfilled with nitrogen for three times, THF (1.4 mL) was added and the mixture was heated at 80° C. for 24 h. The mixture was cooled to r.t. and concentrated in vacuo. Although purification (see below) is possible, this was not essential; the crude reaction mixture was used in a number of subsequent conversion steps without further purification.

The crude reaction mixture was purified by flash column chromatography on silica gel [DCM/MeOH (5% MeOH)] to give 58 (180 mg, 43%; unstable compound on silica, only pure fractions collected; full conversion by $^1$H-NMR) as a pale orange foam.

$R_f$: 0.23 [DCM/MeOH (5% MeOH)]; FTIR $v_{max}$/cm$^{-1}$ (neat): 3433, 2977, 1688, 1657, 1563, 1423; $^1$H NMR (400 MHz, CDCl$_3$, $\delta_H$): 6.85 (s, 1H, C3-H), 6.31 (s, 1H, C5-H), 4.34-4.10 (m, 3H, C7-H$_a$, C12-H, C11-H), 3.80 (dd, 1H, J=15.5, 6.5 Hz, C7-H$_b$), 3.07-2.91 (m, 3H, C10-H, C11-H, C12-H), 2.41 (s, 1H, C10-H), 1.95-1.88 (m, 2H, C9-H), 1.41-1.09 (m, 23H, 12×Bpin-H, 9×Boc); $^{13}$C NMR (100 MHz, CDCl$_3$, $\delta_C$): 162.9 (CO), 154.6/154.3 (C$_6$, rotamers), 147.9/147.5 (CO Boc, rotamers), 124.4 (C3), 109.3/108.8 (C5, rotamers), 84.4 (q Boc), 82.6/80.3, 79.7/75.0 (2C, q Bpin, rotamers), 51.7/50.6/50.3/49.2 (C11, C12, rotamers), 48.9 (C7), 34.7 (C10), 28.0 (4C, Bpin), 27.5 (C8), 26.1 (C9), 24.8/24.6 (3C, Boc, rotamers), C4 non-detected; $^{11}$B NMR (96.4 MHz, CDCl$_3$, $\delta_B$): 28.94 (br s); HRMS (ESI$^+$): calculated for C$_{22}$H$_{33}$BN$_2$NaO$_5$ [M+Na]$^+$: 439.2379, found: 439.2373.

Example 2a—N-Boc4-Hydroxycytisine (66)

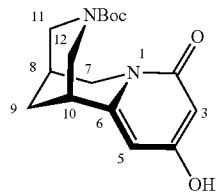

N-Boc-4-(4,4,5,5-tetramethyl-1,3,2-dioxaborolan-2-yl)-cytisine 58 was made following the general procedure for the borylation of cytisine discussed above in Example 1 in a 1.0 mmol scale.

The borylation reaction mixture was cooled to 0° C. and dissolved in THF (8.6 mL). NaOH 3 M (1.0 mL, 3.0 mmol) was added followed by a slow addition of 30% aqueous H$_2$O$_2$ (1.0 mL) over 5 min. The mixture was stirred at 0° C. for 30 min and then stirred under air at r.t. overnight. The mixture was diluted with water (3 mL) and the aqueous layer was washed with DCM (3×5 mL). The aqueous layer was acidified with 3 M HCl to pH 4-5 and extracted with DCM (5×5 mL). The combined organic layers were dried over Na$_2$SO$_4$, filtered and concentrated in vacuo. The crude reaction mixture was purified by flash column chromatography on silica gel [DCM/MeOH (5% MeOH)] to give 66 (240 mg, 79%) as an off-white solid.

$R_f$: 0.13 [DCM/MeOH (5% MeOH)]; mp: >200° C., colourless powder; FTIR $v_{max}$/cm$^{-1}$ (neat): 2864, 1673, 1652, 1535, 1423; $^1$H NMR (400 MHz, DMSO-d$_6$, $\delta_H$): 10.27 (s, 1H, OH), 5.76 (s, 1H, C3-H), 5.45 (s, 1H, C5-H), 4.12-3.78 (m, 3H, C7-H$_a$, C11-H, C12-H), 3.51 (dd, 1H, J=15.0, 6.5 Hz, C7-H), 3.16-2.93 (m, 3H, C10-H, C11-H, C12-H), 2.29 (br s, 1H, C8-H), 1.84 (s, 2H, C9-H), 1.23-1.14 (m, 9H, Boc); $^{13}$C NMR (100 MHz, DMSO-d$_6$, $\delta_C$): 166.0 (C4), 164.2 (CO), 154.1 (C6), 150.4 (CO Boc), 98.8/98.7 (C3, rotamers), 96.3 (C5), 79.3/78.8 (q Boc, rotamers), 51.7/50.6/50.3/49.3 (C11, C12, rotamers), 48.3 (C7), 34.5 (C10), 28.1 (3C, Boc), 27.4 (C8), 25.9 (C9); HRMS (ESI$^+$): calculated for C$_{16}$H$_{23}$N$_2$O$_4$: 307.1652, found [M+H]$^+$: 307.1650, C$_{16}$H$_{22}$N$_2$NaO$_4$: 329.1472, found [M+Na]$^+$: 329.1469.

Example 2b—(+)4-Hydroxycytisine hydrochloride salt (67)

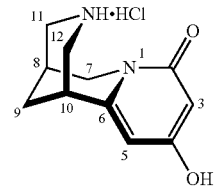

Following the general procedure A, alcohol 66 (0.79 mmol) gave alcohol 67 (184 mg, 96%) as an off-white solid.

mp: >200° C., colourless powder; $[\alpha]_D^{25}$=+3.0 [c 1.0, MeOH]; FTIR $v_{max}$/cm$^{-1}$ (neat): 3444, 2934, 2597, 1641, 1589; $^1$H NMR (400 MHz, D$_2$O, $\delta_H$): 6.33 (d, 1H, C3-H, J=2.0 Hz), 6.02 (d, 1H, C5-H, J=2.0 Hz), 4.07 (d, 1H, C7-H$_a$, J=15.5 Hz), 3.93 (dd, 1H, J=15.5, 6.5 Hz, C7-H$_b$), 3.40-3.24 (m, $\delta_H$, C10-H, C11-H, C12-H), 2.69 (br s, 1H, C8-H), 2.03-1.93 (m, 2H, C9-H); $^{13}$C NMR (100 MHz, D$_2$O, $\delta_C$): 168.4 (CO), 164.2 (C6), 149.3 (C4), 105.3 (C3), 97.2 (C5), 49.1 (C11 or C12), 49.0 (C7), 48.1 (C11 or C12), 31.5 (C10), 24.6 (C8), 22.4 (C9); HRMS (ESI$^+$): calculated for C$_{11}$H$_{15}$N$_2$O$_2$: 207.1128, found [M+H—HCl]$^+$: 207.1136.

Example 3a—N-Boc4-Methoxycytisine (68)

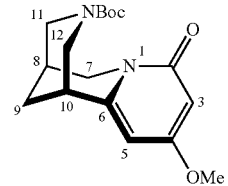

N-Boc-4-(4,4,5,5-Tetramethyl-1,3,2-dioxaborolan-2-yl)-cytisine 58 was made following the general procedure for the borylation of cytisine discussed above in Example 1 in a 0.50 mmol.

A freshly prepared solution of CuSO$_4$·5H$_2$O (37 mg, 0.15 mmol), KOH (84 mg, 1.50 mmol) and molecular sieves 4A (300 mg) in methanol (5 mL) was stirred for 5 h under nitrogen atmosphere, and then transferred over the crude of the borylation reaction using a syringe. The reaction mixture was stirred at reflux for 18 h under an oxygen atmosphere. The reaction was diluted with 10 mL of methanol, filtered through a celite pad and the solvent was removed under vacuum. The crude was distributed between ammonia solution (15 mL, 15% aq. sol.) and DCM (15 mL), and the aqueous phase was extracted with DCM (4×15 mL). The organic phases were combined, dried over MgSO$_4$, filtered and concentrated. Purification of the crude reaction mixture by flash column chromatography [DCM/MeOH, (2% MeOH)] afforded 69 (130 mg, 81%) as a colourless solid.

mp: 170-171° C., colourless needles (toluene); Rr: 0.41 [DCM/MeOH (6% MeOH)]; FTIR $v_{max}$/cm$^{-1}$(neat): 2971, 1673, 1646, 1427; $^1$H NMR (500 MHz, CDCl$_3$, $\delta_H$, 52.0° C.): 5.85 (s, 1H, C3-H), 5.79 (s, 1H, C5-H), 4.39-4.07 (m, 3H, C11-H, C12-H, C7-H), 3.82-3.74 (m, 1H, C7-H), 3.73

(s, 3H, OMe), 3.13-2.85 (m, 3H, C11-H, C12-H, C10-H), 2.38 (s, 1H, C8-H), 1.93 (m, 2H, C9-H), 1.41-1.18 (s, 9H, Boc); $^{13}$C NMR (125 MHz, CDCl$_3$, $\delta_C$, 52.0° C.): 167.4 (C4), 164.9 (CO), 154.4 (C6), 148.7 (CO Boc), 99.5 (C5), 94.8 (C3), 80.1 (q Boc), 55.1 (OMe), 50.6 (C11, C12), 48.4 (C7), 34.9 (C10), 28.1 (3C, Boc), 27.6 (C8), 26.4 (C9); HRMS (ESI$^+$): calculated for C$_{17}$H$_{25}$N$_2$O$_4$: 321.1809, found [M+H]$^+$: 321.1800; Anal. Calc. for C$_{17}$H$_{25}$N$_2$O$_4$: C, 63.73, H, 7.55, N, 8.74. Found C, 64.15, H, 7.49, N, 8.77.

Example 3b—(−)4-Methoxycytisine (69)

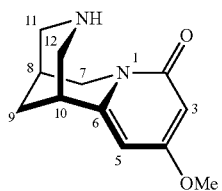

To a solution of ether 68 (130 mg, 0.42 mmol) in DCM (4 mL, 0.1 M) was added TFA (0.3 mL, 10 eq.) at once, and the reaction mixture was stirred at r.t. for 18 h. Water (10 mL) was added and the aqueous phase was washed with DCM (3×10 mL). The aqueous phase was basified with ammonia (10 mL, 15% aq. sol.) and extracted with DCM (3×10 mL). The organic phases were combined, dried over MgSO$_4$, filtered and concentrated, yielding 69 (76 mg, 85%) as a colourless solid.

mp: >200° C., colourless powder; $[\alpha]_D^{24}$=−42 [c 1.0, EtOH]; FTIR $v_{max}$/cm$^{-1}$ (neat): 2889, 1645, 1580, 1557, 1158; $^1$H NMR (500 MHz, CDCl$_3$, $\delta_H$): 5.87 (d, J=3.0 Hz, 1H, C3-H), 5.74 (d, J=3.0 Hz, 1H, C5-H), 4.10 (d, J=15.0 Hz, 1H, C7-H), 3.85 (dd, J=15.0, 6.5 Hz, 1H, C7-H), 3.77 (s, 3H, OMe), 3.14-2.98 (m, 4H, C11-H, C12-H), 2.84 (s, 1H, C10-H), 2.30 (s, 1H, C8-H), 1.96 (s, 2H, C9-H), 1.55 (s, 1H, NH); $^{13}$C NMR (125 MHz, CDCl$_3$, $\delta_C$): 167.4 (CO), 165.1 (C6), 150.6 (C4), 98.6 (C5), 94.5 (C3), 55.2 (OMe), 53.4, 53.0 (C11, C12), 49.2 (C7), 35.7 (C10), 27.7 (C8), 26.4 (C9); HRMS (ESI$^+$): calculated for C$_{12}$H$_{17}$N$_2$O$_2$: 221.1285, found [M+H]$^+$: 221.1283.

Example 4a—N-Boc4-(N-Benzylamino)cytisine (70)

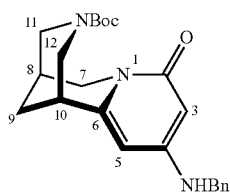

N-Boc-4-(4,4,5,5-Tetramethyl-1,3,2-dioxaborolan-2-yl)-cytisine 58 was made following the general procedure for the borylation of cytisine as detailed in Example 1 above in a 5.00 mmol scale.

In a separate vessel, Cu(OAc)·H$_2$O (300 mg, 1.5 mmol), KF (320 mg, 5.5 mmol), and molecular sieves 4A (4 g) were stirred in MeCN (20 mL) for 15-20 min. The crude of the borylation reaction was solubilised in MeCN (5 mL) and the copper solution was added via syringe to the crude reaction, stirring for 10 min. Freshly distilled BnNH$_2$ (1.1 mL, 10.0 mmol) was added and the reaction mixture was heated at reflux for 18 h under an oxygen atmosphere. The reaction mixture was cooled, filtered through Celite® and concentrated. The crude of the reaction was distributed between ammonia (25 mL, 15% aq. sol.) and DCM (25 mL) and the aqueous phase was extracted with DCM (4×25 mL). The combined organic phases were dried over MgSO$_4$, filtered and concentrated. The crude reaction mixture was purified by flash column chromatography [DCM/MeOH (2% MeOH)] affording 70 (1.70 g, 72%), together with an inseparable impurity, as a colourless solid.

$^1$H NMR (500 MHz, CDCl$_3$, $\delta_H$): 7.35-7.19 (m, $\delta_H$, Ar), 5.52 (s, 1H, C3-H), 5.46 (s, 1H, C5-H), 4.66 (s, 1H, NH), 4.38-4.11 (m, 3H, C13-H, C11-H or C12-H); 4.05 (d, J=15.5 Hz, 1H, C7-H), 3.71 (m, 1H, C7-H), 3.17-2.78 (m, 3H, 2×C11-H or C12-H, 1H×C11-H or C12-H), 2.74 (s, 1H, C10-H), 2.31 (s, 1H, C8-H), 1.96-1.80 (m, 2H, C9-H), 1.28 (s, 9H, Boc).

Example 4b—(+)4-(N-Benzylamino)cytisine (71)

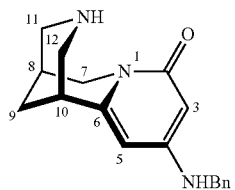

To a solution of the secondary amine 70 (1.70 g, 4.30 mmol) in DCM (43 mL, 0.1 M) was added TFA (0.4 mL, 10 eq.) and the solution was stirred at r.t. for 16 h. Water was added (20 mL) and the aqueous phase was washed with DCM (3×30 mL). Then, the aqueous phase was basified with ammonia (15 mL, 15% aq. sol.) and extracted with DCM (4×30 mL). The combined organic layers were dried over MgSO$_4$, filtered and concentrated, yielding 71 (970 mg, 76%) as a colourless solid.

R$_f$: 0.39 [DCM/MeOH (8% MeOH)]; mp: 208-211° C., (toluene); $[\alpha]_D^{25}$=+58 [c 0.5, EtOH]; FTIR $v_{max}$/cm$^{-1}$ (neat): 3266, 2919, 1637, 1559, 1533; $^1$H NMR (500 MHz, CDCl$_3$, $\delta_H$): 7.35-7.23 (m, $\delta_H$, Ar), 5.52 (s, 1H, C3-H), 5.48 (s, 1H, C5-H), 4.58 (s, 1H, NHPh), 4.26 (s, 1H, CH$_2$Ph), 4.25 (s, 1H, CH$_2$Ph), 4.03 (d, J=14.5 Hz, 1H, C7-H), 3.77 (dd, J=6.5, 14.5 Hz, 1H, C7-H), 3.09-2.93 (m, 4H, C11-H C12-H), 2.71 (s, 1H, C10-H), 2.21 (s, 1H, C8-H), 1.90 (s, 2H, C9-H), 2.07-1.71 (s, 1H, NH); $^{13}$C NMR (125 MHz, CDCl$_3$, $\delta_C$): 164.6 (CO), 154.9 (C4), 149.7 (C6), 137.8 (Ar), 128.7 (Ar, 2C), 127.5 (Ar), 127.4 (Ar, 2C), 97.2 (C5), 91.2 (C3), 53.8 (C11), 52.8 (C12), 48.7 (C7), 47.0 (CH$_2$-Ph), 35.5 (C10), 27.7 (C8), 26.5 (C9); HRMS (ESI+): calculated for C$_{18}$H$_{22}$N$_3$O: 296.1757, found [M+H]$^+$: 296.1766; Anal. Calc. for C$_{18}$H$_{21}$N$_3$O: C: 73.19, H: 7.17, N: 14.23; found C: 73.24, H: 7.18, N: 14.35.

Example 5—(−)4-(2,2,2-Trifluoroethyl)cytisine hydrochloride salt (79)

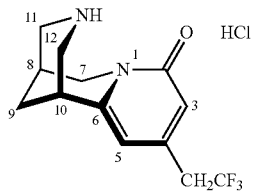

79

N-Boc-4-(4,4,5,5-Tetramethyl-1,3,2-dioxaborolan-2-yl)-cytisine 58 was made following the general procedure for the borylation of cytisine as detailed in Example 1 above in a 1.00 mmol scale.

To the crude borylation reaction mixture, [Pd$_2$(dba)$_3$] (23 mg, 1 mmol %), Xphos (47 mg, 2.5 mmol %), caesium fluoride (450 mg, 3.0 eq.) and copper (I) chloride anhydrous (99 mg, 1.0 eq.) were added, and the Schlenk tube was placed under vacuum and backfilled with nitrogen for three times. The reaction mixture was dissolved in DMF (4.0 mL, 0.25 M) and 2-iodo-1,1,1-trifluoroethane (0.19 mL, 2.0 eq.) and water (0.14 mL, 8.0 eq.) were added. The reaction mixture was stirred at 65° C. for 18 h. The solvent was removed in vacuo and the reaction crude distributed between EtOAc (15 mL) and water (15 mL). The aqueous phase was extracted with EtOAc (3×15 mL). The organic phases were combined, dried over MgSO$_4$, filtered and concentrated. Purification of the crude reaction mixture by flash column chromatography [DCM/MeOH (2% MeOH)] afforded N-Boc-4-(2,2,2-trifluoroethyl)-cytisine (190 mg, 50%) as a colourless solid. The resulting trifluoro-cytisine derivative was deprotected and converted into its HCl salt following the general procedure A yielded ligand 79 (93 mg, 34%) as a colourless solid.

mp: >200° C., colourless powder; $[\alpha]_D^{26}$=−42 [c 0.5, MeOH]; FTIR v$_{max}$/cm$^{-1}$ (neat): 2723, 1640, 1563, 1467, 1458; $^1$H NMR (500 MHz, D$_2$O, $\delta_H$): 6.61-6.55 (m, 2H, C3-H, C5-H), 4.14-3.88 (m, 2H, C7-H), 3.5-3.26 (m, 7H, C10-H, C11-H, C12-H, CH$_2$—CF$_3$), 2.75 (s, 1H, C8-H), 2.15-1.95 (m, 2H, C9-H); $^{13}$C NMR (125 MHz, D$_2$O, $\delta_C$): 164.5 (CO), 147.0 (C6), 145.3 (C4), 125.0 (d, J=276 Hz, CF$_3$), 118.4, 111.4 (C3, C5), 49.4, 48.2 (C11, C12), 48.6 (C7), 38.3 (q, J=30.0 Hz, C14), 31.4 (C10), 24.7 (C8), 22.5 (C9); $^{19}$F NMR (376 MHz, D$_2$O, $\delta_F$): −64.5 (t, 11.0 Hz); HRMS (ESI$^+$): calculated for C$_{13}$H$_{16}$F$_3$N$_2$O: 273.1209, found [M+H—HCl]$^+$: 273.1220.

Example 6—(−)4-(Perfluorophenyl)cytisine hydrochloride salt (75)

75

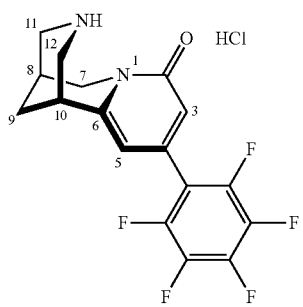

N-Boc-4-(4,4,5,5-Tetramethyl-1,3,2-dioxaborolan-2-yl)-cytisine 58 was made following the general procedure for the borylation of cytisine detailed in Example 1 above in a 1.00 mmol scale.

Bromopentafluorobenzene (0.15 mL, 1.2 eq.), PdCl$_2$(PPh$_3$)$_2$ (35 mg, 0.05 eq.) and Cs$_2$CO$_3$ (410 mg, 2.5 eq.) were added over the crude of the borylation reaction and the reaction mixture was dissolved in THF (5 mL, 0.2 M) and stirred at 80° C. for 18 h. The reaction mixture was diluted with ammonia (25 mL, 15% aq. sol.), and the aqueous phase was extracted with EtOAc (4×25 mL). The combined organic phases were dried over MgSO$_4$, the solids were filtered off and the solvent was evaporated in vacuo. Purification of the crude reaction mixture by flash column chromatography [DCM/MeOH (1.5% MeOH)] yielded 74 (509 mg, 99%) as a colourless solid. (Contaminated with [PdCl$_2$(PPh$_3$)$_2$]).

$^1$H NMR (500 MHz, CDCl$_3$, $\delta_H$): 6.53 (s, 1H, C3-H), 6.09 (s, 1H, C5-H), 4.49-4.12 (m, 3H, C11-H C12-H C7-H), 3.88 (dd, J=16.5, 6.5 Hz, 1H, C7-H), 3.18-2.96 (m, 3H, C11-H C12-H C8-H), 2.47 (s, 1H, C10-H), 2.02 (m, 2H, C9-H), 1.29 (s, 9H, Boc).

Following the general procedure A, N-Boc protected cytisine derivative 74 (1.1 mmol) gave 4-(perfluorophenyl)-cytisine hydrochloride salt 75 (160 g, 43%) as a colourless solid.

mp: >200° C., colourless powder; $[\alpha]_D^{26}$=−16 [c 0.5, MeOH]; FTIR v$_{max}$/cm$^{-1}$ (neat): 2977, 2869, 1658, 1536; $^1$H NMR (500 MHz, MeOH, $\delta_H$): 6.58 (s, 1H, C3-H), 6.43 (s, 1H, C5-H), 4.13 (d, J=15.5 Hz, 1H, C7-H), 4.00 (dd, J=6.0, 15.0 Hz, 1H, C7-H), 3.14-2.99 (m, $\delta_H$, C11-H C12-H C10-H), 2.43 (s, 1H, C8-H), 2.07 (m, 2H, C9-H); $^{13}$C NMR (125 MHz, MeOH, 5c): 163.7 (CO), 152.4 (C4), 144.9 (m), 143.1 (m), 142.2 (m), 140.2 (m), 138.8 (m), 136.7 (m) (6C, Ar), 138.5 (C6), 117.0 (C3), 107.4 (C5), 52.6, 51.6 (C11, C12), 49.8 (C7), 35.2 (C10), 27.4 (C8), 25.2 (C9); $^{19}$F NMR (376 MHz, D$_2$O, $^6$F): −140.7, −141.3, −152.9, −160.8, −161.1; HRMS (ESI$^+$): calculated for C$_{17}$H$_{14}$F$_5$N$_2$O: 357.1021, found [M+H$^+$—HCl]$^+$: 357.1017.

Example 7a—N-Boc4-(2-Pyridinyl)cytisine (100)

100

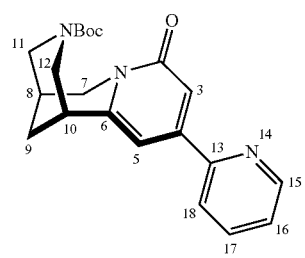

N-Boc-4-(4,4,5,5-Tetramethyl-1,3,2-dioxaborolan-2-yl)-cytisine 58 was made following the general procedure for the borylation of cytisine as detailed above in Example 1 in a 1.00 mmol scale.

Anhydrous Cs$_2$CO$_3$ (814 mg, 2.5 mmol) and PdCl$_2$(PPh$_3$)$_2$ (35 mg, 5 mol %) were added over the borylation reaction crude mixture. Dry THF (10 mL) was added followed by 2-bromopyridine (115 μL, 1.2 mmol). The mixture was stirred at 80° C. for 48 h. The reaction was cooled to r.t., diluted with EtOAc (50 mL) and filtered through Celite.® The organic layer was washed with water (10 mL), brine (10 mL), dried over Na$_2$SO$_4$, filtered and concentrated in vacuo. The crude was purified by flash column chromatography on silica gel [DCM/MeOH (4% MeOH)+0.1% ammonia (15% aq. sol.)] to give 100 (205 mg, 56%) as a yellow oil. The product was used in the next step without any further purification.

$R_f$: 0.17 [DCM/MeOH (5% MeOH)]; $^1$H NMR (400 MHz, CDCl$_3$, $\delta_H$): 8.65 (d, 1H, J=2.0 Hz, C15-H), 7.75-7.68 (m, 2H, C17-H, C18-H), 7.29-7.26 (m, 1H, C16-H), 6.92 (s, 1H, C3-H), 6.86 (s, 1H, C5-H), 4.37-4.17 (m, 3H, C7-H$_a$, C11-H, C12-H), 3.84 (dd, 1H, J=6.5, 15.5 Hz, C7-H$_b$), 3.11-2.96 (m, 3H, C10-H, C11-H, C12-H), 2.42 (s, 1H, C8-H), 2.01-1.92 (m, 2H, C9-H), 1.30-1.13 (m, 9H, Boc); $^{13}$C NMR (100 MHz, CDCl$_3$, $\delta_C$): 163.7 (CO), 154.5 (CO Boc), 154.2 (C6), 149.6 (C4), 148.8 (C13), 145.4 (C16), 136.9 (C17), 123.8 (C16), 121.1 (C18), 113.8 (C3), 104.4/103.9 (C5, rotamers), 80.3/79.8 (q Boc, rotamers), 51.6/50.6/50.3/49.3 (C11, C12, rotamers), 48.9 (C7), 35.1 (C10), 27.5 (C8), 26.2 (C9), 24.8 (3C, Boc); HRMS (ESI$^+$): calculated for C$_{21}$H$_{26}$N$_3$O$_3$ [M+H]$^+$: 368.1969, found: 368.1965; calculated for C$_{21}$H$_{25}$N$_3$NaO$_3$: 390.1788, found [M+Na]$^+$: 390.1784.

Example 7b—(−)4-(2-Pyridinyl)cytisine dihydrochloride salt (101)

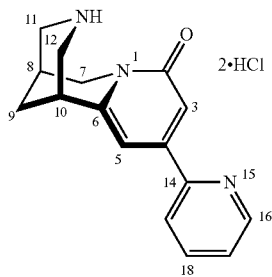

101

Following the general procedure A for the deprotection of cytisine, N-Boc-4-(2-Pyridinyl)-cytisine 100 (0.55 mmol) gave 101 (99.2 mg, 63%) as a colourless solid.

mp: >200° C., colourless powder; [α]$_D^{24}$=−12 [c 1.0, MeOH]; FTIR v$_{max}$/cm$^{-1}$ (neat): 3471, 2750, 1658, 1572; $^1$H NMR (400 MHz, D$_2$O, $\delta_H$): 8.71-8.70 (m, 1H, C16-H), 8.53-8.49 (m, 1H, C18-H), 8.16 (d, 1H, J=8.0 Hz, C19-H), 7.97-7.94 (m, 1H, C17-H), 6.89 (d, 1H, J=2.0 Hz, C3-H), 6.84 (s, 1H, J=2.0 Hz, C5-H), 4.11 (d, 1H, J=16.0 Hz, C7-H$_a$), 3.98 (dd, 1H, J=6.5, 16.0 Hz, C7-H$_b$), 3.52 (br s, 1H, C10-H), 3.45-3.30 (m, 4H, C11-H, C12-H), 2.77 (br s, 1H, C10-H), 2.10-2.00 (m, 2H, C9-H); $^{13}$C NMR (100 MHz, D$_2$O, $\delta_C$): 164.3 (CO), 149.3 (C6), 148.7 (C4), 146.9 (Ar py), 143.3 (Ar py), 142.7 (Ar py), 127.3 (Ar py), 126.2 (Ar py), 116.4 (C3), 107.0 (C5), 49.3, 49.0 (C11, C12), 48.2 (C7), 31.8 (C8), 24.7 (C10), 22.4 (C9); HRMS (ESI$^+$): calculated for C$_{16}$H$_{18}$N$_3$O: 268.1444, found [M+H-2HCl]$^+$: 268.1444.

Example 8—(−)4-(3-Pyridinyl)cytisine dihydrochloride salt (104)

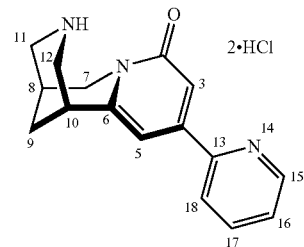

104

A Schlenk tube was charged with N-Boc-4-bromo-cytisine 61 (370 mg, 1.0 mmol), [Pd$_2$(dba)$_3$] (9.0 mg, 1 mmol %), tricyclohexylphosphine (7.0 mg, 2.4 mmol %) and 3-pyridinylboronic acid (140 mg, 1.1 eq.), and placed under vacuum and backfilled with nitrogen three times. The mixture was dissolved in dioxane (2.6 mL, 0.4 M) and a solution of tripotassium phosphate in water (360 g, 1.7 eq., 1.3 M) was added dropwise with a syringe over 10 min. The reaction mixture was heated at 100° C. for 18 h. The solution was filtered through celite and the solvent was removed in vacuo. Ammonia solution (5 mL, 15% aq. sol.) was added and the aqueous phase was extracted with DCM (4×25 mL). The combined organic phases were dried over MgSO$_4$, filtered and concentrated. The resulting N-Boc-4-(3-pyridinyl)-cytisine derivative was deprotected and converted into the HCl salt following the general procedure A yielding 104 (210 mg, 78%) as a colourless solid.

mp: >200° C., colourless powder; [α]$_D^{24}$=−11 [c 1.0, MeOH]; FTIR v$_{max}$/cm$^{-1}$ (neat): 2926, 2528, 2072, 1650, 1539; $^1$H NMR (500 MHz, MeOD, $\delta_H$): 9.39 (s, 1H, Ar Py), 9.07 (s, 1H, Ar Py), 9.01 (s, 1H, Ar Py), 8.27 (s, 1H, Ar Py), 7.10 (s, 1H, C3-H), 7.06 (s, 1H, C5-H), 4.35 (d, 1H, J=15.5 Hz, C7-H), 4.14 (dd, 1H, J=15.5, 6.0 Hz, C7-H), 3.69-3.53 (m, $\delta_H$, C11-H C12-H C10-H), 2.89 (s, 1H, C8-H), 2.28 (d, J=13.5 Hz, 1H, C9-H), 2.17 (d, 1H, J=13.5 Hz, C9-H); $^{13}$C NMR (125 MHz, MeOD, 6c): 163.6 (CO), 148.9 (C6), 145.3 (q Py), 144.9 (Py), 141.7 (Py), 140.2 (Py), 136.7 (C4), 127.7 (Py), 115.0 (C5), 107.1 (C3), 49.1, 48.5 (C11, C12), 48.9 (C7), 32.0 (C10), 25.2 (C8), 22.7 (C9); HRMS (ESI$^+$): calculated for C$_{16}$H$_{18}$N$_3$O: 268.1444, found [M+H-2HCl]$^+$: 268.1444.

Example 9a—(−)N-Boc4-(4-Pyridinyl)cytisine (102)

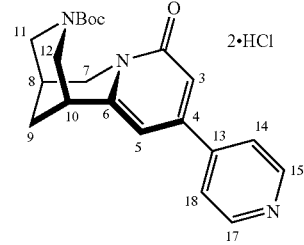

102

N-Boc-4-(4,4,5,5-Tetramethyl-1,3,2-dioxaborolan-2-yl)-cytisine 58 was made following the general procedure for the borylation of cytisine detailed in Example 1 above in a 1.00 mmol scale.

Anhydrous $Cs_2CO_3$ (814 mg, 2.5 mmol) and $PdCl_2(PPh_3)_2$ (35 mg, 5 mol %) were added over the crude borylation reaction mixture. Dry THF (10 mL) was added followed by 4-iodopyridine (246 mg, 1.2 mmol). The mixture was stirred at 80° C. for 48 h. The mixture was cooled to r.t., diluted with EtOAC (50 mL) and filtered through Celite.® The organic layer was washed with brine (10 mL), dried on $Na_2SO_4$, filtered and concentrated in vacuo. The crude mixture was purified by flash column chromatography on silica gel [DCM/MeOH (5% MeOH)+0.1% ammonia (15% aq. sol.) to give 102 (312 mg, 85%) as an orange oil. The product was used in the next step without any further purification.

$R_f$: 0.39 [DCM/MeOH (10% MeOH)]; $^1H$ NMR (400 MHz, $CDCl_3$, $\delta_H$): 8.63 (d, 2H, J=6.0 Hz, C15-H, C17-H), 7.41 (d, 2H, J=6.0 Hz, C14-H, C18-H), 6.66 (s, 1H, C3-H), 6.28 (s, 1H, C5-H), 4.38-4.15 (m, 3H, C7-$H_a$, C11-H, C12-H), 3.82 (dd, 1H, J=6.5, 15.5 Hz, C7-$H_b$), 3.06 (br s, 3H, C10-H, C11-H, C12-H), 2.42 (br s, 1H, C8-H), 2.02-1.93 (m, 2H, C9-H), 1.30-1.13 (m, 9H, Boc); $^{13}C$ NMR (100 MHz, $CDCl_3$, $\delta_C$): 163.3 (CO), 154.5/154.2 (CO Boc, rotamers), 150.4 (C15, C17), 149.6 (C6), 148.0/147.8 (C4, rotamers), 145.2 (C13), 121.1 (C14, C18), 114.4 (C3), 104.3/103.5 (C5, rotamers), 80.5/79.8 (q Boc, rotamers), 51.7/50.6/50.3/49.3 (C11, C12, rotamers), 49.0 (C7), 35.1 (C10), 27.4 (C8), 26.1 (C9), 24.8 (3C, Boc); HRMS (ESI+): calculated for $C_{21}H_{26}N_3O_3$: 368.1969, found [M+H]+: 368.1970, calculated for $C_{21}H_{25}N_3NaO_3$: 390.1788, found [M+Na]+: 390.1791.

Example 9b—(−)4-(4-Pyridinyl)cytisine dihydrochloride salt (103)

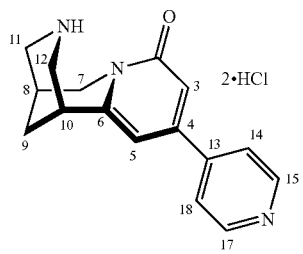

103

Following the general procedure A, N-Boc4-(4-pyridinyl)cytisine 102 (0.85 mmol) gave 103 (122 mg, 48%) as a pale-orange solid.

mp: >200° C., colourless powder; $[\alpha]_D^{24}$=−12 [c 0.5, water]; FTIR $v_{max}/cm^{-1}$ (neat): 2590, 1653 (w), 1631, 1579, 1545; $^1H$ NMR (400 MHz, $D_2O$, $\delta_H$): 8.75 (d, 2H, J=6.5 Hz, C14-H, C18-H), 8.20 (d, 2H, J=6.5 Hz, C15-H, C17-H), 6.90 (d, 1H, J=2.0 Hz, C3-H), 6.86 (s, 1H, J=2.0 Hz, C5-H), 4.10 (d, 1H, J=16.0 Hz, C7-$H_a$), 3.97 (dd, 1H, J=6.5, 16.0 Hz, C7-$H_b$), 3.51 (s, 1H, C10-H), 3.45-3.28 (m, 4H, C11-H, C12-H), 2.76 (br s, 1H, C8-H), 2.09-1.99 (m, 2H, C9-H); $^{13}C$ NMR (100 MHz, $D_2O$, $\delta_C$): 164.5 (CO), 154.3 (C4), 148.7 (C6), 146.7 (C13), 141.6 (2C, C15, C17), 125.2 (2C, C14, C17), 116.3 (C3), 107.4 (C5), 49.4 (C11 or C12), 48.9 (C7), 48.2 (C11 or C12), 31.8 (C10), 24.7 (C8), 22.5 (C9); HRMS (ESI+): calculated for $C_{16}H_{18}N_3O$: 268.1444, found [M+H]+: 268.1453.

Example 10a—N-Boc4-(4-(2-Benzyloxy)pyridine)cytisine 105

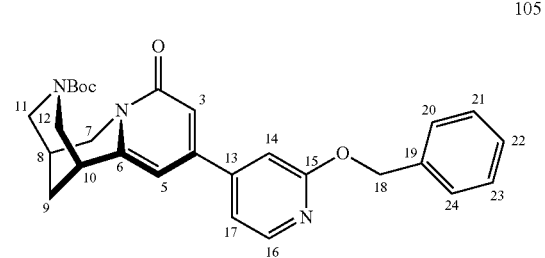

105

N-Boc-4-(4,4,5,5-Tetramethyl-1,3,2-dioxaborolan-2-yl)-cytisine 58 was made following the general procedure for the borylation of cytisine detailed above in Example 1 in a 1.00 mmol scale.

Anhydrous $Cs_2CO_3$ (814 mg, 2.5 mmol) and $PdCl_2(PPh_3)_2$ (35 mg, 5 mol %) were added over the crude borylation reaction mixture. Dry THF (5.0 mL) was added followed by a solution of 4-bromo-2-benzyloxypyridine (316 mg, 1.2 mmol) in dry THF (5.0 mL). The mixture was stirred at 80° C. for 48 h. The solution was cooled to r.t., diluted with EtOAc (50 mL) and filtered through Celite®. The organic layer was washed with water (10 mL), brine (10 mL), dried over $Na_2SO_4$, filtered and concentrated in vacuo. The crude reaction mixture was purified by flash column chromatography on silica gel [DCM/MeOH (4% MeOH)+0.1% ammonia (15% aq. sol.)] to give 105 (485 mg, 99%) with few impurities as a pale yellow oil. The product was used in the next step without any further purification.

$R_f$: 0.23 [DCM/MeOH (5% MeOH)]; $^1H$ NMR (400 MHz, $CDCl_3$, $\delta_H$): 8.22 (d, 1H, J=5.0 Hz, C16-H), 7.46 (d, 2H, J=7.0 Hz, C20-H, C24-H), 7.39-7.29 (m, 3H, C21-H, C22-H, C23-H), 7.04 (d, 1H, J=5.0 Hz, C17-H), 6.96 (s, 1H, C14-H), 6.67 (s, 1H, C3-H), 6.27 (s, 1H, C5-H), 5.41 (s, 2H, C18-H), 4.40-4.18 (m, 3H, C7-$H_a$, C11-H, C12-H), 3.84 (dd, 1H, J=6.5, 15.5 Hz, C7-$H_b$), 3.05 (s, 3H, C10-H, C11-H, C12-H), 2.44 (s, 1H, C8-H), 2.03-1.94 (m, 2H, C9-H), 1.33-1.17 (m, 9H, Boc); $^{13}C$ NMR (100 MHz, $CDCl_3$, $\delta_C$): 164.4 (C15), 163.4 (CO), 154.7/154.4 (CO Boc, rotamers), 150.0, 149.5 (C6, C4), 148.3, 147.7 (C13, C16), 137.2 (C19), 128.6, 128.1, 128.0 (5C, C20, C21, C22, C23, C24), 114.9, 114.5 (C3, C17), 108.9/108.7 (C14, rotamers), 104.4/103.7 (C5, rotamers), 80.5/79.9 (q Boc, rotamers), 68.0 (C18), 51.8/50.7/50.5/49.4 (C11, C12, rotamers), 49.0 (C7), 35.3 (C10), 28.2 (3C, Boc), 27.6 (C8), 26.3 (C9); HRMS (ESI+): calculated for $C_{28}H_{32}N_3O_4$: 474.2387, found [M+H]+: 474.2383, calculated for $C_{28}H_{31}N_3NaO_4$: 496.2207, found [M+Na]+: 496.2198.

Example 10b—(+)4-(4-(2-Pyridone))cytisine hydrochloride salt (106)

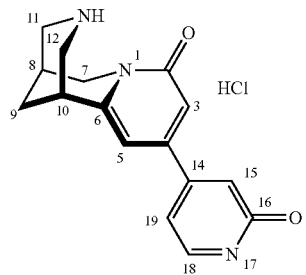

To a solution of N-Boc 4-(4-(2-benzyloxy)pyridine)cytisine 105 (448 mg, 0.95 mmol) in MeOH (5.7 mL) was added HCl (2.9 mL, conc. aq. sol.). The mixture was heated at reflux for 24 h. After cooling to r.t., the solvent was removed in vacuo. The crude was solubilized in MeOH (55 mL) and acetone (550 mL) was added. The mixture was stirred for 2 h. The solids were filtered, washed with acetone and dried to give 106 (254 mg, 84%) as a pale yellow solid.

mp: >200° C., colourless powder; $[\alpha]_D^{23}$=+26 [c 0.5, water]; FTIR $v_{max}$/cm$^{-1}$ (neat): 2946, 2732, 2582, 1638, 1567; $^1$H NMR (400 MHz, D$_2$O, $\delta_H$): 7.56 (d, 1H, J=6.5 Hz, C18-H), 6.77-6.64 (m, 4H, C3-H, C5-H, C15-H, C19-H), 4.19 (d, 1H, J=15.5 Hz, C7-H$_a$), 4.00 (dd, 1H, J=5.5, 15.5 Hz, C7-H$_b$), 3.56-3.34 (m, $\delta_H$, C10-H, C11-H, C12-H), 2.89 (s, 1H, C8-H), 2.23-2.09 (m, 2H, C9-H); $^{13}$C NMR (100 MHz, D$_2$O, $\delta_C$): 164.3 (C16), 164.0 (CO), 150.4 (C14), 148.4 (C4), 147.8 (C6), 135.4 (C18), 116.3, 114.3 (C15, C19), 107.2 (C3), 106.9 (C5), 49.3 (C11 or C12), 48.7 (C7), 48.2 (C11 or C12), 31.6 (C10), 24.7 (C8), 22.5 (C9); HRMS (ESI$^+$): calculated for C$_{16}$H$_{17}$N$_3$O$_2$: 284.1394, found [M+H—HCl]$^+$: 284.1386.

Example 11—(−)N-Boc 4-Chlorocytisine (59)

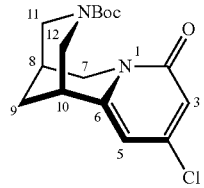

N-Boc-4-(4,4,5,5-Tetramethyl-1,3,2-dioxaborolan-2-yl)-cytisine 58 was made following the general procedure for the borylation of cytisine outlined in Example 1 above in a 1.00 mmol scale.

The borylation reaction crude mixture was solubilized in MeOH (2.5 mL). A solution of CuCl$_2$ (470 mg, 3.5 mmol) in H$_2$O (2.5 mL) was added and the mixture was stirred at r.t. for 4 days under air. The mixture was diluted with NH$_4$OH (10 mL, 15% aq.sol.) and the aqueous phase was extracted with DCM (3×10 mL). The combined organic layers were dried over Na$_2$SO$_4$, filtered and concentrated in vacuo. The crude was purified by flash column chromatography on silica gel [EtOAc] to give 59 (247 mg, 76%) as an off-white solid.

R$_f$: 0.21 [EtOAc]; mp: 148-149° C. (toluene); FTIR $v_{max}$/cm$^{-1}$ (neat): 2976, 2925, 1678, 1639, 1539; $^1$H NMR (400 MHz, CDCl$_3$, 5H): 6.43 (s, 1H, C3-H), 6.08 (s, 1H, C5-H), 4.34-4.07 (m, 3H, C7-H$_a$, C11-H, C12-H), 3.74 (dd, 1H, J=6.5, 15.5 Hz, C7-H$_b$), 3.12-2.94 (m, 3H, C10-H, C11-H, C12-H), 2.40 (s, 1H, C8-H), 1.90 (s, 2H, C9-H), 1.31-1.22 (m, 9H, Boc); $^{13}$C NMR (100 Hz, CDCl$_3$, $\delta_C$): 162.5 (CO), 154.5/154.2 (CO Boc, rotamers), 149.9/149.4 (C4, rotamers), 146.1/145.8 (C6, rotamers), 115.7 (C3), 107.1/106.4 (C5, rotamers), 80.5/80.0 (q Boc, rotamers), 51.5/50.5/50.1/49.2 (C11, C12, rotamers), 48.9 (C7), 34.8 (C10), 28.0 (3C, Boc), 27.4 (C8), 26.0 (C9); HRMS (ESI+): calculated for C$_{16}$H$_{22}$ClN$_2$O$_3$: 325.1313, found [M+H]$^+$: 325.1301, calculated for C$_{16}$H$_{21}$ClN$_2$NaO$_3$: 347.1133, found [M+Na]$^+$: 347.1121.

Example 12—(−)4-Chlorocytisine (60)

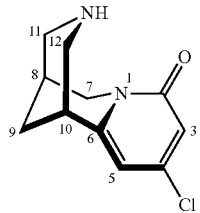

N-Boc-4-(4,4,5,5-Tetramethyl-1,3,2-dioxaborolan-2-yl)-cytisine 58 was made following the general procedure for the borylation of cytisine as outlined above in Example 1 in a 1.00 mmol scale.

In a sealed tube, the borylation reaction crude mixture was solubilized in MeOH (2.5 mL) and an aqueous solution of CuCl$_2$ (470 mg, 3.5 mmol, 1.4 M) was added. The reaction was stirred at 90° C. for 18 h. The reaction was coded, diluted with NH$_4$OH (5 mL, 15% aq.sol.) and the aqueous phase was extracted with DCM (5×5 mL). The combined organic layers were concentrated in vacuo. The residue was partitioned between 3M HCl (5 mL) and DCM (5 mL). The aqueous layer was washed with DCM (2×5 mL), basified with concentrated NH$_4$OH to pH 10 and extracted with DCM (5×5 mL). The combined organic layers were dried on Na$_2$SO$_4$, filtered and concentrated in vacuo. The crude reaction mixture was purified by flash column chromatography on silica gel [DCM/MeOH/ammonia (89:10:1)] to give 60 (179 mg, 80%) as an off-white solid. A high purity sample was obtained by recrystallization in toluene.

R$_f$: 0.22 [DCM/MeOH (10% MeOH)]; mp: 167-168° C., colourless solid (toluene); $[\alpha]_D^{25}$=−32 [c 1.0, EtOH]; FTIR $v_{max}$/cm$^{-1}$ (neat): 3330, 3064, 2930, 2793, 1634, 1538; $^1$H NMR (400 MHz, CDCl$_3$, $\delta_H$): 6.45 (d, 1H, J=2.0 Hz, C3-H), 6.02 (d, 1H, J=2.0 Hz, C5-H), 4.03 (d, 1H, J=15.5 Hz, C7-H$_a$), 3.82 (dd, 1H, J=6.5, 15.5 Hz, C7-H$_b$), 3.07-2.85 (m, 4H, C11-H, C12-H), 2.85 (s, 1H, C10-H), 2.31 (s, 1H, C8-H), 1.92 (s, 2H, C9-H), 1.36 (s, 1H, NH); $^{13}$C NMR (100 MHz, CDCl$_3$, $\delta_C$): 162.7 (CO), 151.8 (C4), 146.0 (C6), 115.2 (C3), 106.3 (C5), 53.7, 52.9 (C11, C12), 49.8 (C7), 35.6 (C10), 27.5 (C8), 26.2 (C9); HRMS (ESI$^+$): calculated for C$_{11}$H$_{14}$ClN$_2$O: 225.0789, found [M+H]$^+$: 225.0791. Anal. Calc. for C$_{11}$H$_{13}$ClN$_2$O: theor. C=58.80, H=5.83, N=12.47, found C=58.40, H=5.86, N=12.32.

Example 13a—(−)N-Boc 4-Iodocytisine (64)

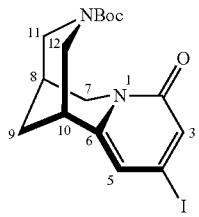

N-Boc-4-(4,4,5,5-Tetramethyl-1,3,2-dioxaborolan-2-yl)-cytisine 58 was made following the general procedure for the borylation of cytisine as detailed in Example 1 above in a 5.00 mmol scale.

$Cu(NO_3)_2 \cdot 3H_2O$ (2.42 g, 10.0 mmol), $NH_4I$ (1.45 g, 10.0 mmol) and sieves molecules 4 Å (500 mg) were added over the crude borylation reaction mixture, and the Schlenk flask was placed under nitrogen and backfilled with oxygen for three times. The reaction mixture was dissolved in DMF (25 mL) and heated at 80° C. for 24 h. The solvent was removed in vacuo and the residue was dissolved in DCM. The mixture was poured over ammonia (30 mL, 15% aq. sol.) and the aqueous phase was extracted with DCM (4×25 mL). The combined organic layers were dried on $MgSO_4$, filtered and concentrated, and the crude was purified by flash column chromatography [DCM/MeOH (2% MeOH)]) yielding iodide 64 (1.99 g, 95%) as an off-yellow solid.

$R_f$: 0.21 [DCM:MeOH (3% MeOH)]; mp: 139-140° C., needles (toluene); FTIR $v_{max}$/cm$^{-1}$(neat): 2920, 1679, 1632, 1523; $^1$H NMR (500 MHz, CDCl$_3$, δ$_H$, 52.0° C.): 6.90 (d, J=2.0 Hz, 1H, C3-H), 6.37 (d, J=2.0 Hz, 1H, C5-H), 4.39-4.04 (m, 3H, C11-H, C12-H, C7-H), 3.72 (dd, J=16.0, 7.0 Hz, 1H, C7-H), 3.09-2.93 (m, 2H, C11-H, C12-H), 2.89 (s, 1H, C10-H), 2.39 (s, 1H, C8-H), 1.99-1.87 (m, 2H, C9-H), 1.26 (s, 9H, Boc); $^{13}$C NMR (125 MHz, CDCl$_3$, δc, 52.0° C.): 161.6 (CO), 154.3 (CO Boc), 148.8 (C6), 126.3 (C3), 114.3 (C5), 108.2 (C4), 80.1 (q Boc), 50.4, 49.3 (C11, C12), 48.8 (C7), 34.5 (C10), 28.1 (3C, Boc), 27.5 (C8), 26.1 (C9); HRMS (ESI$^+$): calculated for C$_{16}$H$_{22}$IN$_2$O$_3$: 417.0670, found [M+H]$^+$: 417.0672; calculated for C$_{16}$H$_{21}$IN$_2$NaO$_3$: 439.0489, found [M+Na]$^+$: 439.0491.

Example 13b—(+)4-Iodocytisine hydrochloride salt (65)

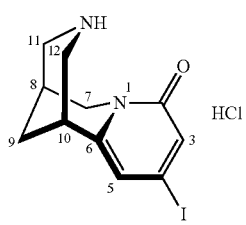

Following the general procedure A, N-Boc 4-Iodocytisine 64 (0.68 mmol) gave 65 (0.18 g, 86%) as a colourless solid.

mp: >200° C., colourless powder; [α]$_D^{21}$=+12 [c 1.0, water]; FTIR $v_{max}$/cm$^{-1}$ (neat): 2714, 1615, 1551, 1455; $^1$H NMR (500 MHz, D$_2$O, δ$_H$): 7.07 (s, 1H, C3-H), 6.89 (s, 1H, C5-H), 4.03 (d, J=15.5 Hz, 1H, C7-H), 3.88 (dd, J=15.5, 6.0 Hz, 1H, C7-H), 3.44 (s, 1H, C10-H), 3.41-3.29 (m, 4H, C11-H C12-H), 2.76 (s, 1H, C8-H), 2.08-1.98 (m, 2H, C9-H); 13C NMR (125 MHz, D$_2$O, δ$_C$): 163.3 (CO), 146.8 (C6), 126.4 (C3), 118.9 (C5), 110.7 (C4), 49.3, 48.2 (C11, C12), 48.7 (C7), 31.0 (C10), 24.7 (C8), 22.4 (C9); HRMS (ESI$^+$): calculated for C$_{11}$H$_{14}$IN$_2$O: 317.0145, found [M+H$^+$—HCl]$^+$: 317.0141.

Example 14a—(−)N-Boc 4-Trifluoromethylcytisine (76)

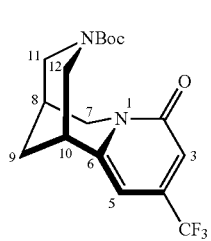

A Schlenk flask was charged with N-Boc 4-iodocytisine 64 (2.08 g, 5 mmol), copper iodide (4.52 g, 23.7 mmol), potassium fluoride anhydrous (1.38 g, 23.7 mmol) and trimethyl (trifluoromethyl)silane (3.5 mL, 23.7 mmol) and the reaction mixture was placed under nitrogen. DMF (24 mL, 0.2 M) was added and the reaction mixture was stirred at 50° C. for 16 h. The solvent was removed in vacuo and the residue distributed between DCM (20 mL) and ammonia (20 mL, 15% aq.sol.). The aqueous phase was extracted with DCM (3×20 mL) and the combined organic phases were dried over MgSO$_4$, the solids were filtered off and the solvent was evaporated in vacuo. Purification of the crude of the reaction by flash column chromatography [EtOAc/n-Hexane (4:1)] yielded 76 (1.52 g, 85%) as a colourless solid.

mp: 150-151° C., colourless solid (toluene); FTIR $v_{max}$/cm$^{-1}$ (neat): 2981, 1680, 1664, 1547; $^1$H NMR (500 MHz, CDCl$_3$, δ$_H$): 6.73 (s, 1H, C3-H), 6.22 (s, 1H, C3-H), 4.48-4.15 (m, 3H, C11-H C12-H C7-H), 3.85 (dd, 1H, J=16.0, 6.5 Hz, C7-H), 3.22-2.95 (m, 3H, C11-H, C12-H, C8-H), 2.49 (s, 1H, C10-H), 2.02 (m, 2H, C7-H), 1.43-1.15 (m, 9H, Boc); $^{13}$C NMR (125 MHz, CDCl$_3$, δ$_C$): 162.2 (CO), 153.6 (d, J=43.0 Hz, CO Boc), 151.0 (d, J=53.0 Hz, C6), 140.5 (C4), 122.3 (d, J=273 Hz, C13), 114.1 (C3), 100.1 (d, J=83.0 Hz, C5), 80.0 (d, J=62.0 Hz, q Boc), 51.1, 50.3 (C11, C12), 49.3 (C7), 35.3 (C10), 28.0 (3C, Boc), 27.4 (C8), 26.0 (C9); $^{19}$F NMR (470 MHz, CDCl$_3$, δ$_F$): −66.5 (d, J=102 Hz); HRMS (ESI$^+$): calculated for C$_{17}$H$_{22}$F$_3$N$_2$O$_3$: 359.1577, found [M+H]$^+$: 359.1584, calculated for C$_{17}$H$_{21}$F$_3$N$_2$NaO$_3$: 381.1396, found [M+Na]$^+$: 381.1406; Anal. Calc: calculated: C, 56.9 H, 5.91 N, 7.82, found: C, 56.6, H, 5.5 N, 8.1.

Example 14b—(−)4-Trifluoromethylcytisine hydrochloride salt (77)

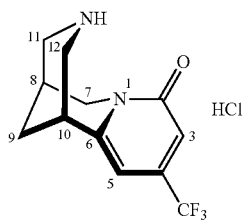

Following the general procedure A, N-Boc 4-trifluoromethylcytisine 76 (0.28 mmol) gave 77 (55 mg, 77%) as a colourless solid.

mp: >200° C.; colourless powder; $[\alpha]_D^{26}$=−66 [c 0.5, MeOH]; FTIR $v_{max}$/cm$^{-1}$ (neat): 1658, 1551, 1278, 1166, 857; $^1$H NMR (500 MHz, D$_2$O, $\delta_H$): 6.82 (s, 1H, C3-H), 6.70 (s, 1H, C5-H), 4.11 (d, 1H, J=15.5 Hz, C7-H), 3.97 (d, 1H, J=15.5, 6.5 Hz, C7-H), 3.53-3.30 (m, $\delta_H$, C11-H C12-H C10-H), 2.78 (s, 1H, C8-H), 2.05 (m, 2H, C9-H); $^{13}$C NMR (125 MHz, D$_2$O, $\delta_C$): 164.3 (CO), 149.3 (C6), 141.5 (q, J=34.0 Hz, C4), 122.2 (q, J=273.0 Hz, CF$_3$), 114.5 (C3), 104.4 (C5), 49.2, 48.9 (C11, C12), 48.2 (C7), 31.8 (C10), 24.7 (C8), 22.3 (C9); $^{19}$F NMR (376 MHz, D$_2$O, $\delta_C$, ppm): −66.2 (s); HRMS (ESI$^+$): calculated for C$_{12}$H$_{14}$F$_3$N$_2$O; 259.1053, found [M+H−HCl]$^+$: 259.1060.

Example 15a—N-Boc4-Bromocytisine (61)

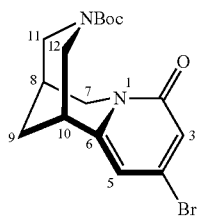

N-Boc-4-(4,4,5,5-Tetramethyl-1,3,2-dioxaborolan-2-yl)-cytisine 58 was made following the general procedure for the borylation of cytisine detailed in Example 1 above in a 5.00 mmol scale.

The borylation reaction crude mixture was solubilized in MeOH (12.5 mL) and cooled to 0° C. A solution of CuBr$_2$ (3.35 g, 15.0 mmol) in H$_2$O (12.5 mL) was added over 5 min. The ice bath was removed after 30 min and the reaction mixture was stirred at r.t. for two days in an open-air flask. The mixture was diluted with NH$_4$OH (25 mL, 15% aq.sol.) and the aqueous phase extracted with DCM (3×50 mL). The combined organic layers were dried over Na$_2$SO$_4$, filtered and concentrated in vacuo. The crude was purified by flash column chromatography on silica gel [EtOAc] to give 61 (1.54 g, 83%) as an off-white solid.

R$_f$: 0.25 [EtOAc]; mp: 163-164° C., off-white solid (toluene); FTIR $v_{max}$/cm$^{-1}$ (neat): 2976, 2924, 1679, 1635, 1531; $^1$H NMR (500 MHz, D$_2$O, $\delta_H$): 6.66 (s, 1H, C3-H), 6.21 (s, 1H, C5-H), 4.35-4.06 (m, 3H, C7-H$_a$, C11-H, C12-H), 3.73 (dd, 1H, J=6.5, 15.5 Hz, C7-H$_b$), 3.10-2.93 (m, 3H, C10-H, C11-H, C12-H), 2.40 (s, 1H, C8-H), 1.94 (s, 2H, C9-H), 1.31-1.23 (m, 9H, Boc); $^{13}$C NMR (100 MHz, CDCl$_3$, $\delta_C$): 162.2 (CO), 154.4/154.2 (CO Boc, rotamers), 149.6/149.1 (C6, rotamers) 135.1/134.6 (C4, rotamers), 119.2 (C3), 109.6/109.0 (C5, rotamers), 80.5/80.0 (q Boc, rotamers), 51.5/50.5/50.1/49.2 (C11, C12, rotamers), 48.9 (C7), 34.7 (C10), 28.0 (3C, Boc), 27.3 (C8), 26.0 (C9); HRMS (ESI$^+$): calculated for C$_{16}$H$_{22}$BrN$_2$O$_3$: 369.0808, found [M+H]$^+$: 369.0797, calculated for C$_{16}$H$_{21}$BrN$_2$NaO$_3$: 391.0628, found [M+Na]$^+$: 391.0620.

Example 15b—(−)4-Bromocytisine (62)

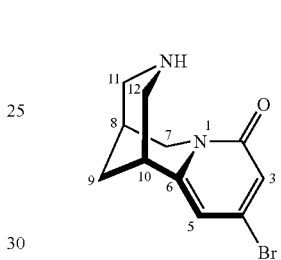

N-Boc-4-(4,4,5,5-Tetramethyl-1,3,2-dioxaborolan-2-yl)-cytisine 58 was made following the general procedure for the borylation of cytisine as detailed above in Example 1 in a 1.00 mmol scale.

The borylation reaction crude mixture was solubilized in MeOH (2.5 mL) in a sealed tube, and a solution of CuBr$_2$ (670 mg, 3.0 mmol) in H$_2$O (2.5 mL) was added. The mixture was heated at 80° C. overnight. The mixture was cooled, diluted with NH$_4$OH (5 mL, 15% aq.sol.) and extracted with DCM (5×5 mL). The combined organic layers were concentrated in vacuo. The crude was partitioned between 3M HCl (5 mL) and DCM (5 mL). The aqueous layer was washed with DCM (2×5 mL), basified with concentrated NH$_4$OH to pH 10 and extracted with DCM (5×5 mL). The combined organic layers were dried over Na$_2$SO$_4$, filtered and concentrated in vacuo. The crude was purified by flash column chromatography on silica gel [DCM/MeOH/NH$_4$OH: (89:10:1)] to give bromide 62 (228 mg, 85%) as an off-white solid. A high purity sample was obtained by recrystallization in toluene.

R$_f$: 0.21 [DCM/MeOH (10% MeOH)]; mp: 169-170° C., off-white solid (toluene); $[\alpha]_D^{25}$=−32 [c 1.0, EtOH]; FTIR $v_{max}$/cm$^{-1}$ (neat): 3335, 3061, 2934, 2791, 2741, 1622, 1531; $^1$H NMR (400 MHz, CDCl$_3$, $\delta_H$): 6.67 (d, 1H, J=2.0 Hz, C3-H), 6.17 (d, 1H, J=2.0 Hz, C5-H), 4.04 (d, 1H, J=15.5 Hz, C7-H$_a$), 3.83 (dd, 1H, J=6.5, 15.5 Hz, C7-H$_b$), 3.10-2.97 (m, 4H, C11-H, C12-H), 2.87-2.86 (m, 1H, C10-H), 2.35-2.32 (m, 1H, C8-H), 1.94 (s, 2H, C9-H), 1.46 (s, 1H, NH); $^{13}$C NMR (100 MHz, CDCl$_3$, $\delta_C$): 162.5 (CO), 151.6 (C4), 135.0 (C6), 118.7 (C3), 108.8 (C5), 53.7, 52.9 (C11, C12), 49.8 (C7), 35.7 (C10), 27.6 (C8), 26.2 (C19); HRMS (ESI$^+$): calculated for C$_{11}$H$_{14}$BrN$_2$O: 269.0284, found [M+H]$^+$: 269.0289.

Example 16a—N-Boc 4-aminocytisine (80)

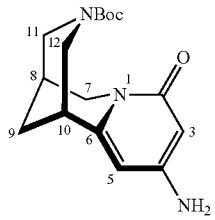

Method A:

In a Schlenk tube, a mixture of N-Boc-4-bromo-cytisine 61 (184 mg, 0.5 mmol), NaN$_3$ (65 mg, 1.0 mmol), CuI (9 mg, 10 mol %), L-proline (17 mg, 30 mol %), NaOH (6 mg, 30 mol %) in EtOH/H$_2$O (7:3) (5 mL) was heated at 95° C. overnight. The mixture was cooled and partitioned between H$_2$O and DCM. The aqueous layer was extracted with DCM (2×10 mL). The combined organic layers were washed with brine, dried over Na$_2$SO$_4$, filtered and concentrated in vacuo. The crude was purified by flash column chromatography on silica gel [DCM/MeOH/NH$_4$OH (89:10:1)] to give amine 80 (116 mg, 76%) as an off-white solid.

Method B:

A mixture of N-Boc-4-bromo-cytisine 61 (92 mg, 0.25 mmol) and copper (2 mg, 10 mol %) in NH$_4$OH (0.5 mL, conc. aq. sol.) was stirred at 100° C. for 24 h in a sealed tube. The mixture was cooled and extracted with DCM (5×5 mL). The combined organic layers were dried over Na$_2$SO$_4$, filtered and concentrated in vacuo. The crude was purified by flash column chromatography on silica gel [DCM/MeOH/NH$_4$OH: (89:10:1)] to give 80 (64 mg, 85%) as an off-white solid.

R$_f$: 0.28 [DCM/MeOH (10% MeOH)]; mp: >200° C.; FTIR ν$_{max}$/cm$^{-1}$ (neat): 3414, 3302, 3211, 2905, 1679, 1642, 1551; $^1$H NMR (400 MHz, MeOD, δ$_H$): 5.83 (s, 1H, C3-H), 5.51 (s, 1H, C5-H), 4.29-4.02 (m, 3H, C7-H$_a$, C11-H, C12-H), 3.68 (dd, 1H, J=6.5, 14.5 Hz, C7-H$_b$), 3.34-2.93 (m, 3H, C10-H, C11-H, C12-H), 2.36 (s, 1H, C8-H), 1.98 (s, 2H, C9-H), 1.34-1.24 (m, 9H, Boc); $^{13}$C NMR (100 MHz, MeOD, δ$_C$): 165.2 (CO), 157.7 (CO Boc), 154.7 (C6), 149.0/148.8 (C4, rotamers), 99.6/99.3 (C3, rotamers), 91.9 (C5), 80.1/79.6 (q Boc, rotamers), 51.4/50.2/50.1 (C11, C12, rotamers), 49.0 (C7), 34.9 (C10), 27.9/27.7 (C8, rotamers), 27.0 (3C, Boc), 25.7 (C9); HRMS (ESI$^+$): calculated for C$_{16}$H$_{24}$N$_3$O$_3$: 306.1812, found [M+H]$^+$: 306.1809.

Example 16b—(+)4-aminocytisine dihydrochloride salt (81)

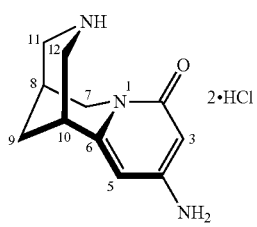

Following the general procedure A, N-Boc 4-aminocytisine 80 (1.0 mmol) gave amine 81 (273 mg, 98%) as an off-white solid.

mp: >200° C.; [α]$_D^{25}$=+77 [c 1.0, MeOH]; FTIR ν$_{max}$/cm$^{-1}$ (neat): 2929, 2790, 1649, 1533; $^1$H NMR (400 MHz, D$_2$O, δ$_H$): 6.26 (s, 1H, C3-H), 4.09 (d, 1H, J=15.0 Hz, C7-H$_a$), 3.95 (dd, 1H, J=6.5, 15.0 Hz, C7-H$_b$), 3.41-3.26 (m, δ$_H$, C10-H, C11-H, C12-H), 2.68 (s, 1H, C8-H), 2.07-1.94 (m, 2H, C9-H), C5-H not detected due to deuterium exchange; $^{13}$C NMR (100 MHz, D$_2$O, δ$_C$): 160.9 (CO), 159.1 (C4), 148.1 (C6), 104.5 (d, J=7.2 Hz, C3), 91.5-91.0 (m, C5), 49.2 (C11 or C12), 48.8 (C7), 48.1 (C11 or C12), 31.2 (C10), 24.5 (C8), 22.5 (C9); HRMS (ESI$^+$): calculated for C$_{11}$H$_{16}$N$_3$O: 206.1288, found [M+$^{H-2}$HCl]$^+$: 206.1292.

Example 17—(−)4-Fluorocytisine (82)

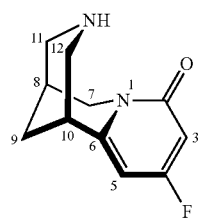

To a solution of N-Boc-4-amino-cytisine 80 (305 mg, 1.0 mmol) in HF-pyridine complex (70%, 2.0 mL) at −20° C. was slowly added tBuONO (0.18 mL, 1.5 mmol) over 1 min. The reaction was stirred at −20° C. for 30 min, then allowed to warm to r.t. for 2 h and finally heated at 60° C. overnight. The mixture was cooled to 0° C. and quenched to pH 10 with conc. aq. NH$_4$OH. The mixture is diluted with EtOAC (10 mL) and filtered to remove the insoluble salts. The aqueous layer was extracted with EtOAc (4×10 mL). The combined organic layers were concentrated in vacuo. The crude was partitioned between 3M HCl (5 mL) and DCM (5 mL). The aqueous layer was washed with DCM (2×5 mL), basified with concentrated NH$_4$OH to pH 10 and extracted with DCM (5×5 mL). The combined organic layers were dried over Na$_2$SO$_4$, filtered and concentrated in vacuo. The crude was purified by flash column chromatography on silica gel [DCM/MeOH/NH$_4$OH (89:10:1)] to give 82 (140 mg, 67%) as a pale yellow solid. An analytic pure sample was obtained by recrystallization in toluene.

R$_f$: 0.25 [DCM/MeOH (20% MeOH)]; mp: 143-145° C. (toluene); [α]$_D^{25}$=−92 [c 1.0, EtOH]; FTIR ν$_{max}$/cm$^{-1}$ (neat): 3391, 3289, 3069, 2948, 2898, 2852, 1644, 1552; $^1$H NMR (400 MHz, CDCl$_3$, δ$_H$): 6.06 (dd, 1H, J=2.5, 11.0 Hz, C3-H), 5.87 (dd, 1H, J=2.5, 7.0 Hz, C5-H), 4.04 (d, 1H, J=15.5 Hz, C7-H$_a$), 3.83 (dd, 1H, J=6.5, 15.5 Hz, C7-H$_b$), 3.08-2.95 (m, 4H, C11-H, C12-H), 2.89-2.86 (m, 1H, C10-H), 2.34-2.29 (m, 1H, C8-H), 1.93 (t, 2H, J=3.0 Hz, C9-H), 1.56 (br s, 1H, NH); $^{13}$C NMR (100 MHz, CDCl$_3$, δ$_C$): 169.9 (d, J=264.0 Hz, C4), 164.8 (d, J=19.0 Hz, CO), 153.5 (d, J=13.5 Hz, C6), 99.6 (d, J=16.5 Hz, C3), 96.5 (d, J=26.0 Hz, C5), 53.7, 52.9 (C11, C12), 49.8 (C7), 36.0 (d, J=2.0 Hz, C10), 27.5 (C8), 26.2 (C9); $^{19}$F NMR (376 MHz, CDCl$_3$, δ$_F$): −99.6 (m); HRMS (ESI$^+$): calculated for C$_{11}$H$_{14}$FN$_2$O: 209.1090, found [M+H]$^+$: 209.1095. Anal. Calc. for C$_{11}$H$_{13}$FN$_2$O: theor. C=63.45, H=6.29, N=13.45, found C=63.05, H=6.33, N=13.20.

Example 18a—N-Boc 4-(N-Methylamino)cytisine (83)

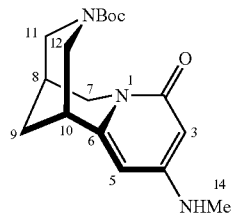

A mixture of N-Boc-4-bromo-cytisine 61 (369 mg, 1.0 mmol) and copper (7 mg, 10 mol %) in 40% aq. MeNH$_2$ (2.0 mL) was stirred at 100° C. for 24 h in a sealed tube. The mixture was cooled to r.t. and extracted with DCM (5×10 mL). The combined organic layers were dried over Na$_2$SO$_4$, filtered and concentrated in vacuo. The crude was purified by flash chromatography on silica gel (DCM/MeOH (94:6)] to give 83 (274 mg, 86%) as an off-white solid.

R$_f$: 0.58 [DCM/MeOH (10% MeOH)]; mp: 198-200° C. (toluene); FTIR $v_{max}$/cm$^{-1}$ (neat): 3266, 2928, 1684, 1641, 1571; $^1$H NMR (400 MHz, CDCl$_3$, $\delta_H$): 5.49 (s, 1H, C3-H), 5.37 (s, 1H, C5-H), 4.53 (s, 1H, NH), 4.28-4.03 (m, 3H, C7-H$_a$, C10-H, C12-H), 3.72 (dd, 1H, J=6.5, 15.0 Hz, C7-H$_b$), 3.02-2.70 (m, 6H, C10-H, C11-H, C12-H, C14-H), 2.31 (s, 1H, C8-H), 1.93-1.81 (m, 2H, C9-H), 1.32-1.22 (m, 9H, Boc); $^{13}$C NMR (100 MHz, CDCl$_3$, $\delta_C$): 164.7 (CO), 156.0 (CO Boc), 154.8/154.5 (C6, rotamers), 147.9/147.3 (C4, rotamers), 98.0/97.2 (C3, rotamers), 90.4/90.1 (C5, rotamers), 80.2/79.6 (q Boc, rotamers), 51.7/50.7/50.4/49.4 (C11, C12, rotamers), 47.9 (C7), 34.8 (C10), 29.4 (C14), 28.1 (3C, Boc), 27.6 (C8), 26.4 (C9); HRMS (ESI$^+$): calculated for C$_{17}$H$_{26}$N$_3$O$_3$: 320.1969, found [M+H]$^+$: 320.1974.

Example 18b—(+)4-(N-Methylamino)cytisine dihydrochloride salt (84)

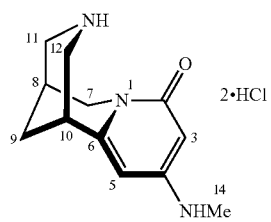

Following the general procedure A, 4-N-methylamino-N-Boc-cytisine 83 (0.77 mmol) gave amine 84 (190 mg, 85%) as a colourless solid.

mp: >200° C., colourless powder; [α]$_D^{25}$=+66 [c 1.0, MeOH]; FTIR $v_{max}$/cm$^{-1}$ (neat): 3240, 2939, 2714, 2583, 1644, 1557; $^1$H NMR (400 MHz, D$_2$O, $\delta_H$): 6.25 (s, 1H, C3-H), 4.09 (d, 1H, J=15.0 Hz, C7-H$_a$), 3.95 (dd, 1H, J=6.5, 15.0 Hz, C7-H$_b$), 3.42-3.26 (m, $\delta_H$, C10-H, C11-H, C12-H), 2.71 (s, 4H, C8-H, C14-H), 2.05-1.94 (m, 2H, H$_9$), C5-H not detected due to deuterium exchange; $^{13}$C NMR (100 MHz, D$_2$O, $\delta_C$): 160.7 (CO), 158.7 (C4), 147.1 (C6), 103.6 (C3), 88.4-87.9 (C5), 49.3 (C11 or C12), 48.7 (C7), 48.1 (C11 or C12), 31.3 (C10), 28.5 (C14), 24.5 (C8), 22.6 (C9); HRMS (ESI$^+$): calculated for C$_{12}$H$_{18}$N$_3$O: 220.1444, found [M+H-2HCl]$^+$: 220.1441.

Example 19a—N-Boc 4-(N, N'-Dimethylamino)cytisine (85)

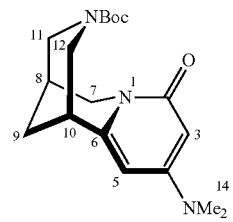

A mixture of N-Boc-4-bromo-cytisine 61 (369 mg, 1.0 mmol) and copper (6 mg, 10 mol %) in 40% aq. Me2NH (2.0 mL) was stirred at 100° C. for 24 h in a sealed tube. The mixture was cooled, diluted with 35% ammonia (2 mL) and the aqueous phase was extracted with DCM (5×10 mL). The combined organic layers were dried on Na$_2$SO$_4$, filtered and concentrated in vacuo. The crude reaction mixture was purified by flash column chromatography on silica gel [DCM/MeOH/NH$_4$OH (94.5:5:0.5)] to give 85 (212 mg, 64%) as a white foam.

R$_f$: 0.19 [DCM/MeOH (10% MeOH)]; FTIR $v_{max}$/cm$^{-1}$ (neat): 2972, 2928, 2863, 1687, 1645, 1578; $^1$H NMR (400 MHz, CDCl$_3$, $\delta_H$): 5.64 (d, 1H, J=2.5 Hz, C3-H), 5.42 (s, 1H, C5-H), 4.31-4.04 (m, 3H, C7-H$_a$, C11-H, C12-H), 3.73 (dd, 1H, J=6.5, 15.0 Hz, C7-H$_b$), 3.04-2.81 (m, 9H, C10-H, C11-H, C12-H, 2×C14-H), 2.31 (s, 1H, C8-H), 1.94-1.83 (m, 2H, C9-H), 1.32-1.19 (m, 9H, Boc); $^{13}$C NMR (100 MHz, CDCl$_3$, $\delta_C$): 164.2 (CO), 156.0 (CO Boc), 154.8/154.4 (C4, rotamers), 147.9/147.5 (C6, rotamers), 95.6/95.1 (C3, rotamers), 91.9/91.5 (C5, rotamers), 80.2/79.5 (q Boc, rotamers), 51.8/50.7/50.4/49.3 (C11, C12, rotamers), 47.8 (C7), 39.3 (2C, C14), 35.2 (C10), 28.1 (3C, Boc), 27.5 (C8), 26.5 (C9); HRMS (ESI$^+$): calculated for C$_{18}$H$_{28}$N$_3$O$_3$: 334.2125, found [M+H]$^+$: 334.2113.

Example 19b—(+)4-(N, N'-dimethylamino)cytisine dihydrochloride salt (86)

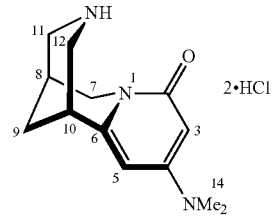

Following the general procedure A, N-Boc-4-N, N'-dimethylamino-cytisine 85 (202 mg, 0.61 mmol) gave amino 86 (174 mg, 93%) as a colourless solid.

mp: >200° C., colourless powder; [α]$_D^{25}$=+84 [c 1.0, MeOH]; FTIR $v_{max}$/cm-(neat): 3202, 2960, 2753, 1644, 1551; $^1$H NMR (400 MHz, D$_2$O, $\delta_H$): 6.41 (s, 1H, C3-H), 4.12 (d, 1H, J=15.0 Hz, C7-H$_a$), 3.98 (dd, 1H, J=6.5, 15.0

Hz, C7-H$_b$), 3.42-3.27 (m, δ$_H$, C10-H, C11-H, C12-H), 2.96 (s, 6H, C14-H), 2.68 (s, 1H, C8-H), 2.07-1.96 (m, 2H, C9 H), H$_5$ not detected due to deuterium exchange; $^{13}$C NMR (100 MHz, D$_2$O, δ$_C$): 159.8 (CO), 157.4 (C4), 147.1 (C6), 102.5 (d, J=5.0 Hz, C3), 89.0-88.5 (m, C5), 49.3 (C11 or C12), 48.7 (C7), 48.1 (C11 or C12), 39.1 (2C, C14), 31.5 (C10), 24.5 (C8), 22.6 (C9); HRMS (ESI$^+$): calculated for C$_{13}$H$_{20}$N$_3$O [M+H-2HCl]$^+$: 234.1601, found: 234.1606.

Example 20a—N-Boc 4-(N-benzoylamino)cytisine (95)

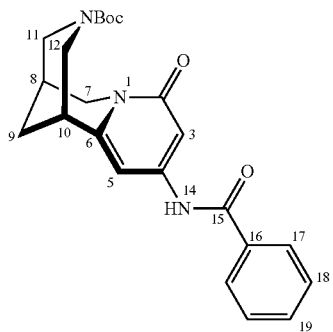

To a mixture of N-Boc-4-bromo-cytisine 61 (369 mg, 1.0 mmol), CuI (19 mg, 10 mol %), benzamide (145 mg, 1.2 mmol) and K$_2$CO$_3$ (276 mg, 2.0 mmol) in dry toluene (5.0 mL) was added N,N'-dimethylethylenediamine (11 μL, 10 mol %). The mixture was heated at 110° C. for three days. After cooling, the mixture was diluted with H$_2$O (10 mL) and the aqueous phase was extracted with DCM (5×10 mL). The combined organic layers were dried over Na$_2$SO$_4$, filtered and concentrated in vacuo. The crude reaction mixture was purified by flash column chromatography on silica gel [DCM/MeOH/NH$_4$OH (95:5:0.1)] to give the 95 (425 mg) as a yellow solid. The resultant solid was washed in boiling toluene (10 mL) overnight to give 95 (372 mg, 91%) as a colourless solid.

R$_f$: 0.49 [DCM/MeOH (10% MeOH)]; mp: >200° C., colourless powder; FTIR v$_{max}$/cm$^{-1}$ (neat): 3067, 2972, 2864, 1648, 1626, 1548, 1483; $^1$H NMR (400 MHz, CDCl$_3$, δ$_H$): 7.74-7.72 (m, 2H, C17-H), 7.40-7.28 (m, 3H, C18-H, C19-H), 7.06/6.75 (2 br s, 2×0.5H, C3-H, rotamers), 6.62/6.33 (2 br s, 2×0.5H, C5-H, rotamers), 4.08-3.94 (m, 4H, NH, C7-H$_a$, C11-H, C12-H), 3.61 (dd, 1H, J=6.5, 15.5 Hz, C7-H$_b$), 3.16-2.91 (m, 3H, C10-H, C11-H, C12-H), 2.27 (s, 1H, C8-H), 1.83 (s, 2H, C9-H), 1.16-1.05 (m, 9H, Boc); $^{13}$C NMR (100 MHz, CDCl$_3$, δ$_C$): 167.5 (C14), 164.5 (CO), 154.5 (CO Boc), 149.5, 148.8 (C6, C4), 133.9 (C16), 131.9 (C19), 128.2 (C17, C21), 127.4 (C18, C20), 102.2/101.9 (C3, rotamers), 101.2 (C5), 80.5/79.9 (q Boc, rotamers), 51.3/50.3/50.1/49.1/48.9/48.7/48.5/48.4/48.2/48.0/47.8 (C7, C11, C12, rotamers), 34.8 (C10), 27.5 (3C, Boc), 27.2 (C8), 25.7 (C9); HRMS (ESI$^+$): calculated for C$_{23}$H$_{28}$N$_3$O$_4$: 410.2074, found [M+H]$^+$: 410.2064, calculated for C$_{23}$H$_{27}$N$_3$NaO$_4$: 432.1894, found [M+Na]$^+$: 432.1884.

Example 20b—(+)4-(A-Benzoylamino)cytisine hydrochloride salt (96)

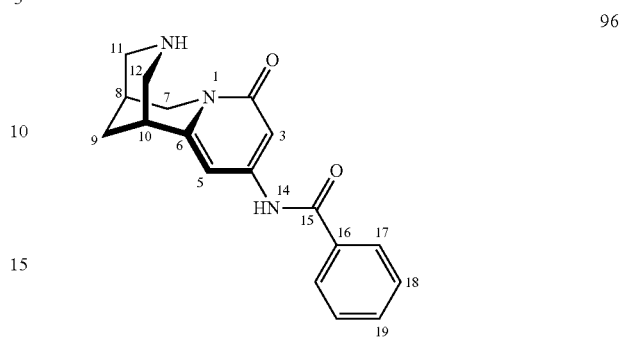

Following the general procedure B, N-Boc-4-(N-benzamide)-cytisine 95 (363 mg, 0.89 mmol) gave benzamide 96 (290 mg, 80%) as a colourless solid.

mp: >200° C., colourless powder; [α]$_D^{26}$=+30 [c 0.5, MeOH]; FTIR v$_{max}$/cm$^{-1}$ (neat): 2937, 2798, 1677, 1633, 1599; $^1$H NMR (400 MHz, D$_2$O, δ$_H$): 7.55 (d, 2H, J=7.5 Hz, C17-H, C21-H), 7.45-7.42 (m, 1H, C19-H), 7.32-7.28 (m, 2H, C18-H, C20-H), 6.76 (d, 1H, J=2.0 Hz, C3-H), 6.62 (d, 1H, J=2.0 Hz, C5-H), 3.96 (d, 1H, J=15.5 Hz, C7-H$_a$), 3.70 (dd, 1H, J=6.5, 15.5 Hz, C7-H$_b$), 3.39-3.23 (m, δ$_H$, C10-H, C11-H, C12-H), 2.64 (s, 1H, C8-H), 1.96 (d, 1H, J=13.5 Hz, C9-H), 1.76 (d, 1H, J=13.5 Hz, C9-H); $^{13}$C NMR (100 MHz, D$_2$O, δ$_C$): 169.1 (C14), 164.6 (CO), 149.2 (C4), 147.6 (C6), 133.0 (C19), 132.6 (C16), 128.7 (C18, C20), 127.5 (C17, C21), 104.1 (C5), 102.8 (C3), 49.2 (C11 or C12), 48.6 (C7), 48.2 (C11 or C12), 31.5 (C10), 24.6 (C8), 22.5 (C9); HRMS (ESI+): calculated for C$_{18}$H$_{20}$N$_3$O$_2$: 310.1550, found [M+H—HCl]$^+$: 310.1549.

Example 21a—N-Boc 4-(N-acetylamino)cytisine (93)

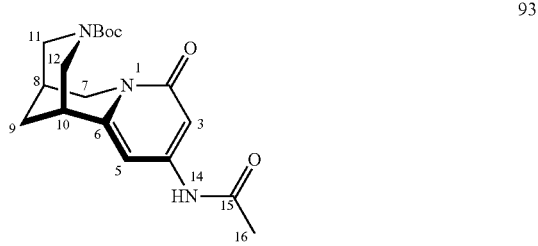

To a mixture of N-Boc-4-bromo-cytisine 61 (369 mg, 1.0 mmol), CuI (19 mg, 10 mol %), acetamide (70 mg, 1.2 mmol) and K$_2$CO$_3$ (276 mg, 2.0 mmol) in dry toluene (5.0 mL) was added N,N'-dimethylethylenediamine (11 μL, 10 mol %). The mixture was heated at 110° C. for 24 h. After cooling to r.t., the mixture was diluted with H$_2$O (10 mL), then extracted with DCM (5×10 mL). The combined organic layers were dried over Na$_2$SO$_4$, filtered and concentrated in vacuo. The crude was purified by flash column chromatography on silica gel [DCM/MeOH/NH$_4$OH (95:5:0.1)] to give 93 (340 mg, 98%) as a pale yellow foam with few impurities. The product was used in the next step without further purification.

R$_f$: 0.49 [DCM/MeOH (10% MeOH)]; FTIR $v_{max}$/cm$^{-1}$ (neat): 2971, 2929, 1688, 1644, 1556, 1422; $^1$H NMR (400 MHz, CDCl$_3$, $\delta_H$): 7.11/6.74 (2×s, 1H, C3-H, rotamers), 6.58/6.23 (2×s, 1H, H$_5$, rotamers), 4.34-4.12 (m, 3H, C7-H$_a$, C11-H, C12-H), 3.77 (dd, 1H, J=6.5, 15.5 Hz, C7-H$_b$), 3.04-2.97 (m, 3H, C10-H, C11-H, C12-H), 2.51 (s, 1H, C8-H), 2.09 (s, 3H, C16-H), 2.01-1.89 (m, 2H, C9-H), 1.33-1.21 (m, 9H, Boc); $^{13}$C NMR (100 MHz, CDCl$_3$, $\delta_C$): 170.2 (C15), 164.4 (CO), 154.8/154.5 (CO Boc, rotamers), 148.5, 148.3 (C6, C4), 101.9 (C3), 100.4 (C5), 80.7/79.6 (q Boc, rotamers), 51.6/50.7/50.5/49.3 (C11, C12, rotamers), 48.6 (C7), 35.0 (C10), 28.1 (3C, Boc), 27.5 (C8), 26.2 (C9), 24.6 (C16); HRMS (ESI$^+$): calculated for C$_{18}$H$_{26}$N$_3$O$_4$: 348.1918, found [M+H]$^+$: 348.1916, C$_{18}$H$_{25}$N$_3$NaO$_4$: 370.1737, found [M+Na]$^+$: 370.1737.

Example 21b—(+)4-(A-acetylamino)cytisine (94)

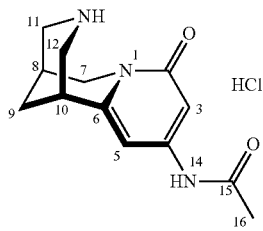

Following the general procedure B, N-Boc-4-(N-acetamide)-cytisine 93 (306 mg, 0.88 mmol) gave 94 (250 mg, quantitative) as a pale yellow solid.

mp: >200° C., colourless powder; [α]$_D^{25}$=+30 [c 0.5, MeOH]; FTIR $v_{max}$/cm$^{-1}$ (neat): 2457, 2374, 1612, 1530, 1506; $^1$H NMR (400 MHz, D$_2$O, $\delta_H$): 6.79 (d, 1H, J=2.0 Hz, C3-H), 6.64 (d, 1H, J=2.0 Hz, C5-H), 4.04 (d, 1H, J=15.5 Hz, C7-H$_a$), 3.88 (dd, 1H, J=6.5, 15.5 Hz, C7-H$_b$), 3.40-3.25 (m, $\delta_H$, C10-H, C11-H, C12-H), 2.70 (s, 1H, C8-H), 2.05-1.91 (m, $\delta_H$, C9-H, C16-H); $^{13}$C NMR (100 MHz, D$_2$O, $\delta_C$): 173.6 (C15), 164.5 (CO), 149.4 (C4), 148.1 (C6), 104.4 (C5), 101.7 (C3), 49.2 (C11 or C12), 48.8 (C7), 48.1 (C11 or C12), 31.5 (C10), 24.6 (C8), 23.6 (C16), 22.5 (C9); HRMS (ESI$^+$): calculated for C$_{13}$H$_{18}$N$_3$O$_2$: 248.1394, found [M+H—HCl]$^+$: 248.1394.

Example 22—(+)4-N-morpholinecytisine dihydrochloride salt (92)

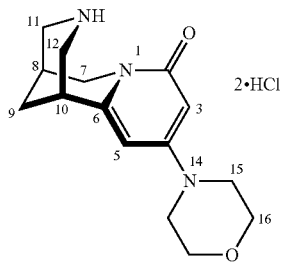

A sealed tube was charged with N-Boc-4-bromo-cytisine 61 (370 mg, 1.0 mmol), copper (II) oxide (15 mg, 0.1 eq.) and morpholine (0.4 mL, 5 eq.), and the reaction mixture was dissolved in water (2.0 mL, 0.5 M) and heated at 100° C. under air for 18 h. The reaction mixture was cooled to r.t. and the aqueous phase was extracted with DCM (4×25 mL). The combined organic phases were dried over MgSO$_4$, filtered and concentrated. The resulting N-Boc protected cytisine derivative was deprotected and converted into the HCl salt using the general procedure A, yielding 92 (180 mg, 85%) as a colourless solid.

mp: >200° C., colourless powder; [α]$_D^{25}$=+61 [c 1.0, MeOH]; FTIR $v_{max}$/cm$^1$(neat): 2560, 1641, 1541; $^1$H NMR (500 MHz, D$_2$O, $\delta_H$): 6.48 (s, 1H, C3-H), 4.09 (d, 1H, J=16.0 Hz, C7-H), 3.96 (dd, 1H, J=16.0, 5.5 Hz, C7-H), 3.74 (s, 4H, C11-H, C12-H), 3.39 (m, 9H, CH$_2$ morpholine, C10-H), 2.71 (s, 1H, C8-H), 2.04 (m, 2H, C9-H); C5-H is not visible due to H-solvent exchange; $^{13}$C NMR (125 MHz, D$_2$O, $\delta_C$): 162.5 (CO), 157.9 (C6), 147.4 (C4), 101.6 (C3), 91.7 (C5), 65.8 (2C, C15), 49.4, 48.2 (C11, C12), 48.4 (C7), 45.7 (2C, C16), 31.7 (C10), 24.6 (C8), 22.7 (C9); HRMS (ESI$^+$): calculated for C15H$_{22}$N$_3$O$_2$: 276.1707, found [M+H—HCl]$^+$: 276.1718.

Example 23a—N-Boc 4-(N-(L-proline methyl ester)cytisine (136)

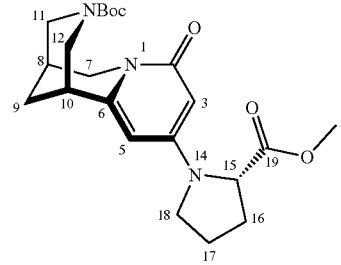

A mixture of N-Boc 4-bromocytisine 61 (369 mg, 1.0 mmol), L-proline methyl ester hydrochloride (198 mg, 1.2 mmol), Cs$_2$CO$_3$ (814 mg, 2.5 mmol), Pd(OAc)$_2$ (11 mg, 5 mol %) and (±)-BINAP (44 mg, 7 mol %) in dry toluene (5.0 mL) was stirred for 48 h at 100° C. The mixture was cooled to r.t., filtered through a short pad of Celite,® washed with EtOAc and concentrated in vacuo. The crude was purified by flash column chromatography on silica gel [DCM/MeOH/NH$_4$OH (95:5:0.1)] to give 136 (371 mg, 89%) as an off-white foam with few impurities.

R$_f$: 0.11 [DCM/MeOH (5% MeOH)]; $^1$H NMR (400 MHz, CDCl$_3$, $\delta_H$): 5.55 (s, 1H, C3-H), 5.28 (s, 1H, C5-H), 4.27-4.02 (m, 4H, C7-H$_a$, C11-H, C12-H, C15-H), 3.73-3.67 (m, 4H, C7-H$_b$, C20-H), 3.48 (s, 1H, C18-H), 3.36 (s, 1H, C18-H), 3.00-2.85 (m, 3H, C10-H, C11-H, C12-H), 2.31-2.16 (m, 2H, C18-H, C$_{16}$H), 2.08-1.99 (m, 3H, C16-H, C17-H), 1.91-1.81 (m, 2H, C9-H), 1.31-1.18 (m, 9H, Boc); $^{13}$C NMR (125 MHz, CDCl$_3$, $\delta_C$): 173.3 (C19), 164.0 (CO), 154.7/154.4 (CO Boc, rotamers), 153.0 (C4), 148.6/148.2 (C6, rotamers), 96.2/95.5 (C3, rotamers), 92.3 (C5), 80.2/79.6 (q Boc, rotamers), 60.0 (C15), 52.3 (C20), 50.7/50.6/50.4/49.4 (C11, C12, rotamers), 47.9 (C18), 47.8 (C7), 35.1 (C10), 30.6 (C16), 28.1 (3C, Boc), 27.5 (C8), 26.3 (C9), 23.5 (C17); HRMS (ESI+): calculated for C$_{22}$H$_{32}$N$_3$O$_5$: 418.2336, found [M+H]$^+$: 418.2340, calculated for C$_{22}$H$_{31}$N$_3$NaO$_5$: 440.2156, found [M+Na]$^+$: 440.2161.

Example 23b—(+)4-(N-(L-proline methyl ester)cytisine dihydrochloride salt (137)

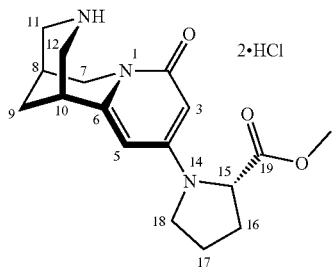

137

Following the general procedure B, N-Boc-4-(N-(L-proline methyl ester)-cytisine 136 (0.88 mmol) gave 137 (304 mg, 89%) as a colourless solid.

mp: >200° C., colourless powder; $[\alpha]_D^{26}$=+2 [c 0.5, MeOH]; FTIR $v_{max}$/cm$^{-1}$ (neat): 2951, 2714, 2385, 1740, 1637, 1538, 1484; $^1$H NMR (400 MHz, D$_2$O, $\delta_H$): 6.38 (s, 1H, C3-H), 4.62 (s, 1H, C15-H), 4.25 (d, 1H, J=15.0 Hz, C7-H$_a$), 4.12 (dd, 1H, J=6.5, 15.5 Hz, C7-H$_b$), 3.79 (s, 3H, C20-H), 3.60-3.40 (m, 7H, C10-H, C11-H, C12-H, C18-H), 2.82 (s, 1H, C8-H), 2.43-2.26 (m, 2H, C16-H), 2.18-1.99 (m, 4H, C14-H, C17-H), H$_3$ not detected due to deuterium exchange; $^{13}$C NMR (100 MHz, D$_2$O, $\delta_C$): 174.6 (C19), 160.9 (CO), 155.2 (C4), 147.8 (C6), 102.9 (C3), 60.5 (C15), 53.2 (C20), 49.3, 48.7, 48.6, 48.0 (C7, C11, C12, C18), 31.4 (C10), 30.1 (C16), 24.5 (C8), 23.0 (C17), 22.5 (C20), C3 not detected due to deuterium exchange; HRMS (ESI$^+$): calculated for C$_{17}$H$_{24}$N$_3$O$_3$: 318.1812, found [M+H-2HCl]$^+$: 318.1802.

Example 24—(−)4-(N-(L-proline)cytisine dihydrochloride salt (138)

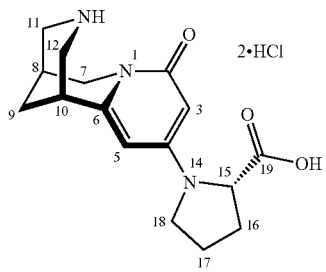

138

A mixture of N-Boc-4-(N-(L-proline methyl ester)-cytisine 138 (341 mg, 0.82 mmol) in HCl (37% in water, 8.2 mL) was heated at reflux for 48 h. The mixture was cooled to r.t. and concentrated in vacuo. The crude was solubilized in MeOH (4 mL) and then acetone was slowly added (40 mL). The resulting suspension was stirred for 1 h. The solid was filtered off, washed with acetone and dried under vacuum to give 138 (261 mg, 85%) as a pale brown solid.

mp: >200° C., colourless powder; $[\alpha]_D^{26}$=−32 [c 0.5, water]; FTIR $v_{max}$/cm$^{-1}$ (neat): 2908, 2754, 2583, 1719, 1640, 1546; $^1$H NMR (400 MHz, D$_2$O, $\delta_H$): 6.28 (s, 1H, C3-H), 4.51 (s, 1H, C15-H), 4.21 (d, 1H, J=15.0 Hz, C7-H$_a$), 4.07 (dd, 1H, J=6.5, 15.0 Hz, C7-H$_b$), 3.59-3.39 (m, 7H, C10-H, C11-H, C12-H, C18-H), 2.81 (s, 1H, C8-H), 2.46-2.36 (m, 1H, C16-H), 2.28-2.22 (m, 1H, C16-H), 2.17-2.01 (m, 4H, C14-H, C17-H), H$_5$ not detected due to deuterium exchange; $^{13}$C NMR (100 MHz, D$_2$O, $\delta_C$): 176.1 (C19), 160.8 (CO), 155.2 (C4), 147.8 (C6), 102.8 (C3), 60.6 (C15), 49.3, 48.8, 48.6, 48.0 (C7, C11, C12, C18), 31.4 (C10), 30.3 (C16), 24.5 (C8), 23.0 (C17), 22.5 (C9), C3 not detected; HRMS (ESI$^+$): calculated for C$_{16}$H$_{22}$N$_3$O$_3$ [M+H-2HCl]$^+$: 304.1656, found: 304.1651.

Example 25a—N-Boc 4-(carboxymethyl)cytisine (119)

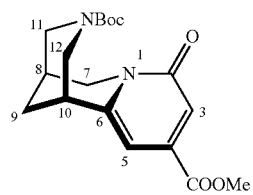

119

A solution of N-Boc-4-bromo-cytisine 61 (369 mg, 1.0 mmol), Et$_3$N (0.4 mL, 2.5 mmol), dppp (82 mg, 0.2 mmol) and Pd(OAc)$_2$ (45 mg, 0.2 mmol) in DMF/MeOH (1:1) (5 mL) was stirred at 80° C. under 1 atm of CO for 24 h. The mixture was cooled to r.t., filtered through Celite® and concentrated in vacuo. The crude was purified by flash column chromatography on silica gel [EtOAc] to give 119 (300 mg, 86%) as a yellow foam.

R$_f$: 0.25 [EtOAc]; FTIR $v_{max}$/cm$^{-1}$ (neat): 2931, 1683, 1657, 1575, 1547; $^1$H NMR (400 MHz, CDCl$_3$, $\delta_H$): 7.00 (s, 1H, C3-H), 6.54 (s, 1H, C5-H), 4.31-4.06 (m, 3H, C7-H$_a$, C11-H, C12-H), 3.85 (s, 3H, Me), 3.79 (dd, 1H, J=6.5, 15.5 Hz, C7-H$_b$), 3.14-2.88 (m, 3H, C10-H, C11-H, C12-H), 2.41 (s, 1H, C8-H), 1.98-1.91 (m, 2H, C9-H), 1.28-1.15 (m, 9H, Boc); $^{13}$C NMR (100 MHz, CDCl$_3$, $\delta_C$): 165.4 (C14), 163.2 (CO), 154.32 (CO Boc), 150.0/149.5 (C4, rotamers) 139.5 (C6), 118.4 (C3), 104.1/103.5 (C5, rotamers), 80.4/79.9 (q Boc, rotamers), 52.7 (C7), 51.5/50.5/50.3 (C11, C12, rotamers), 49.2 (Me), 35.0 (C10), 28.0 (3C, Boc), 27.4 (C8), 26.0 (C9); HRMS (ESI+): calculated for C$_{18}$H$_{25}$N$_2$O$_5$: 349.1758, found [M+H]$^+$: 349.1750.

Example 25b—(−)4-carboxymethycytisine (120)

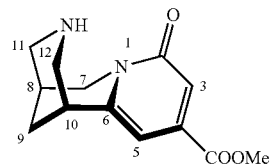

120

To a solution of N-Boc-4-methyl-ester-cytisine 119 (95 mg, 0.27 mmol) in DCM (1.3 mL) was added TFA (0.21 mL, 2.7 mmol). The mixture was stirred for 24 h then concentrated in vacuo. The crude was partitioned between HCl 3M (5 mL) and DCM (5 mL). The aqueous layer was washed with DCM (2×5 mL), basified with Na$_2$CO$_3$ to pH 9 and then extracted with DCM (5×5 mL). The combined organic layers were dried over Na$_2$SO$_4$, filtered and concentrated in vacuo to give 120 (55 mg, 81%) as an off-white solid. An analytic pure sample was obtained by recrystallization in toluene.

R$_f$: 0.23 [DCM/MeOH (10% MeOH)]; mp: 141-142° C., (toluene); [α]$_D^{25}$=−96 [c 0.3, water]; FTIR v$_{max}$/cm$^{-1}$ (neat): 3300, 2926, 2893, 2847, 1719 (w), 1648,1571; $^1$H NMR (400 MHz, CDCl$_3$, δ$_H$): 7.02 (d, 1H, J=1.5 Hz, C3-H), 6.49 (d, 1H, J=1.5 Hz, C5-H), 4.08 (d, 1H, J=15.5 Hz, C7-H$_a$), 3.88 (dd, 1H, J=6.5, 15.5 Hz, C7-H$_b$), 3.87 (s, 3H, Me), 3.08-2.95 (m, δ$_H$, C10-H, C11-H, C12-H), 2.33 (s, 1H, C8-H), 1.97-1.90 (m, 2H, C9-H), 1.50 (s, 1H, NH); $^{13}$C NMR (100 MHz, CDCl$_3$, δ$_C$): 165.6 (COOMe), 163.4 (CO), 151.9 (C6), 139.4 (C4), 118.0 (C3), 103.3 (C5), 53.8, 52.9 (C12, C11), 52.7 (Me), 50.2 (C7), 35.8 (C10), 27.7 (C8), 26.2 (C9); HRMS (ESI$^+$): calculated for C$_{13}$H$_{17}$N$_2$O$_3$: 249.1234, found [M+H]$^+$: 249.1245.

Example 26—(−)4-Carboxylic acidcytisine, hydrochloride salt (229)

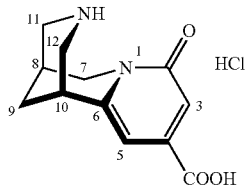

229

A solution of N-Boc-4-methyl-ester-cytisine 119 (263 mg, 0.75 mmol) in HCl (37% aq.sol. 7.5 mL) was heated at reflux for 24 h. The mixture was cooled to r.t. then concentrated in vacuo. The crude reaction mixture was solubilized in MeOH (30 mL) and then acetone was slowly added (300 mL). The resulting suspension was stirred for 1 h. The solids were filtered off, washed with acetone and dried under vacuum to give 229 (164 mg, 81%) as a colourless solid.

mp: >200° C., colourless powder; [α]$_D^{22}$=−33 [c 0.3, water]; FTIR v$_{max}$/cm$^{-1}$ (neat): 1698, 1648, 1543, 1471; $^1$H NMR (400 MHz, D$_2$O, δ$_H$): 6.88 (s, 1H, C3-H), 6.79 (s, 1H, C5-H), 4.06 (d, 1H, J=15.5 Hz, C7-H$_a$), 3.91 (dd, 1H, J=6.5, 15.5 Hz, C7-H$_b$), 3.44-3.27 (m, δ$_H$, C10-H, C11-H, C12-H), 2.75 (s, 1H, C8-H), 2.08-1.96 (m, 2H, C9-H); $^{13}$C NMR (100 MHz, D$_2$O, δ$_C$): 167.7 (COOH), 164.8 (CO), 148.0 (C6), 142.1 (C4), 118.1 (C3), 107.8 (C5), 49.4 (C11 or C12), 49.0 (C7), 48.2 (C11 or C12), 31.7 (C10), 24.7 (C8), 22.5 (C9); HRMS (ESI$^+$): calculated for C$_{12}$H$_{15}$N$_2$O$_3$: 235.1077, found [M+H—HCl]$^+$: 235.1078.

Example 27a—N-Boc 4-(hydroxymethyl)cytisine (121)

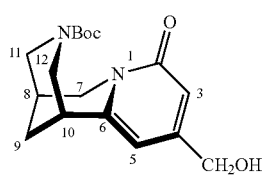

121

To a solution of N-Boc-4-methyl ester-cytisine 119 (350 mg, 1.00 mmol) in THF (4 mL) was added LiAlH$_4$ (1.0 M in Et$_2$O) dropwise at −78° C. during 5 min. and the reaction mixture was stirred for 3.5 h. EtOAc (2 mL) was added dropwise followed by the addition of a saturated Rochelle's salt solution (10 mL). The reaction mixture was stirred for 30 min, and the aqueous phase was extracted with EtOAc (3×25 mL). The combined organic phases were dried over MgSO$_4$, filtered and concentrated. Purification by flash column chromatography [DCM/MeOH (2% MeOH to 5% MeOH)] yielded 121 (194 mg, 62%) as a colourless foam.

mp: 201-203° C., colourless solid (toluene); 1H NMR (500 MHz, CDCl$_3$, δ$_H$): 6.49 (s, 1H, C3-H), 6.16 (s, 1H, C5-H), 4.55 (s, 2H, C14-H), 4.28-4.16 (m, 3H, C7-H, C11-H, C12-H), 3.86 (dd, 1H, J=6.5, 16.0 Hz, C7-H), 3.19-2.92 (m, 3H, C11-H, C12-H, C10-H), 2.45 (s, 1H, C8-H), 1.99 (m, 2H, C9-H), 1.41-1.18 (m, 9H, Boc). $^{13}$C NMR (125 MHz, CDCl$_3$, δ$_C$): 163.5 (CO), 154.6 (C6), 153.5 (C4), 112.7 (C3), 104.5 (C5), 80.6, 80.5 (C11, C12), 63.2 (C13), 48.8 (C7), 34.9 (C8), 28.0 (3C, Boc), 27.6 (C10), 26.2 (C9). The quaternary carbon of the boc group has not been found.

Example 27b—(−)4-(Hydroxymethyl)cytisine hydrochloride salt (122)

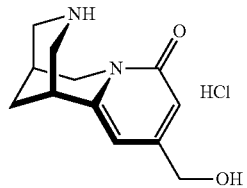

122

Following the general procedure A, N-Boc 4-hydroxymethylcytisine 121 (0.60 mmol) gave alcohol 122 (120 mg, 90%) as a colourless solid.

mp: >200° C., colourless solid; [α]$_D^{23}$=−24 [c 0.5, MeOH]; FTIR v$_{max}$/cm$^{-1}$ (neat): 3292, 2726, 2323, 1643, 1571; $^1$H NMR (500 MHz, D$_2$O, δ$_H$): 6.50 (s, 1H, C3-H), 6.47 (s, 1H, C5-H), 4.50 (s, 2H, C14-H), 4.10 (d, 1H, J=15.0 Hz, C7-H), 3.96 (dd, 1H, J=15.0, 6.0 Hz, C7-H), 3.48-3.31 (m, δ$_H$, C11-H C12-H C10-H), 2.77 (s, 1H, C8-H), 2.11-1.99 (m, 2H, C9-H); $^{13}$C NMR (125 MHz, D$_2$O, δ$_C$): 164.8 (CO), 156.1 (C4), 147.0 (C6), 112.5 (C3), 108.4 (C5), 61.5 (C13), 49.6 (C7), 48.5, 48.3 (C11, C12), 31.5 (C10), 24.7 (C8), 22.6 (C9); m/z (ESI$^+$): 224 [M+H—HCl]$^+$; HRMS (ESI$^+$): calculated for C$_{12}$H$_{16}$N$_2$O$_2$: 224.1757, found [M+H—HCl]$^+$: 224.1758.

Example 28a—N-Boc 4-(4-(Trifluoromethyl)benzyl)oxycytisine (123)

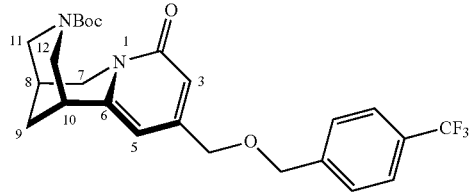

123

To a solution of the alcohol 121 (240 mg, 0.75 mmol) in dry THF (7.5 mL) was added NaH (33 mg, 1.1 eq., 60% dispersion in mineral oil) and the mixture was stirred at 0° C. After 30 min, TBAI (14 mg, 0.05 eq.) and 4-(trifluoromethyl) benzyl bromide (358 mg, 2 eq.) were added. The reaction was allowed to warm up to r.t. and stirred for 18 h. The reaction was quenched with water (10 mL) and the aqueous phase was extracted with EtOAc (3×15 mL). The combined organic layers were dried over MgSO$_4$, filtered and concentrated in vacuo. The crude reaction mixture was purified by flash column chromatography on silica gel [DCM/MeOH (1% MeOH)] to give 123 (250 mg, 71%) as colourless solid, which was used in the next step without further purification.

FTIR $v_{max}$/cm$^{-1}$ (neat): 2975, 2931, 2864, 1686, 1660, 1545; $^1$H NMR (500 MHz, CDCl$_3$, $\delta_H$): 7.60 (d, 2H, J=8.5 Hz, C18-H), 7.46 (d, 2H, J=8.5 Hz, C17-H), 6.42 (s, 1H, C3-H), 6.06 (d, 1H, J=1.5 Hz, C5-H), 4.58 (s, 2H, CH$_2$), 4.37 (s, 2H, CH$_2$), 4.26-4.08 (m, 3H, C7-H, C11-H, C12-H), 3.80 (dd, 1H, J=15.0, 6.5 Hz, C7-H), 3.13-2.89 (m, 3H, C10-H, C11-H, C12-H), 2.40 (s, 1H, C8-H), 1.95 (m, 2H, C9-H), 1.39-1.12 (s, 9H, Boc); $^{13}$C NMR (125 MHz, CDCl$_3$, $\delta_C$): 163.4 (CO), 154.6 (CO), 149.9 (C4), 148.5 (C6), 141.7 (CF$_3$), 129.3 (q, J=33.8 Hz, Ar), 127.7 (2C, Ar), 125.4 (2C, Ar), 123.3 (Ar), 114.2 (C3), 104.5/103.7 (C5 rotamers), 80.4/79.4 (q Boc rotamers), 71.5 (CH$_2$), 70.5 (CH$_2$), 51.6/50.6/50.5/49.3 (C11, C12 rotamers), 48.8 (C7), 34.9 (C10), 28.1 (3C, Boc), 27.5 (C8), 26.2 (C9); HRMS (ESI$^+$): found [M+H]$^+$: 479.2142, calculated C$_{25}$H$_{30}$F$_3$N$_2$O$_4$: 479.2152.

Example 28b—(−)4-(4-(Trifluoromethyl)benzyl) oxycytisine (124)

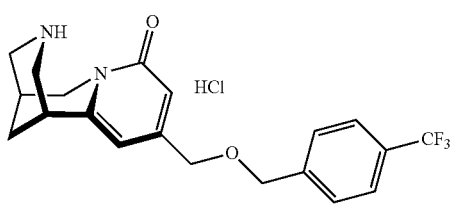

124

Eter 123 (0.25 g, 0.52 mmol) was converted into the HCl salt using the general procedure A yielding 124 (110 mg, 60%) as a colourless solid.

mp: >200° C., colourless solid; [α]$_D^{25}$=−18 [c 1.0, MeOH]; FTIR $v_{max}$/cm$^{-1}$ (neat): 2974, 2930, 1687, 1658, 1545, 1421; $^1$H NMR (500 MHz, D$_2$O, $\delta_H$): 7.65 (d, 2H, J=9.0 Hz, Ar), 7.50 (d, 2H, J=9.0, Ar), 6.47 (s, 1H, C3-H), 6.45 (s, 1H, C5-H), 4.64 (s, 2H, CH$_2$), 4.48 (s, 2H, CH$_2$), 4.07 (d, 1H, J=15.0 Hz, C7-H), 3.92 (dd, 1H, J=15.0, 6.0 Hz, C7-H), 3.47-3.28 (m, $\delta_H$, C10-H, C11-H, C12-H), 2.76 (s, 1H, C8-H), 2.07 (d, 1H, J=13.5 Hz, C9-H), 1.99 (d, 1H, J=13.5 Hz, C9-H); $^{13}$C NMR (125 MHz, D$_2$O, $\delta_C$): 164.8 (CO), 152.4 (C4), 146.9 (C6), 141.2 (CF$_3$), 129.6 (q, J=30 Hz, C—CF$_3$), 128.7 (2C, Ar), 125.4 (2C, Ar), 123.4 (Ar), 114.4 (C3), 108.7 (C5), 72.1 (CH$_2$), 70.0 (CH$_2$), 49.5, 48.3 (C11, C12), 48.6 (C7), 31.5 (C10), 24.8 (C8), 22.6 (C9); $^{19}$F NMR (376 MHz, D$_2$O, $\delta_F$): −63.2 (s); HRMS (ESI$^+$): calculated for C$_{20}$H$_{22}$F$_3$N$_2$O$_2$: 379.1628, found [M+H$^+$—HCl]$^+$: 379.1623.

Example 29a—N-Boc 4-Methyl cytisine (109)

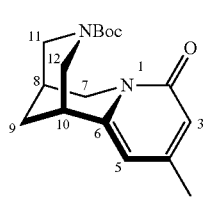

109

To a mixture of N-Boc-4-bromo-cytisine 61 (369 mg, 1.0 mmol) and PdCl$_2$(PPh$_3$)$_2$(35 mg, 5 mol %) in dry toluene (5.0 mL) was added Me$_4$Sn (0.35 mL, 2.5 mmol). The mixture was stirred at 100° C. for 24 h under N$_2$. The mixture was cooled to r.t., filtered through Celite,® washed with EtOAc (50 mL) and concentrated in vacuo. The crude was purified by flash column chromatography on silica gel [DCM/MeOH (97:3)] to give 109 (308 mg, quantitative) as a pale yellow solid with few impurities.

R$_f$: 0.26 [DCM/MeOH (5% MeOH)]; $^1$H NMR (400 MHz, CDCl$_3$, $\delta_H$): 6.19 (s, 1H, C3-H), 5.87 (s, 1H, C5-H), 4.30-4.06 (m, 3H, C7-H$_a$, C11-H, C12-H), 3.74 (dd, 1H, J=6.5, 15.5 Hz, C7-H$_b$), 3.06-2.90 (m, 3H, C10-H, C11-H, C12-H), 2.35 (s, 1H, C8-H), 2.09 (s, 3H, Me), 1.94-1.85 (m, 2H, C9-H), 1.29-1.16 (m, 9H, Boc); $^{13}$C NMR (100 MHz, CDCl$_3$, $\delta_C$): 163.5 (CO), 154.7/154.3 (CO Boc, rotamers), 150.4/149.8 (C4, rotamers), 148.0/147.5 (C6, rotamers), 116.0 (C3), 108.3/107.6 (C5, rotamers), 80.4/79.7 (q Boc, rotamers), 51.8/50.7/50.5/49.4 (C11, C12, rotamers), 48.6 (C7), 34.8 (C10), 28.1 (3C, Boc), 27.6 (C8), 26.3 (C9), 21.2 (Me); HRMS (ESI$^+$): calculated for C$_{17}$H$_{25}$N$_2$O$_3$: 305.1860, found [M+H]$^+$: 305.1864, calculated for C$_{17}$H$_{24}$N$_2$NaO$_3$: 327.1679, found [M+Na]$^+$: 327.1684.

Example 29b—(−)4-Methylcytisine hydrochloride salt (110)

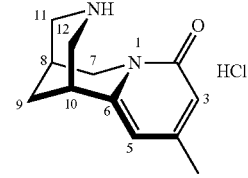

110

Following the general procedure A, N-Boc 4-Methylcytisine 109 (1.40 mmol) gave 110 (337 mg, quantitative) as a colourless solid.

mp: >200° C., colourless powder; [α]$_D^{26}$=−28 [c 0.5, MeOH]; FTIR $v_{max}$/cm$^{-1}$ (neat): 2714, 2604, 2038, 1727, 1643, 1567; $^1$H NMR (400 MHz, D$_2$O, $\delta_H$): 6.67 (s, 1H, C3-H), 6.59 (s, 1H, C5-H), 4.21 (d, 1H, J=15.5 Hz, C7-H$_a$), 4.07 (dd, 1H, J=6.5, 15.5 Hz, C7-H$_b$), 3.52-3.37 (m, $\delta_H$, C10-H, C11-H, C12-H), 2.83 (s, 1H, C8-H), 2.27 (s, 3H, Me), 2.16-2.13 (m, 2H, C9-H); $^{13}$C NMR (100 MHz, D$_2$O, $\delta_C$): 163.3 (CO), 156.0 (C4), 146.5 (C6), 114.6 (C3), 114.5 (C5), 49.3 (C11 or C12), 49.0 (C7), 48.1 (C11 or C12), 31.2 (C10), 24.7 (C8), 22.4 (C9), 20.4 (Me); HRMS (ESI$^+$): calculated for C$_{12}$H$_{17}$N$_2$O: 205.1335, found [M+H$^+$—HCl]$^+$: 205.1336.

Example 30a—(−)N-Boc 4-Vinylcytisine (115)

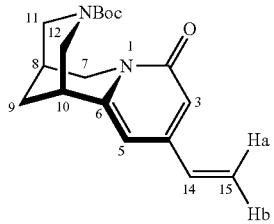

115

A mixture of N-Boc-4-bromo-cytisine 61 (369 mg, 1.0 mmol), 2, 4, 6-trivinylcyclotriboroxane pyridine complex (194 mg, 1.2 mmol), $K_2CO_3$ (276, 2.0 mmol) and $PdCl_2(PPh_3)_2$ (35 mg, 5 mol %) in dioxane/$H_2O$ (8:2) (5.0 mL) was stirred at 90° C. for 24 h under $N_2$. The mixture was cooled to r.t., filtered through Celite,® and washed with EtOAc (50 mL). The organic layer was washed with water (10 mL), brine (10 mL), dried over $Na_2SO_4$, filtered and concentrated in vacuo. The crude reaction mixture was purified by flash column chromatography on silica gel [DCM/MeOH (97:3)] to give 115 (271 mg, 86%) as a pale yellow foam, which was used in the next step without further purification.

$R_f$: 0.22 [DCM/MeOH (5% MeOH)]; $^1$H NMR (400 MHz, CDCl$_3$, $\delta_H$): 6.44 (s, 1H, C14-H), 6.32 (s, 1H, C3-H), 6.14 (s, 1H, C5-H), 5.77 (d, 1H, J=17.5 Hz, C15-H$_A$), 5.39 (d, 1H, J=11.0 Hz, C15-HB), 4.33-4.10 (m, 3H, C7-H$_a$, C11-H, C12-H), 3.77 (dd, 1H, J=6.5, 15.5 Hz, C7-H$_b$), 3.09-2.89 (m, 3H, C10-H, C11-H, C12-H), 2.38 (s, 1H, C8-H), 1.97-1.88 (m, 2H, C9-H), 1.30-1.15 (m, 9H, Boc); $^{13}$C NMR (100 MHz, CDCl$_3$, $\delta_C$): 163.8 (CO), 154.6/154.3 (CO Boc, rotamers), 148.6/148.2 (C6, rotamers), 147.1/146.9 (C4, rotamers), 134.8 (C14), 118.9 (C15), 114.7 (C3), 102.9/102.2 (C5, rotamers), 80.4/79.7 (q Boc, rotamers), 51.9/50.7/50.4/49.3 (C11, C12, rotamers), 48.8 (C7), 35.0 (C10), 28.1 (3C, Boc), 27.6 (C8), 26.3 (C9); HRMS (ESI$^+$): calculated for $C_{18}H_{25}N_2O_3$: 317.1860, found [M+H]$^+$: 317.1844, calculated for $C_{18}H_{24}N_2NaO_3$: 339.1679, found [M+Na]$^+$: 339.1665.

Example 30b—(+)4-Vinylcytisine hydrochloride salt (116)

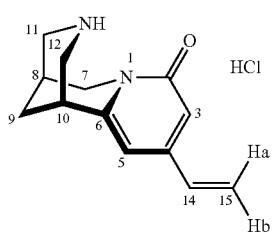

116

Following the general procedure B, N-Boc-4-Vinyl-cytisine 115 (271 mg, 0.86 mmol) gave 116 (214 mg, 99%) as a colourless solid.

mp: >200° C., colourless powder; $[\alpha]_D^{26}$=+18 [c 0.5, MeOH]; FTIR $v_{max}$/cm$^{-1}$ (neat): 3376, 2938, 2717, 2574, 2386, 1643, 1552; $^1$H NMR (400 MHz, D$_2$O, $\delta_H$): 6.82 (d, 1H, J=1.5 Hz, C3-H), 6.63-6.55 (m, 2H, C5-H, C14-H), 6.03 (d, 1H, J=17.5 Hz, C15-H$_A$), 5.60 (d, 1H, J=11.0 Hz, C15-HB), 4.16 (d, 1H, J=15.5 Hz, C7-H$_a$), 4.00 (dd, 1H, J=6.5, 15.5 Hz, C7-H$_b$), 3.52-3.37 (m, $\delta_H$, C10-H, C11-H, C12-H), 2.83 (s, 1H, C8-H), 2.18-2.04 (m, 2H, C9-H); $^{13}$C NMR (100 MHz, D$_2$O, $\delta_C$): 164.5 (CO), 150.3 (C4), 146.8 (C6), 133.2 (C14), 122.0 (C15), 113.2 (C5), 108.0 (C3), 49.4 (C11 or C12), 48.8 (C7), 48.1 (C11 or C12), 31.5 (C10), 24.7 (C8), 22.6 (C9); HRMS (ESI$^+$): calculated for $C_{13}H_{17}N_2O$: 217.1335, found [M+H—HCl]$^+$: 217.1332.

Example 31a—N-Boc 4-Ethylcytisine (117)

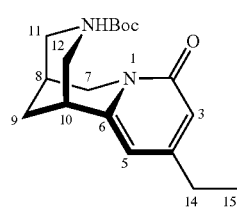

117

To a solution of 4-vinyl-N-Boc-cytisine 115 (353 mg, 1.1 mmol) in methanol (22 mL) was added Pd/C 10% w/w (35 mg). The reaction vessel was placed under vacuum and backfilled with hydrogen three times. The mixture was stirred at r.t. for 24 h under 1 atm of $H_2$. The mixture was filtered through Celite,® washed with EtOAc (50 mL) and concentrated in vacuo to give 117 (337 mg, 95%) as an off-white solid.

$R_f$: 0.17 [DCM/MeOH (5% MeOH)]; $^1$H NMR (400 MHz, CDCl$_3$, $\delta_H$): 6.22 (s, 1H, C3-H), 5.88 (s, 1H, C5-H), 4.33-4.30 (m, 3H, C7-H$_a$, C11-H, C12-H), 3.74 (dd, 1H, J=6.5, 15.5 Hz, C7-H$_b$), 3.05-2.91 (m, 3H, C10-H, C11-H, C12-H), 2.41-2.34 (m, 3H, C8-H, C14-H), 1.94-1.85 (m, 2H, C9-H), 1.28-1.14 (m, 12H, C15-H, Boc); $^{13}$C NMR (100 MHz, CDCl$_3$, $\delta_C$): 163.8 (CO), 156.0/155.5 (CO Boc, rotamers), 154.7/154.3 (C4, rotamers), 148.1/147.6 (C6, rotamers), 114.5 (C3), 107.3/106.4 (C5, rotamers), 80.3/79.7 (q Boc, rotamers), 51.7/50.7/50.5/49.3 (C11, C12, rotamers), 48.7 (C7), 34.8 (C10), 28.1 (3C, Boc), 27.6 (C8), 26.5 (C14), 26.3 (C9), 13.7/13.3 (C15, rotamers); HRMS (ESI$^+$): calculated for $C_{18}H_{27}N_2O_3$: 319.2016, found [M+H]$^+$: 319.2015, calculated for $C_{18}H_{26}N_2NaO_3$: 341.1836, found [M+Na]$^+$: 341.1840.

Example 31b—(−)4-Ethylcytisine hydrochloride salt (118)

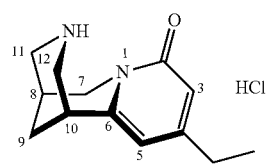

118

Following the general procedure A, N-Boc-4-ethyl-cytisine 117 (0.92 mmol) gave 118 (227 mg, 97%) as a colourless solid.

mp: >200° C., colourless powder; $[\alpha]_D^{26}$=−16 [c 0.5, MeOH]; FTIR $v_{max}$/cm$^{-1}$ (neat): 2724, 2603, 1716, 1634, 1555; $^1$H NMR (400 MHz, D$_2$O, $\delta_H$): 6.67 (d, 1H, J=1.5 Hz, C3-H), 6.57 (s, 1H, C5-H), 4.21 (d, 1H, J=15.5 Hz, C7-H$_a$), 4.06 (dd, 1H, J=6.5, 15.5 Hz, C7-H$_b$), 3.53-3.39 (m, $\delta_H$, C10-H, C11-H, C12-H), 2.83 (s, 1H, C8-H), 2.58 (q, 2H, J=7.5 Hz, C14-H), 2.17-2.06 (m, 2H, H$_9$), 1.16 (t, 3H, J=7.5 Hz, C15-H); $^{13}$C NMR (100 MHz, D$_2$O, $\delta_C$): 163.9 (CO), 161.1 (C4), 146.5 (C6), 113.5 (C5), 112.9 (C3), 49.4 (C11 or C12), 48.9 (C7), 48.1 (C11 or C12), 31.3 (C10), 27.7 (C14), 24.7 (C8), 22.5 (C9), 12.6 (C15); HRMS (ESI$^+$): calculated for C$_{13}$H$_{19}$N$_2$O: 219.1492, found [M+H$^+$—HCl]$^+$: 219.1494.

Example 32a—A-Boc 4-p-tolylcytisine (72)

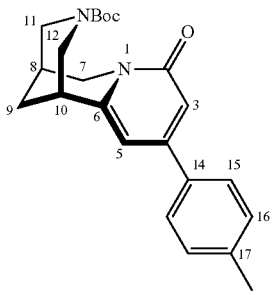

A Schienk tube was charged with N-Boc-4-bromo-cytisine 61 (370 mg, 1.0 mmol), potassium carbonate (250 mg, 1.8 eq.), tetrakis (triphenylphosphine) palladium (0) (58 mg, 5 mol %) and p-tolylboronic acid (160 mg, 1.2 eq. and a mixture of DME/water (5:1, 10 mL) was added. The reaction mixture was heated at 80° C. for 18 h. The solution was cooled and the solvent was removed in vacuo. The crude of the reaction was partitioned between water (15 mL) and DCM (15 mL), and the aqueous phase was extracted with DCM (3×15 mL). The combined organic phases were dried over MgSO$_4$, filtered and concentrated. Purification of the crude reaction mixture by flash column chromatography [DCM/MeOH (1.5% MeOH)] afforded 72 as a colourless solid. Recrystallization of the crude in hot toluene afforded 72 (260 mg, 71%) as a colourless foam.

mp: 194-195° C., colourless foam (toluene); FTIR v$_{max}$/cm$^{-1}$(neat): 2922, 1678, 1648, 1431; $^1$H NMR (500 MHz, CDCl$_3$, $\delta_H$): 7.44 (d, 2H, J=8.0 Hz, Ar), 7.20 (d, 2H, J=8.0 Hz, Ar), 6.62 (s, 1H, C3-H), 6.28 (s, 1H, C5-H), 4.41-4.13 (m, 3H, C11-H, C12-H, C7-H), 3.83 (dd, 1H, J=15.0, 6.5 Hz, C7-H), 3.15-2.91 (m, 3H, C11-H, C12-H, C10-H), 2.39 (s, 1H, C8-H), 2.36 (s, 3H, Me), 1.99 (d, 1H, J=13.5 Hz, C9-H), 1.93 (d, 1H, J=13.5 Hz, C9-H), 1.23 (s, 9H, Boc); $^{13}$C NMR (125 MHz, CDCl$_3$, $\delta_C$): 163.5 (CO), 154.3 (CO), 150.5 (C3), 148.6 (C5), 139.2 (Ar), 134.9 (Ar), 129.5 (2C, Ar), 126.5 (2C, Ar), 113.2 (C3), 104.6 (C5), 79.8 (q Boc), 51.0, 50.6 (C11, C12), 48.6 (C7), 35.0 (C10), 28.0 (3C, Boc), 27.7 (C8), 26.4 (C9), 21.1 (Me); HRMS (ESI$^+$): calculated for C$_{23}$H$_{29}$N$_2$O$_3$: 381.2173, found [M+H]$^+$: 381.2164; calculated for C$_{23}$H$_{28}$N$_2$NaO$_3$: 403.1992, found [M+Na]$^+$: 403.1984.

Example 32b—(+)4-p-Tolylcytisine (73)

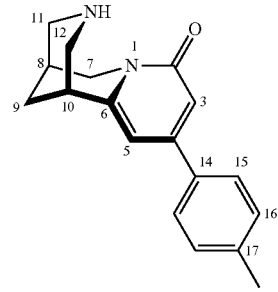

In a schlenk flask N-Boc-4-p-tolyl-cytisine 72 (270 mg, 0.71 mmol) was dissolved in DCM (7.0 mL) and TFA (0.3 mL, 10 eq.) was added. The reaction mixture was stirred for 18 h at r.t. Then, water (10 mL) was added over the reaction mixture and the aqueous phase was washed with DCM (3×15 mL). Then, ammonia solution (20 mL, 15% aq. sol.) was added and the aqueous phase was extracted with DCM (3×15 mL). The combined organic phases were dried over MgSO$_4$, filtered and concentrated, yielding 73 (140 mg, 74%) as a colourless solid. Recrystallization of the product in hot toluene afforded 73 (73 mg, 40%) as a colourless solid.

mp: >200° C., colourless solid (toluene); [α]$_D^{25}$=+44 [c 1.0, MeOH]; FTIR v$_{max}$/cm$^{-1}$ (neat): 1638, 1552, 1531; $^1$H NMR (500 MHz, MeOD, $\delta_H$): 7.56 (d, 2H, J=8.0 Hz, Ar), 7.27 (d, 2H, J=8.0 Hz, Ar), 6.65 (d, 1H, J=2.0 Hz, C3-H), 6.58 (d, 1H, J=2.0 Hz, C5-H), 4.10 (d, 1H, J=15.5 Hz, C7-H), 3.93 (dd, 1H, J=15.5, 7.0 Hz, C7-H), 3.10-2.97 (m, $\delta_H$, C11-H, C12-H, C10-H), 2.38 (s, 3H, Me), 2.34 (s, 1H, C8-H), 2.01 (m, 2H, C9-H); $^{13}$C NMR (125 MHz, MeOD, $\delta_C$): 164.5 (CO), 152.0 (C4), 151.4 (C6), 139.5 (Ar), 134.4 (Ar, 2C), 129.3 (Ar, 2C), 126.2 (Ar), 111.2 (C3), 105.6 (C5), 53.0, 51.9 (C11, C12), 49.5 (C7), 35.4 (C10), 27.6 (C8), 25.5 (C9), 19.7 (Me); HRMS (ESI$^+$): calculated for C$_{18}$H$_{21}$N$_2$O: 281.1648, found [M+H]$^+$: 281.1653.

Example 33a—N-Boc 4-(N-2-pyridone)cytisine (107)

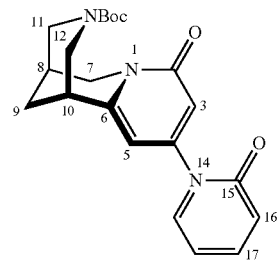

To a mixture of N-Boc-4-bromo-cytisine 61 (369 mg, 1.0 mmol), CuI (19 mg, 10 mol %), 2-hydroxypyridine (114 mg, 1.2 mmol) and K$_2$CO$_3$ (277 mg, 2.0 mmol) in dry toluene (5.0 mL) was added N,N'-dimethylethylenediamine (22 µL, 20 mol %). The mixture was heated at 110° C. for 24 h under nitrogen. More CuI (19 mg, 10 mol %) and N,N'-dimethylethylenediamine (DMEDA) (22 µL, 20 mol %) were added, and the stirring was carried on for 36 h. After cooling, the mixture was diluted with EtOAc (50 mL) then filtered through Celite.® The organic layer was washed with NH₄OH (2×10 mL, 15% aq.sol.). The combined aqueous layers were extracted with DCM (5×10 mL). The combined organic layers (EtOAc and DCM) were dried on Na₂SO₄, filtered and concentrated in vacuo. The crude reaction mixture was purified by flash column chromatography on silica gel [DCM/MeOH (95:5)] to give 107 (336 mg, 88%) as a pale yellow solid, which was used in the next step without further purification.

$R_f$: 0.17 [DCM/MeOH (5% MeOH)]; $^1$H NMR (400 MHz, CDCl₃, $δ_H$): 7.37-7.33 (m, 1H, C17-H), 7.22 (d, 1H, J=6.0 Hz, C19-H), 6.57 (d, 1H, J=9.0 Hz, C16-H), 6.33-6.32 (m, 2H, C3-H, C5-H), 6.24-6.21 (m, 1H, C18-H), 4.36-4.15 (m, 3H, C7-H$_a$, C11-H, C12-H), 3.76 (dd, 1H, J=6.5, 15.5 Hz, C7-H$_b$), 3.04-2.98 (m, 3H, C10-H, C11-H, C12-H), 2.41 (s, 1H, C8-H), 2.04-1.90 (m, 2H, C9-H), 1.31-1.24 (m, 9H, Boc); $^{13}$C NMR (125 MHz, CDCl₃, $δ_C$): 163.6 (CO py), 161.5 (CO), 154.7/154.4 (CO Boc, rotamers), 151.1 (C4), 149.7 (C6), 140.4 (C17), 136.7/136.2 (C19, rotamers), 122.3/122.0 (C16, rotamers), 113.0/112.7 (C3, rotamers), 106.7 (C18), 104.9/104.3 (C5, rotamers), 80.5/80.0 (q Boc, rotamers), 51.4/50.6/50.5/49.3 (C11, C12, rotamers), 49.1 (C7), 35.1 (C10), 28.1 (3C, Boc), 27.4 (C8), 26.0 (C9); HRMS (ESI+): calculated for C₂₁H₂₆N₃O₄: 384.1918, found [M+H]⁺: 384.1921, calculated for C₂₁H₂₅N₃NaO₄: 406.1737, found [M+Na]⁺: 406.1747.

Example 33b—(−)4-(N-2-pyridone)cytisine hydrochloride salt (108)

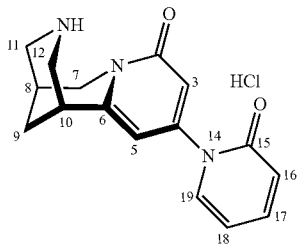

108

Following the general procedure B, N-Boc 4-(N-2-pyridone)-cytisine 107 (289 mg, 0.75 mol) gave 108 (182 mg, 76%) as a pale orange solid.

mp: >200° C., colourless powder (toluene); [α]$_D^{25}$=−20 [c 0.5, water]; FTIR ν$_{max}$/cm⁻¹ (neat): 2922, 2710, 2601, 1662, 1638, 1595; $^1$H NMR (400 MHz, D₂O, $δ_H$): 7.74-7.70 (m, 1H, C17-H), 7.60 (dd, 1H, J=1.5, 7.0 Hz, C19-H), 6.69-6.62 (m, 4H, C3-H, C5-H, C16-H, C18-H), 4.23 (d, 1H, J=15.5 Hz, C7-H$_a$), 4.07 (dd, 1H, J=6.5, 15.5 Hz, C7-H$_b$), 3.57-3.40 (m, $δ_H$, C10-H, C11-H, C12-H), 2.87 (s, 1H, C8-H), 2.20-2.10 (m, 2H, C9-H); $^{13}$C NMR (100 MHz, D₂O, $δ_C$): 165.1 (CO), 163.1 (CO py), 151.4 (C4), 148.8 (C6), 143.6 (C17), 137.3 (C19), 119.8 (C16), 114.3 (C3), 109.4 (C18), 108.0 (C5), 49.2 (C11 or C12), 48.9 (C7), 48.1 (C11 or C12), 31.7 (C10), 24.7 (C8), 22.4 (C9); HRMS (ESI⁺): calculated for C₁₆H₁₈N₃O₂: 284.1394, found [M+H−HCl]⁺: 284.1388.

Example 34a—N-Boc 4-(trimethylsilylacetylene)cytisine (125)

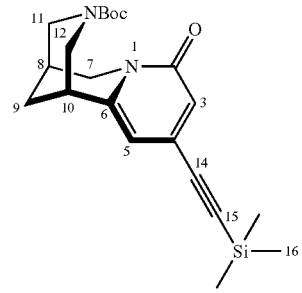

125

To a mixture of N-Boc-4-bromo-cytisine 61 (369 mg, 1.0 mmol), CuI (19 mg, 10 mol %) and PdCl₂(PPh₃)₂ (35 mg, 5 mol %) in dry THF (10.0 mL) was added i-Pr₂NH (0.42 mL, 3.0 mmol) followed by trimethylsilylacetylene (0.16 mL, 1.1 mmol). The mixture was stirred at r.t. for 24 h under nitrogen. The mixture was diluted with DCM (50 mL). The organic layer was washed with NH₄Cl (10 mL, sat. sol.), brine (10 mL), dried over Na₂SO₄, filtered and concentrated in vacuo. The crude was purified by flash column chromatography on silica gel [EtOAc] to give 125 (406 mg, quantitative) as a pale brown foam with few impurities (palladium catalyst). The product was used in the next step without further purification.

$R_f$: 0.21 [EtOAc]; FTIR ν$_{max}$/cm⁻¹ (neat): 2972, 2932, 1689, 1651, 1574; $^1$H NMR (400 MHz, CDCl₃, $δ_H$): 6.48 (s, 1H, C3-H), 6.05 (s, 1H, C5-H), 4.32-4.09 (m, 3H, C7-H$_a$, C11-H, C12-H), 3.78 (dd, 1H, J=6.5, 15.5 Hz, C7-H$_b$), 3.08-2.92 (m, 3H, C10-H, C11-H, C12-H), 2.38 (s, 1H, C8-H), 1.96-1.88 (m, 2H, C9-H), 1.30-1.23 (m, 9H, Boc), 0.21 (s, 9H, C16-H); $^{13}$C NMR (100 MHz, CDCl₃, $δ_C$): 162.7 (CO), 154.4 (CO Boc), 148.8, 148.5 (C6, C4), 119.7 (C3), 107.9, 107.3 (C5, rotamers), 107.9 (C14), 100.2 (C15), 80.4, 79.9 (q Boc, rotamers), 51.5, 50.5, 50.3, 49.3 (C11, C12, rotamers), 48.8 (C7), 34.7 (C10), 28.0 (3C, Boc), 27.5 (C8), 26.1 (C9), −0.35 (3C, C16); HRMS (ESI+): calculated for C₂₁H₃₁N₂O₃Si: 387.2098, found [M+H]⁺: 387.2094, calculated for C₂₁H₃₀N₂NaO₃Si: 409.1918, found [M+Na]⁺: 409.1910.

Example 34b—N-Boc 4-(acetylene)cytisine 126

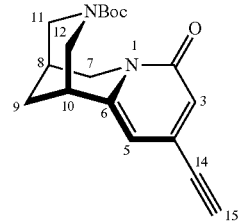

126

To a solution of N-Boc-4-(trimethylsilylacetylene)-cytisine 125 (379 mg, 0.98 mmol) in a mixture of MeOH (14 mL) and DCM (7 mL) was added $K_2CO_3$ (270 mg, 1.96 mmol). The mixture was stirred for 24 h. Water was added (10 mL) and the aqueous phase was extracted with DCM (3×20 mL). The combined organic layers were dried over $Na_2SO_4$, filtered and concentrated in vacuo. The crude was purified by flash column chromatography on silica gel [EtOAc] to give 126 (275 mg, 89%) as a white solid together with few impurities (palladium catalyst). The product was used in the next step without further purification.

$R_f$: 0.21 [EtOAc]; FTIR $v_{max}/cm^{-1}$ (neat): 3225, 2915, 2862, 1686, 1654, 1574; $^1$H NMR (400 MHz, CDCl$_3$, $\delta_H$): 6.52 (s, 1H, C3-H), 6.06 (s, 1H, C5-H), 4.31-4.09 (m, 3H, C7-H$_a$, C11-H, C12-H), 3.76 (dd, 1H, J=6.5, 15.5 Hz, C7-H$_b$), 3.23 (s, 1H, C15-H), 3.04-2.93 (m, 3H, C10-H, C11-H, C12-H), 2.38 (s, 1H, C8-H), 1.96-1.88 (m, 2H, C9-H), 1.30-1.21 (m, 9H, Boc); $^{13}$C NMR (100 MHz, CDCl$_3$, $\delta_C$): 162.5 (CO), 154.4/154.3 (CO Boc, rotamers), 149.3, 148.8 (C6, C4), 120.3 (C3), 107.8/107.1 (C5, rotamers), 82.1 (C15), 80.8 (C14), 80.3/79.9 (q Boc, rotamers), 51.6/50.5/50.2/49.3 (C11, C12, rotamers), 48.9 (C7), 34.7 (C10), 28.0 (3C, Boc), 27.4 (C8), 26.0 (C9); HRMS (ESI$^+$): calculated for $C_{18}H_{23}N_2O_3$: 315.1703, found [M+H]$^+$: 315.1696, calculated for $C_{18}H_{22}N_2NaO_3$: 337.1523, found [M+Na]$^+$: 337.1516.

Example 34c—(−)4-(acetylenyl)cytisine hydrochloride salt (127)

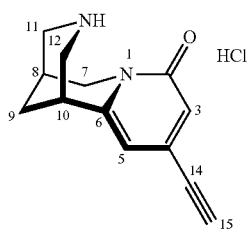

Following the general procedure B, N-Boc 4-(acetylene) cytisine 126 (0.77 mmol) gave 127 (150 mg, 78%) as a pale yellow solid.

mp: >200° C., pale yellow solid; $[\alpha]_D^{26}=-32$ [c 0.5, MeOH]; FTIR $v_{max}/cm^{-1}$ (neat): 2726, 2604, 1631, 1540; $^1$H NMR (400 MHz, D$_2$O, $\delta_H$): 6.55 (s, 1H, C3-H), 6.48 (s, 1H, C5-H), 4.00 (d, 1H, J=15.5 Hz, C7-H$_a$), 3.86 (dd, 1H, J=6.5, 15.5 Hz, C7-H$_b$), 3.74 (s, 1H, C15-H), 3.39-3.23 (m, $\delta_H$, C10-H, C11-H, C12-H), 2.70 (s, 1H, C8-H), 2.03-1.91 (m, 2H, C9-H); $^{13}$C NMR (100 MHz, D$_2$O, $\delta_C$): 164.0 (CO), 147.4 (C4), 135.0 (C6), 119.8 (C3), 111.9 (C5), 85.2 (C15), 79.7 (C14), 49.3 (C11 or C12), 48.8 (C7), 48.1 (C11 or C12), 31.4 (C10), 24.7 (C8), 22.4 (C9); HRMS (ESI$^+$): calculated for $C_{13}H_{15}N_2O$: 215.1179, found [M+H−HCl]$^+$: 215.1176.

Example 35a—N-Boc 4-(phenylacetylene)cytisine (128)

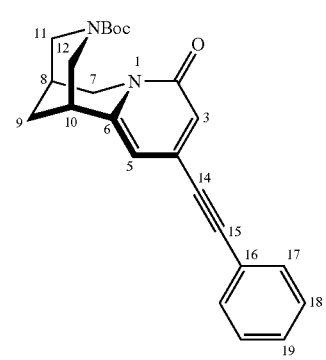

To a mixture of N-Boc 4-bromo cytisine 61 (369 mg, 1.0 mmol), CuI (38 mg, 20 mol %) and PdCl$_2$(PPh$_3$)$_2$ (70 mg, 10 mol %) in dry THF (5.0 mL) was added i-Pr$_2$NH (0.42 mL, 3.0 mmol) followed by phenylacetylene (0.22 mL, 2.0 mmol). The mixture was stirred at r.t. for 24 h under nitrogen. The mixture was diluted with EtOAc (50 mL). The organic layer was washed with NH$_4$Cl (10 mL, saturated solution), brine (10 mL), dried over Na$_2$SO$_4$, filtered and concentrated in vacuo. The crude was purified by flash column chromatography on silica gel [EtOAc] to give 128 (376 mg, 96%) as a pale brown foam with few impurities (palladium catalyst). The product was used in the next step without further purification.

$R_f$: 0.14 [EtOAc]; $^1$H NMR (400 MHz, CDCl$_3$, $\delta_H$): 7.50-7.48 (m, 2H, C17-H), 7.34-7.33 (m, 3H, C18-H, C19-H), 6.56 (s, 1H, C3-H), 6.13 (s, 1H, C5-H), 4.34-4.12 (m, 3H, C7-H$_a$, C11-H, C12-H), 3.79 (dd, 1H, J=6.5, 15.5 Hz, C7-H$_b$), 3.05-2.96 (m, 3H, C10-H, C11-H, C12-H), 2.40 (s, 1H, C8-H), 1.98-1.89 (m, 2H, C9-H), 1.32-1.23 (m, 9H, Boc); $^{13}$C NMR (100 MHz, CDCl$_3$, $\delta_C$): 162.7 (CO), 154.4 (CO Boc), 148.9/148.5 (C6, rotamers), 134.0/133.7 (C4, rotamers), 131.8 (C17, C21), 129.1 (C19), 128.4 (C18, C20), 122.1 (C16), 119.2 (C3), 107.8/107.1 (C5, rotamers), 94.2 (C15), 86.6 (C14), 80.4/79.9 (q Boc, rotamers), 51.6/50.5/50.4/49.3 (C11, C12, rotamers), 48.8 (C7), 34.8 (C10), 28.1 (3C, Boc), 27.5 (C8), 26.1 (C9); HRMS (ESI$^+$): calculated for $C_{24}H_{27}N_2O_3$: 391.2016, found [M+H]$^+$: 391.2024, calculated for $C_{24}H_{26}N_2NaO_3$: 413.1836, found [M+Na]$^+$: 413.1876.

Example 35b—(+)4-(phenylacetylene)cytisine hydrochloride salt (129)

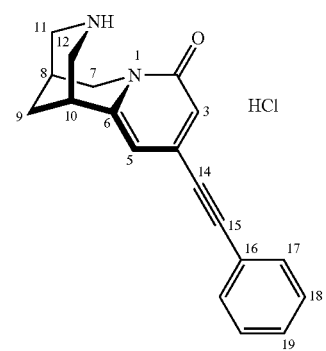

Following the general procedure B, N-Boc-4-(phenylacetylene)-cytisine 128 (0.88 mmol) gave 129 (267 mg, 92%) as a pale yellow solid.

mp: >200° C., pale yellow solid; $[\alpha]_D^{26}$=+42 [c 0.5, MeOH]; FTIR $v_{max}$/cm$^{-1}$ (neat): 2925, 2717, 2214, 1630, 1537; $^1$H NMR (400 MHz, MeOH, $\delta_H$): 7.51-7.49 (m, 2H, C17-H), 7.41-7.33 (m, 3H, C18-H, C19-H), 7.00 (s, 1H, C3-H), 6.89 (s, 1H, C5-H), 4.33 (d, 1H, J=15.5 Hz, C7-H$_a$), 4.17 (dd, 1H, J=6.5, 15.5 Hz, C7-H$_b$), 3.56-3.22 (m, $\delta_H$, C10-H, C11-H, C12-H), 2.78 (s, 1H, C8-H), 2.17 (d, 1H, J=13.0 Hz, C9-H$_a$), 2.07 (d, 1H, J=13.0 Hz, C9-H$_b$); $^{13}$C NMR (100 MHz, MeOD, $\delta_C$): 163.8 (CO), 150.3 (C6), 139.4 (C4), 133.2 (C17, C21), 131.4 (C19), 129.9 (C18, C20), 122.4 (C16), 117.5 (C5), 116.6 (C3), 99.4 (C15), 86.3 (C14), 51.4 (C7), 50.3 (C11, C12), 33.0 (C10), 26.4 (C8), 23.6 (C9); HRMS (ESI$^+$): calculated for C$_{19}$H$_{19}$N$_2$O: 291.1492, found [M+H—HCl]$^+$: 291.1486.

Example 36a—N-Boc 4-(E-2-propenoate methyl ester)cytisine (111)

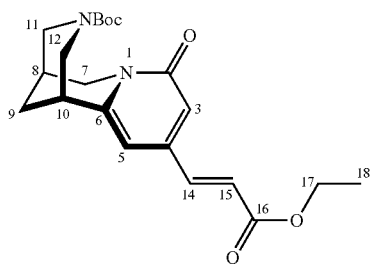

To a mixture of N-Boc 4-bromocytisine 61 (369 mg, 1.0 mmol) and Pd$_2$(dba)$_3$ (12 mg, 2.5 mol %) in dry dioxane (5.0 mL) was added Cy$_2$NMe (0.2 mL, 1.1 mmol), P(t-Bu)$_3$ (0.1M in dioxane, 0.5 mL, 5 mol %) and ethyl acrylate (0.2 mL, 2.0 mmol). The mixture was stirred at r.t. for 24 h under nitrogen. Pd$_2$(dba)$_3$ (12 mg, 2.5 mol %), P(t-Bu)$_3$ (0.1M in dioxane, 0.50 mL, 5 mol %) and ethyl acrylate (0.2 mL, 2.0 mmol) were added again and the mixture stirred for 24 h more. The mixture was filtered through Celite,® washed with EtOAc and concentrated in vacuo. The crude was purified by flash column chromatography on silica gel [DCM/MeOH (97:3)] to give 111 (321 mg, 83%) as a pale yellow solid.

R$_f$: 0.26 [DCM/MeOH (5% MeOH)]; mp: >200° C., colourless powder; FTIR $v_{max}$/cm$^{-1}$ (neat): 2973, 2934, 1723, 1679, 1655, 1640, 1567, 1431; $^1$H NMR (400 MHz, CDCl$_3$, $\delta_H$): 7.35 (d, 1H, J=16.0 Hz, C14-H), 6.47 (s, 1H, C3-H), 6.38 (d, 1H, J=16.0 Hz, C15-H), 6.15 (s, 1H, C5-H), 4.34-4.07 (m, $\delta_H$, C7-H$_a$, C11-H, C12-H, C17-H), 3.77 (dd, 1H, J=6.5, 15.5 Hz, C7-H$_b$), 3.10-2.90 (m, 3H, C10-H, C11-H, C12-H), 2.39 (s, 1H, C8-H), 1.98-1.90 (m, 2H, C9-H), 1.31-1.14 (m, 12H, Boc, C18-H); $^{13}$C NMR (125 MHz, CDCl$_3$, $\delta_C$): 165.9 (C16), 163.3 (CO), 154.5/154.2 (CO Boc, rotamers), 149.8/148.9 (C6, rotamers), 144.1/143.8 (C4, rotamers), 141.7 (C14), 123.1 (C15), 117.4 (C3), 102.9/102.0 (C5, rotamers), 80.4/79.8 (q Boc, rotamers), 60.9 (C17), 51.7/50.6/50.4/49.2 (C11, C12, rotamers), 49.0 (C7), 35.1 (C10), 28.1 (3C, Boc), 27.5 (C8), 26.2 (C9), 14.2 (C18); HRMS (ESI$^+$): calculated for C$_{21}$H$_{29}$N$_2$O$_5$: 389.2071, found [M+H]$^+$: 389.2059, calculated for C$_{21}$H$_{28}$N$_2$NaO$_5$: 411.1890, found [M+Na]$^+$: 411.1880.

Example 36b—(+)4-(E-2-propenoate methyl ester)cytisine hydrochloride salt (112)

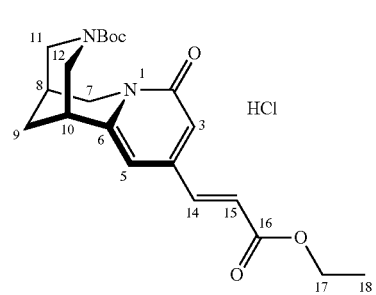

Following the general procedure B, 111 (1.00 mmol) gave 112 (300 mg, 92%) as a pale yellow solid.

mp: >200° C., pale yellow solid; $[\alpha]_D^{26}$=+22 [c 0.5, MeOH]; FTIR $v_{max}$/cm$^{-1}$ (neat): 2943, 2751, 1706, 1655, 1637, 1570; $^1$H NMR (400 MHz, D$_2$O, $\delta_H$): 7.28 (d, 1H, J=16.0 Hz, C14-H), 6.62 (d, 1H, J=1.5 Hz, C3-H), 6.47-6.43 (m, 2H, C5-H, C15-H), 4.11 (q, 2H, J=7.0 Hz, C17-H), 4.00 (d, 1H, J=16.0 Hz, C7-H$_a$), 3.83 (dd, 1H, J=6.5, 15.5 Hz, C7-H$_b$), 3.40-3.24 (m, $\delta_H$, C10-H, C11-H, C12-H), 2.69 (s, 1H, C8-H), 2.05-1.92 (m, 2H, C9-H), 1.16 (t, 3H, J=7.0 Hz, C18-H); $^{13}$C NMR (100 MHz, D$_2$O, $\delta_C$): 167.9 (C16), 164.7 (CO), 147.2 (C4), 146.2 (C6), 141.1 (C14), 124.0 (C15), 116.9 (C3), 106.9 (C5), 62.1 (C17), 49.4 (C11 or C12), 48.7 (C7), 48.2 (C11 or C12), 31.6 (C10), 24.7 (C8), 22.6 (C9), 13.2 (C18); HRMS (ESI$^+$): calculated for C$_{16}$H$_{21}$N$_2$O$_3$: 289.1547, found [M+H$^+$—HCl]$^+$: 289.1561.

Example 37a—N-Boc-4-(E-(2-phenylethenyl))cytisine (113)

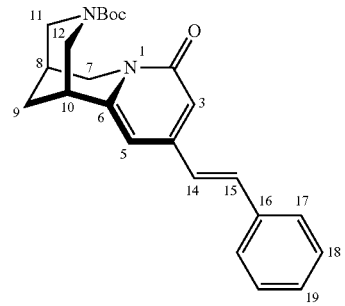

To a mixture of N-Boc-4-bromo-cytisine 61 (369 mg, 1.0 mmol) and Pd$_2$(dba)$_3$ (12 mg, 2.5 mol %) in dry dioxane (5.0 mL) was added Cy$_2$NMe (0.2 mL, 1.1 mmol), P(t-Bu)$_3$ (0.1M in dioxane, 0.50 mL, 5 mol %) and styrene (0.2 mL, 2.0 mmol). The mixture was stirred at r.t. for 24 h under nitrogen. Pd$_2$(dba)$_3$ (12 mg, 2.5 mol %), P(t-Bu)$_3$ (0.1M in dioxane, 0.50 mL, 5 mol %) and styrene (0.2 mL, 2.0 mmol) were added again and the mixture stirred for 24 h more. The mixture was filtered through Celite®, washed with EtOAc and concentrated in vacuo. The crude was purified by flash column chromatography on silica gel [DCM/MeOH (97:3)] to give 113 (373 mg, 95%) as a pale yellow foam. The product was used in the next step without further purification.

$R_f$: 0.19 [DCM/MeOH (5% MeOH)]; $^1$H NMR (400 MHz, CDCl$_3$, $\delta_H$): 7.49-7.47 (m, 2H, C17-H, C21-H), 7.36-7.25 (m, 3H, C18-H, C19-H, C20-H), 7.11 (d, 1H, J=16.0 Hz, C15-H), 6.81 (s, 1H, C14-H), 6.43 (s, 1H, C3-H), 6.28 (s, 1H, C5-H), 4.39-4.13 (m, 3H, C7-H$_a$, C11-H, C12-H), 3.80 (dd, 1H, J=6.5, 15.5 Hz, C7-H$_b$), 3.12-2.92 (m, 3H, C10-H, C11-H, C12-H), 2.39 (s, 1H, C8-H), 2.00-1.91 (m, 2H, C9-H), 1.37-1.17 (m, 9H, Boc); $^{13}$C NMR (125 MHz, CDCl$_3$, $\delta_C$): 163.8 (CO), 154.6/154.3 (CO Boc, rotamers), 148.5/148.1 (C6, rotamers), 147.0/146.7 (C4, rotamers), 136.1 (C16), 133.4/133.3 (C15, rotamers), 128.8 (C18, C20), 128.7 (C19), 127.0 (C17, C21), 126.0 (C14), 114.6 (C3), 103.1/102.3 (C5, rotamers), 80.3/79.7 (q Boc, rotamers), 51.8/50.6/50.5/49.3 (C11, C12, rotamers), 48.7 (C7), 35.0 (C10), 28.1 (3C, Boc), 27.5 (C8), 26.3 (C9); HRMS (ESI$^+$) calculated for C$_{24}$H$_{29}$N$_2$O$_3$: 393.2173, found [M+H]$^+$: 393.2173, calculated for C$_{24}$H$_{28}$N$_2$NaO$_3$: 415.1992, found [M+Na]$^+$: 415.1991.

Example 37b—(+)4-(E-(2-phenylethenyl))cytisine hydrochloride salt (114)

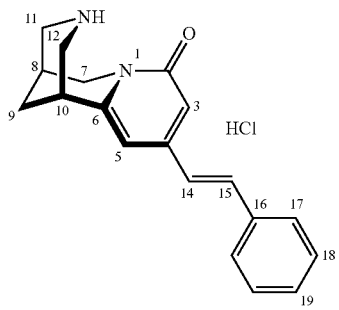

114

Following the general procedure B, 113 (0.88 mmol) gave 114 (259 mg, 89%) as an off-white solid.

mp: >200° C., off-white solid; [α]$_D^{26}$=+90 [c 0.5, MeOH]; FTIR $v_{max}$/cm$^{-1}$ (neat): 2925, 2713, 2606, 1629, 1553; $^1$H NMR (400 MHz, D$_2$O, $\delta_H$): 7.26-7.16 (m, $\delta_H$, C17-H, C18-H, C19-H), 6.99 (d, 1H, J=16.5 Hz, C15-H), 6.59 (d, 1H, J=16.5 Hz, C14-H), 6.51 (s, 1H, C3-H), 6.23 (s, 1H, C5-H), 3.87 (d, 1H, J=15.5 Hz, C7-H$_a$), 3.54 (dd, 1H, J=6.5, 15.5 Hz, C7-H$_b$), 3.31-3.16 (m, $\delta_H$, C10-H, C11-H, C12-H), 2.56 (s, 1H, C8-H), 1.91 (d, 1H, J=13.5 Hz, C9-H), 1.67 (d, 1H, J=13.5 Hz, C9-H); $^{13}$C NMR (100 MHz, D$_2$O, $\delta_C$): 164.1 (CO), 149.8 (C16), 146.3 (C6), 135.4 (C15), 135.3 (C14), 129.2 (C19), 128.8 (C18, C20), 127.2 (C17, C21), 124.3 (C4), 113.1 (C3), 107.7 (C5), 49.5 (C11 or C12), 48.5 (C7), 48.1 (C11 or C12), 31.4 (C10), 24.6 (C8), 22.5 (C9); HRMS (ESI$^+$): calculated for C$_{19}$H$_{21}$N$_2$O: 293.1648, found [M+H—HCl]$^+$: 293.1655.

Example 38a—N-Boc 4-(1-(4-phenyl)-MH-1, 2, 3-triazolyl)cytisine (134)

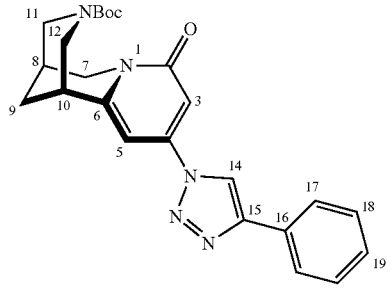

134

To a mixture of N-Boc-4-bromo-cytisine 61 (369 mg, 1.00 mmol), NaN$_3$ (130 mg, 2.0 mmol), sodium ascorbate (20 mg, 10 mol %) and CuI (19 mg, 10 mol %) in EtOH/H$_2$O (7:3) (5.0 mL) was added DMEDA (22 µL, 20 mol %) then phenylacetylene (132 µL, 1.2 mmol). The mixture was stirred at 50° C. for 24 h under nitrogen. The mixture was cooled to r.t., diluted with NH$_4$OH solution (20 mL, 15% aq.sol.) and then extracted with EtOAc (3×50 mL). The combined organic layers were washed with brine (20 mL), dried over Na$_2$SO$_4$, filtered and concentrated in vacuo. The crude (86-93% conversion based on $^1$H NMR) was purified by flash column chromatography on silica gel [EtOAc then DCM/MeOH/NH$_4$OH (97:3:0.1)] to give 134 (214 mg, 49%) as an off-white solid, which was used in the next step without further purification.

$R_f$: 0.11 [EtOAc]; $^1$H NMR (400 MHz, CDCl$_3$, $\delta_H$): 8.22 (s, 1H, C14-H), 7.89 (d, 2H, J=7.0 Hz, C17-H, C21-H), 7.47-7.44 (m, 2H, C18-H, C20-H), 7.39-7.36 (m, 1H, C19-H), 6.91 (s, 1H, C3-H), 6.70 (s, 1H, C5-H), 4.39-4.20 (m, 3H, C7-H$_a$, C11-H, C12-H), 3.87 (dd, 1H, J=6.5, 15.5 Hz, C7-H$_b$), 3.15-3.00 (m, 3H, C10-H, C11-H, C12-H), 2.47 (s, 1H, C8-H), 2.06-1.98 (m, 2H, C9-H), 1.34-1.19 (m, 9H, Boc); $^{13}$C NMR (125 MHz, CDCl$_3$, $\delta_C$): 163.3 (CO), 154.6 (CO Boc), 152.0/151.5 (C6, rotamers), 149.0 (C15), 145.0 (C4), 129.7 (C16), 129.1 (C18, C20), 128.9 (C19), 126.1 (C17, C21), 116.9 (C14), 103.8 (C5), 98.3/97.8 (C3, rotamers), 80.7/80.1 (q Boc, rotamers), 51.6/50.8/50.3/49.4 (C11, C12, rotamers), 49.3 (C7), 35.5 (C10), 28.2 (3C, Boc), 27.5 (C8), 26.1 (C9); HRMS (ESI$^+$): calculated for C$_{24}$H$_{27}$N$_5$NaO$_3$: 456.2006, found [M+Na]$^+$: 456.1993.

Example 38b—(+)4-(1-(4-phenyl)-AH-1, 2, 3-triazolyl)cytisine dihydrochloride salt (135)

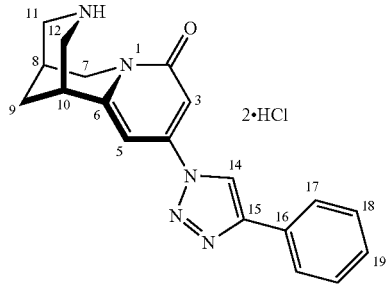

135

Following the general procedure B, N-Boc-4-((4-phenyl)-NH-1, 2, 3, triazole)-cytisine 134 (0.46 mmol) gave 135 (151 mg, 81%) as a colourless solid.

mp: >200° C., colourless powder; $[\alpha]_D^{22}$=+36 [c 0.5, water]; FTIR $v_{max}$/cm$^{-1}$ (neat): 3436, 3034, 2565, 1656, 1563; $^1$H NMR (400 MHz, DMSO-d$_6$, $\delta_H$): 9.50 (s, 1H, C14-H), 8.58 (s, 1H, NH), 7.94 (d, 2H, J=7.5 Hz, C17-H, C21-H), 7.50 (app t, 2H, J=7.5 Hz, C18-H, C20-H), 7.40 (app t, 1H, J=7.5 Hz, C19-H), 7.10 (d, 1H, J=2.5 Hz, C3-H), 6.93 (d, 1H, J=2.5 Hz, C5-H), 4.01 (d, 1H, J=15.5 Hz, C7-H$_a$), 3.85 (dd, 1H, J=6.5, 15.5 Hz, C7-H$_b$), 3.46 (s, 1H, C10-H), 3.35-3.16 (m, 4H, C11-H, C12-H), 2.67 (s, 1H, C8-H), 2.07 (d, 1H, J=13.0 Hz, C9-H), 1.94 (d, 1H, J=13.0 Hz, C9-H); $^{13}$C NMR (100 MHz, DMSO-d$_6$, $\delta_C$): 162.7 (CO), 150.2 (C4), 147.8 (C15), 144.4 (C6), 129.7 (C19), 129.1 (C18, C20), 128.6 (C16), 125.5 (C17, C21), 119.5 (C14), 103.8 (C5), 97.6 (C3), 48.4 (C11 or C12), 48.1 (C7), 47.4 (C11 or C12), 31.6 (C10), 24.5 (C8), 22.7 (C9); HRMS (ESI$^+$): calculated for C$_{19}$H$_{20}$NSO: 334.1662, found [M+H$^+$-2HCl]$^+$: 334.1676; calculated for C$_{19}$H$_{19}$N$_5$NaO: 356.1482, found [M+Na-2HCl]$^+$: 356.1503.

Example 39a—N-Boc 4-(1, 2, 3-triazol-1-yl)methyl pivalate)cytisine (131)

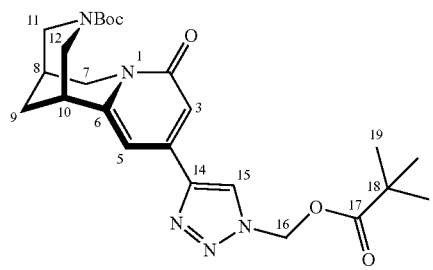

To a solution of N-Boc-4-(acetylene)-cytisine 126 (544 mg, 1.73 mmol) in a mixture of tBuOH/H$_2$O (1:1) (8.6 mL) were successively added azidomethyl pivalate (0.3 mL, 2.08 mmol), CuSO$_{4.5}$ H$_2$O (22 mg, 5 mol %) and sodium ascorbate (102 mg, 30 mol %). The mixture was stirred at r.t. for 48 h. The mixture was diluted with NH$_4$OH (10 mL, 15% aq. sol.) then extracted with EtOAc (3×20 mL). The combined organic layers were washed with brine (20 mL), dried over Na$_2$SO$_4$, filtered and concentrated in vacuo. The crude was purified by flash column chromatography on silica gel [DCM/MeOH/NH$_4$OH (95:5:0.1)] to give 131 (722 mg, 89%) with few impurities as a pale yellow oil, which was used in the next step without further purification.

R$_f$: 0.08 [DCM/MeOH (5% MeOH)]; $^1$H NMR (500 MHz, CDCl$_3$, $\delta_H$): 8.07 (s, 1H, C15-H), 6.78-6.72 (m, 2H, C3-H, C5-H), 6.26 (s, 2H, C16-H), 4.37-4.16 (m, 3H, C7-H$_a$, C11-H, C12-H), 3.84 (dd, 1H, J=6.5, 15.5 Hz, C7-H$_b$), 3.08-2.95 (m, 3H, C10-H, C11-H, C12-H), 2.43 (s, 1H, C8-H), 2.02-1.94 (m, 2H, C9-H), 1.32-1.13 (m, 18H, Boc, C19-H); $^{13}$C NMR (125 MHz, CDCl$_3$, $\delta_C$): 178.0 (C17), 163.5 (CO), 154.7/154.5 (CO Boc, rotamers), 150.1/149.5 (C4, rotamers), 145.5 (C14), 140.1/139.9 (C6, rotamers), 123.2/123.0 (C15, rotamers), 112.4 (C3), 103.5/102.9 (C5, rotamers), 80.5/79.9 (q Boc, rotamers), 69.9 (C16), 51.7/50.8/50.4/49.4 (C11, C12, rotamers), 49.0 (C7), 38.9 (C18), 35.1 (C10), 28.2 (3C, Boc), 27.7 (C8), 26.9 (3C, C19), 26.3 (C9); HRMS (ESI$^+$): calculated for C$_{24}$H$_{34}$N$_5$O$_5$: 472.2554, found [M+H]$^+$: 472.2551; calculated for C$_{24}$H$_{33}$N$_5$NaO$_5$: 494.2374, found [M+Na]$^+$: 494.2371.

Example 39b—N-Boc4-(HM-1, 2, 3-triazolyl))-cytisine (132)

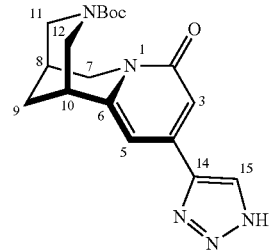

To a solution of N-Boc-4-(1, 2, 3-triazol-1-yl)methyl pivalate)-cytisine 131 (688 mg, 1.46 mmol) in MeOH (3.2 mL) was added NaOH (3.2 mL, 1M aq. sol.). The mixture was stirred at r.t. for 12 h. The reaction was neutralized with HCl (3.2 mL, 1M aq. sol.), diluted with water (30 mL) and extracted with EtOAc (5×20 mL). The combined organic layers were washed with brine (20 mL), dried over Na$_2$SO$_4$, filtered and concentrated in vacuo. The crude was purified by flash column chromatography on silica gel [DCM/MeOH/NH$_4$OH (97:3:0.1)] to give 132 (461 mg, 88%) as an off-white solid.

R$_f$: 0.32 [DCM/MeOH (10% MeOH)]; $^1$H NMR (500 MHz, CDCl$_3$, $\delta_H$): 8.01-7.82 (m, 1H, C15-H), 7.03-6.92 (m, 1H, C3-H), 6.77 (s, 1H, C5-H), 4.39-4.15 (m, 3H, C7-H$_a$, C11-H, C12-H), 3.91 (dd, 1H, J=6.5, 15.5 Hz, C7-H$_b$), 3.15-2.99 (m, 3H, C10-H, C11-H, C12-H), 2.47 (s, 1H, C8-H), 2.06-1.97 (m, 2H, C9-H), 1.36-1.14 (m, 9H, Boc); $^{13}$C NMR (125 MHz, CDCl$_3$, $\delta_C$): 164.0 (CO), 155.0/154.7 (CO Boc, rotamers), 149.9/149.1 (C4, rotamers), 143.6 (C14), 141.2 (C6), 128.7/128.3 (C15, rotamers), 112.4 (C3), 104.7/104.2 (C5, rotamers), 81.3/80.1 (q Boc, rotamers), 51.8/50.9/50.8/49.5 (C11, C12, rotamers), 49.2 (C7), 35.2 (C10), 28.2 (3C, Boc), 27.3 (C8), 26.3 (C9); HRMS (ESI$^+$): calculated for C$_{18}$H$_{24}$N$_5$O$_3$: 358.1874, found [M+H]$^+$: 358.1874; calculated for C$_{18}$H$_{23}$N$_5$NaO$_3$: 380.1693, found [M+Na]$^+$: 380.1703.

Example 39c—(+)4-(NH-1, 2, 3-triazolyl))cytisine dihydrochloride salt 133 (A)

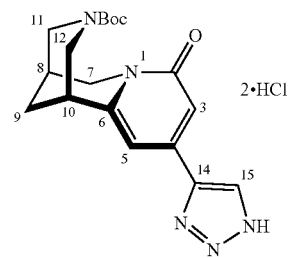

Following the general procedure A, N-Boc-4-(NH-1, 2, 3-triazole)-cytisine 132 (1.22 mmol) was deprotected and converted into the HCl salt using the general procedure A yielding 133 (352 mg, 87%) as an colourless solid.

mp: >200° C., colourless powder; $[\alpha]_D^{22}$=+32 [c 0.5, water]; FTIR $v_{max}$/cm$^{-1}$ (neat): 3094, 2905, 2723, 2396, 1651, 1552; 1H NMR (400 MHz, D$_2$O, $\delta_H$): 8.19 (s, 1H, C15 H), 6.81 (d, 1H, J=1.5 Hz, C3-H), 6.68 (d, 1H, J=1.5 Hz, C5-H), 4.13 (d, 1H, J=15.5 Hz, C7-H$_a$), 3.90 (dd, 1H, J=6.5, 15.5 Hz, C7-H$_b$), 3.54-3.38 (m, $\delta_H$, C10-H, C11-H, C12-H), 2.83 (s, 1H, C8-H), 2.16 (d, 1H, J=13.5 Hz, C9-H), 2.05 (d, 1H, J=13.5 Hz, C9-H); $^{13}$C NMR (100 MHz, D$_2$O, $\delta_C$): 164.2 (CO), 147.9 (C6), 142.1 (C14), 141.5 (C4), 125.4 (C15), 111.2 (C5), 107.0 (C3), 49.3 (C11 or C12), 48.7 (C7), 48.2 (C11 or C12), 31.6 (C10), 24.7 (C8), 22.5 (C9); HRMS (ESI$^+$): calculated for C$_{13}$H$_{16}$N$_5$O: 258.1349, found [M+H$^+$-2HCl]$^+$: 258.1342; calculated for C$_{13}$H$_{15}$N$_5$NaO: 280.1169, found [M+Na-2HCl]$^+$: 280.1163.

Example 40—(+)4-(N-ethylamino)cytisine (87)

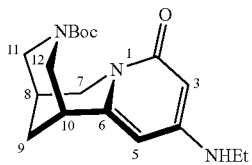

A mixture of N-Boc-4-bromo-cytisine 61 (369 mg, 1.0 mmol) and copper (7 mg, 10 mol %) in EtNH$_2$ (2.0 mL, 2.0 M in THF) was stirred in water (1 mL) at 100° C. for 24 h in a sealed tube. The mixture was cooled and extracted with DCM (5×10 mL). The combined organic layers were dried over MgSO$_4$, filtered and concentrated in vacuo. The crude was purified by flash column chromatography on silica gel [DCM/MeOH (6% MeOH)] to give 87 (102 mg, 42%) as an off-white solid.

Mp: ≥200° C.; $[\alpha]_D^{23}$=+50 [c 0.5, MeOH]; FTIR $v_{max}$/cm$^{-1}$(neat): 3269, 2901, 2868,1639,1532; $^1$H NMR (500 MHz, D$_2$O, $\delta_H$): 5.92 (d, 1H, J=2.0 Hz, C3-H), 5.54 (d, 1H, J=2.0 Hz, C5-H), 3.92 (d, 1H, J=15.0 Hz, C7-H), 3.79 (dd, 1H, J=6.0, 15.0 Hz, C7-H), 3.13 (q, 2H, J=7.5 Hz, CH$_2$), 3.06-2.90 (m, $\delta_H$, C10-H, C11-H, C12-H), 2.33 (s, 1H, C8-H), 1.98 (d, 1H, J=13.5 Hz, C9-H), 1.91 (d, 1H, J=13.5 Hz, C9-H), 1.10 (t, 3H, J=7.5 Hz, CH$_3$); $^{13}$C NMR (125 MHz, D$_2$O, $\delta_C$): 165.3 (CO), 157.1 (C4), 150.7 (C6), 99.5 (C3), 89.4 (C5), 52.0, 50.8 (C11, C12), 48.9 (C7), 36.8 (CH$_2$), 34.5 (C10), 26.8 (C8), 24.9 (C9), 13.0 (CH$_3$); HRMS (ESI$^+$): calculated C$_{13}$H$_{20}$N$_3$O: 234.1601, found [M+H]$^+$: 234.1609.

Example 41—(+)4-(N-isopropylamino)cytisine 88

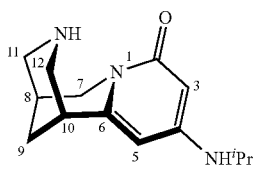

A mixture of N-Boc-4-bromo-cytisine 61 (369 mg, 1.0 mmol) and copper (7 mg, 10 mol %) in 40% aq. iPrH$_2$ (2.0 mL) was stirred at 100° C. for 24 h in a sealed tube. The mixture was cooled and extracted with DCM (5×10 mL). The combined organic layers were dried over Na$_2$SO$_4$, filtered and concentrated in vacuo. The crude was purified by flash column chromatography on silica gel [DCM/MeOH (6% MeOH)] to give 88 (88 mg, 33%) as an off-white solid.

Mp: 200° C.; $[\alpha]_D^{24}$=+50 [c 0.5, MeOH]; FTIR $v_{max}$/cm$^{-1}$(neat): 2969, 1639, 1535,1276; $^1$H NMR (500 MHz, MeOD, $\delta_H$): 5.76 (d, J=2.5 Hz, 1H, C3-H), 5.46 (d, J=2.5 Hz, 1H, C5-H), 3.97 (d, J=15.0 Hz, 1H, C7-H), 3.79 (dd, J=15.0, 6.0 Hz, 1H, C7-H), 3.57 (hept, J=6.5 Hz, 1H, C13-H), 3.07-2.92 (m, 4H, C11-H C12-H), 2.83 (s, 1H, C10-H), 2.27 (s, 1H, C8-H), 1.95 (m, 2H, C9-H), 1.20 (dd, J=6.5, 2.0 Hz, 6H, C14-H); $^{13}$C NMR (125 MHz, MeOD, 6c): 165.5 (CO), 155.7 (C4), 149.7 (C6), 98.7 (C3), 89.1 (C5), 52.7, 51.6 (C11 C12), 48.5 (C7), 43.1 (C13), 35.1 (C10), 27.6 (C8), 25.6 (C9), 21.0 (2C, C14); HRMS (ESI$^+$): calculated C$_{14}$H$_{22}$N$_3$O: 248.1757, found [M+H$^+$—HCl]$^+$: 248.1766.

Example 42a—N-Boc 4-cyanocytisine (139)

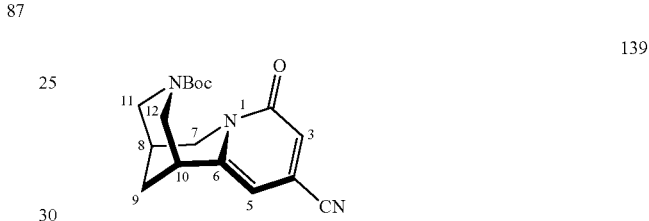

A Schlenk tube was charged with N-Boc-4-bromo-cytisine 61 (1.85 g, 5.00 mmol), Pd((PPh$_3$)$_4$) (230 mg, 0.20 mmol), and zinc cyanide (350 mg, 3.00 mmol), and placed under nitrogen. DMF (6.2 mL) was added and the reaction mixture was heated at 80° C. for 18 h. The reaction mixture was cooled and the solvent was removed in vacuo. Purification of the crude reaction mixture by flash column chromatography [DCM:MeOH (1% MeOH)] afforded 139 (1.6 g, 99%) as a colourless solid.

R$_f$: 0.7 [DCM/MeOH (4% MeOH)]; mp: 153-156° C., colourless powder (toluene); FTIR $v_{max}$/cm$^{-1}$ (neat): 2973, 2233 (weak peak as conjugated, CN band), 1658, 1572; 1H NMR (500 MHz, CDCl$_3$, $\delta_H$, 52.0° C.): 6.74 (s, 1H, C3-H), 6.18 (s, 1H, C5-H), 4.42-4.07 (m, 3H, C11-H, C12-H, C7-H), 3.81 (dd, 1H, J=6.5, 16.0 Hz, C7-H), 3.19-2.91 (m, 3H, C11-H, C12-H, C10-H), 2.48 (s, 1H, C8-H), 1.98 (s, 2H, C9-H), 1.38-1.17 (s, 9H, Boc); $^{13}$C NMR (125 MHz, CDCl$_3$, $\delta_C$, 52.0° C.): 161.3 (CO), 154.1 (C4), 151.7 (C6), 121.9 (C3), 115.9 (CN), 104.3 (C5), 80.5 (q Boc), 50.1, 49.8 (C11, C12), 49.2 (C7), 34.8 (C10), 28.4 (3C, Boc), 27.4 (C8), 25.8 (C9). (Carbonyl carbon of the Boc group not observed); HRMS (ESI$^+$): calculated C$_{17}$H$_{21}$N$_3$NaO: 338.1475, found [M+Na]$^+$: 338.1467.

Example 43—(−)4-Cyanocytisine (140)

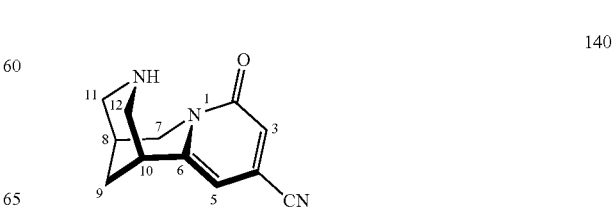

In a Schlenk flask, N-Boc-4-cyano-cytisine 139 (140 mg, 0.46 mmol) was dissolved in DCM (3.0 mL, 0.1 M) and TFA (0.3 mL, 10 eq.) was added. The solution was stirred at r.t. for 16 h. Water was added (10 mL) and the aqueous phase was washed with DCM (3×20 mL). Ammonia was added (10 mL, 15% aq. sol.) and the aqueous phase was extracted with DCM (4×20 mL). The combined organic layers were dried over MgSO$_4$, filtered and concentrated, yielding 140 (86 mg, 86%) as a colourless solid.

mp: 161-163° C., colourless needles (toluene); $[\alpha]_D^{23}$=−53 [c 0.66, MeOH]; (FTIR $v_{max}$/cm$^{-1}$ (neat): 2233 (weak peak as conjugated, CN band), 1649, 1581; $^1$H NMR (500 MHz, MeOD, $\delta_H$): 6.87 (d, 1H, J=2.0 Hz, C3-H), 6.59 (d, 1H, J=2.0 Hz, C5-H), 4.19 (d, 1H, J=16.0 Hz, C7-H), 4.01 (dd, 1H, J=16.0, 7.0 Hz, C7-H), 3.52-3.35 (m, $\delta_H$, C10-H, C11-H, C12-H), 2.78 (s, 1H, C8-H), 2.18 (d, 1H, J=14.0 Hz, C9-H), 2.10 (d, 1H, J=14.0 Hz, C9-H); $^{13}$C NMR (125 MHz, MeOD, $\delta_C$): 161.6 (C2), 154.1 (C6), 122.7 (C4), 121.4 (C3), 116.4 (C13), 104.1 (C5), 53.7, 52.9 (C11, C12), 50.4 (C7), 35.7 (C10), 27.5 (C8), 25.9 (C9); HRMS (ESI$^+$): calculated C$_{12}$H$_{14}$N$_3$O: 216.1131, found [M+H]$^+$: 216.1129.

Example 44a—A-Boc-4-(carboxyamido)cytisine (141)

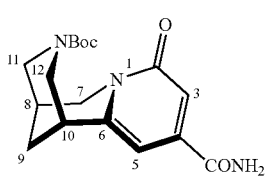

141

To a solution of N-Boc-4-cyano-cytisine 139 (320 mg, 1.0 mmol) in an equimolar mixture of EtOH/water (5 mL) was added NaBH$_4$ (33 mg, 0.75 mmol) and the reaction mixture was stirred at 75° C. for 18 h. The reaction mixture was cooled to r.t., and quenched with water (5 mL). Ethanol was removed in vacuo. Then, the aqueous phase was extracted with DCM (3×15 mL) and the combined organic phases were dried over MgSO$_4$, filtered and concentrated. Purification of the crude reaction mixture by flash column chromatography [DCM/MeOH (from 2% to 4% MeOH)] yielded 141 (150 mg, 46%) as a colourless solid which was recrystallized from toluene.

R$_f$: 0.43 [DCM/MeOH (4% MeOH)]; mp: >200° C., colourless powder; FTIR $v_{max}$/cm$^{-1}$ (neat): 3317, 3148, 2974, 1690, 1639, 1562; $^1$H NMR (500 MHz, MeOD, $\delta_H$, 52° C.): 6.83 (s, 1H, C3-H), 6.69 (s, 1H, C5-H), 4.35-4.31 (s, 1H, C11-H), 4.20-4.16 (br s, 1H, C7-H), 4.14 (s, 1H, C12-H), 3.84 (dd, 1H, J=6.0, 15.0 Hz, C7-H), 3.27-2.98 (m, 3H, C10-H C11-H C12-H), 2.49 (s, 1H, C8-H), 2.12-1.97 (m, 2H, C9-H), 1.41-1.06 (s, 9H, Boc); $^{13}$C NMR (125 MHz, MeOD, $\delta_C$, 52° C.): 167.8 (CO amide), 163.4 (CO pyridone), 154.6 (CO Boc), 150.8 (C6), 144.4 (C4), 114.3 (C3), 104.6 (C5), 80.2 (q Boc), 67.4 (C11, C12), 49.3 (C7), 35.2 (C10), 27.7 (C8), 26.9 (3C, Boc), 25.1 (C9); HRMS (ESI$^+$): calculated C$_{17}$H$_{24}$N$_3$O$_4$: 334.1761, found [M+H]$^+$: 334.1753; calculated C$_{17}$H$_{23}$N$_3$NaO$_4$: 356.1581, found [M+Na]$^+$: 356.1570.

Example 44b—(−)4-(carboxyamido)cytisine hydrochloride salt (142)

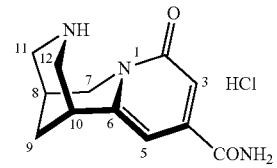

142

Following the general procedure A, N-Boc-4-amido-cytisine 141 (0.44 mmol) gave 142 (90 mg, 88%) as a colourless solid.

mp: >200° C., colourless powder; $[\alpha]_D^{25}$=−2 [c 0.5, MeOH]; FTIR $v_{max}$/cm$^{-1}$ (neat): 1646, 1543; $^1$H NMR (500 MHz, MeOD, $\delta_H$): 6.92 (d, 1H, J=2.0 Hz, C3-H), 6.75 (d, 1H, J=2.0 Hz, C3-H), 4.21 (d, 1H, J=16.0 Hz, C7-H), 4.05 (dd, 1H, J=16.0, 6.5 Hz, C7-H), 3.53-3.41 (m, $\delta_H$, C11-H, C12-H, C10-H), 2.82 (s, 1H, C8-H), 2.20 (d, 1H, J=13.5 Hz, C9-H), 2.12 (d, 1H, J=13.5 Hz, C9-H); $^{13}$C NMR (125 MHz, MeOD, 5c): 167.7 (CO CONH$_2$), 164.1 (CO), 147.4 (C4), 144.8 (C6), 115.8 (C3), 105.3 (C5), 49.4 (C7), 32.1 (C10), 25.2 (C8), 22.8 (C9), (C11 and C12 are under the signal of the solvent); HRMS (ESI$^+$): calculated C$_{12}$H$_{16}$N$_3$O$_2$: 234.1237, found [M+H−HCl]$^+$: 234.1229.

Example 45a—N-Boc 4-(Aminomethyl)cytisine (143)

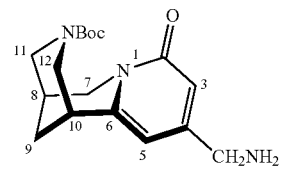

143

Raney Ni (0.3 mL, slurry in water) was added over a solution of N-Boc-4-cyano-cytisine 139 (320 mg, 1.0 mmol) and KOH (84 mg, 1.5 mmol) in EtOH (10 mL, 0.1 M). The reaction vessel was placed under vacuum and backfilled with hydrogen three times, and stirred at r.t. for 18 h. The reaction mixture was filtered through Celite® and the crude reaction mixture was concentrated. Purification by flash column chromatography [DCM:MeOH (10% MeOH)+0.1% ammonia (35% aq. sol.)] yielded amine 143 (260 mg, 82%) as a colourless solid.

R$_f$: 0.22 [DCM:MeOH (10% MeOH)]; mp: 157-160° C., colourless powder (toluene); FTIR $v_{max}$/cm$^{-1}$ (neat): 2928, 1673, 1644, 1542; $^1$H NMR (500 MHz, MeOD, $^6$H, 52° C.): 6.40 (s, 1H, C3-H), 6.34 (d, 1H, J=2.0 Hz, C5-H), 4.27 (s, 1H, C11-H), 4.16 (s, 1H, C12-H), 4.12 (s, 1H, C7-H), 3.30 (dd, 1H, J=6.0, 15.0 Hz, C7-H), 3.67 (s, 2H, C13-H), 3.22-3.04 (m, 3H, C11-H, C12-H, C10-H), 2.45 (s, 1H, C8-H), 2.08-1.99 (m, 2H, C9-H), 1.42-1.11 (s, 9H, Boc); $^{13}$C NMR (125 MHz, MeOD, $\delta_C$, 52° C.): 164.3 (CO), 155.6 (CO), 154.7 (C6), 149.3 (C4), 112.3 (C3), 106.5 (C5), 79.97 (q Boc), 50.3 (C11, C12), 48.9 (C7), 44.1 (C13), 34.9 (C10), 27.7 (C8), 27.0 (3C, Boc), 25.4 (C9); HRMS (ESI$^+$): calculated for $C_{17}H_{25}N_3O_3$: 319.1896, found $[M+H]^+$: 320.1958, calculated for $C_{17}H_{24}N_3NaO_3$: 342.1794, found $[M+Na]^+$: 342.1783.

Example 45b—(−)4-(aminomethyl)cytisine dihydrochloride salt (144)

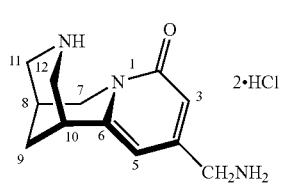

Following the general procedure A, N-Boc-4-methyl-amino-cytisine 143 (0.76 mmol) was converted into the HCl salt yielding 144 (150 mg, 89%) as a colourless solid.

mp: >200° C., colourless powder; $[\alpha]_D^{26}$=−46 [c 0.5, MeOH]; FTIR $v_{max}$/cm$^{-1}$ (neat): 2789, 1653, 1518; $^1$H NMR (500 MHz, $D_2O$, $\delta_H$): 6.50 (s, 1H, C3-H), 6.46 (s, 1H, C5-H), 4.07 (d, 1H, J=16.0 Hz, C7-H), 4.02 (s, 2H, C13-H), 3.94 (dd, 1H, J=16.0, 6.5 Hz, C7-H), 3.45-3.29 (m, $\delta_H$, C11-H, C12-H, C8-H), 2.75 (s, 1H, C10-H), 2.06 (d, 1H, J=13.6 Hz, C9-H), 2.00 (d, 1H, J=13.6 Hz, C9-H); $^{13}$C NMR (125 MHz, $D_2O$, $^6$c): 164.6 (CO), 148.0 (C4), 16.9 (C6), 115.4 (C3), 108.5 (C5), 48.7 (C7), 49.3, 48.2 (C11, C12), 41.2 (C13), 31.5 (C8), 24.8 (C10), 22.4 (C9); HRMS (ESI$^+$): calculated $C_{12}H_{18}N_3O$: 220.1444, found [M+H—HCl]$^+$: 220.1441.

Example 46a—N-Boc 4-(N-Boc aminomethyl)cytisine

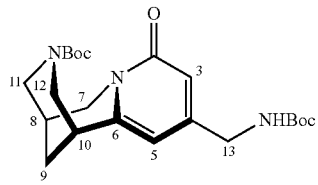

To a solution of N-Boc-4-aminomethyl-cytisine 143 (264 mg, 0.83 mmol) in THF (8 mL) were added $Boc_2O$ (0.2 mL, 0.91 mmol) and triethylamine (0.16 mL, 1.16 mmol), and the reaction mixture was stirred for 18 h at r.t. Then, water (15 mL) was added and the aqueous phase was extracted with DCM (3×25 mL). The combined organic phases were dried over $MgSO_4$, filtered, and concentrated. Purification by flash column chromatography [DCM:MeOH (3% MeOH)] yielded N-Boc-4-(N-Boc-aminomethyl)-cytisine (280 mg, 82%) as a colourless oil.

FTIR $v_{max}$/cm$^{-1}$ (neat): 3316, 2975, 1683, 1653, 1546, 1423; $^1$H NMR (500 MHz, $CDCl_3$, $\delta_H$, 52° C.): 6.33 (s, 1H, C3-H), 5.98 (d, 1H, J=2.0 Hz, C5-H), 4.82 (s, 1H, NH), 4.36-4.07 (m, $\delta_H$, C7-H, C11-H, C12-H, C13-H), 3.81 (dd, 1H, J=5.5, 15.5 Hz, C7-H), 3.10-2.94 (m, 3H, C11-H, C12-H, C10-H), 2.41 (s, 1H, C8-H), 1.99 (d, 1H, J=13.5 Hz, C9-H), 1.92 (d, 1H, J=13.5 Hz, C9-H), 1.46 (s, 9H, Boc), 1.38-1.23 (s, 9H, Boc); $^{13}$C NMR (125 MHz, $CDCl_3$, $\delta c$, 52° C.): 166.4 (CO), 155.8 (CO Boc), 154.5 (CO Boc), 150.9 (C6), 148.7 (C4), 113.8 (C3), 104.4 (C5), 79.6 (2C, q Boc), 50.8, 50.5 (C11, C12), 48.7 (C7), 43.5 (C13), 35.0 (C10), 28.3, 28.0 (6C, Boc), 27.6 (C8), 26.3 (C9); HRMS (ESI+): calculated for $C22H_{34}N_3O_5$: 420.2492, found $[M+H]^+$: 420.2490.

Example 46b—(−)4-((N-methyl)aminomethyl)cytisine (152)

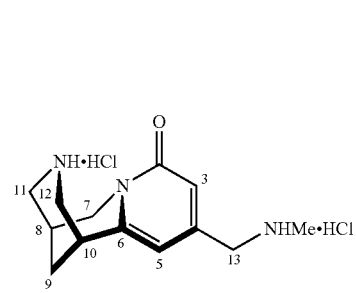

To a solution of N-Boc-4-(N-Boc-aminomethyl)-cytisine (255 mg, 0.61 mmol) in THF (6.0 mL) was added NaH (17 mg, 0.70 mmol, 60% dispersion oil) and the solution was stirred for 30 min. Iodomethane (0.05 mL, 0.70 mmol) was added and the reaction mixture was stirred for 18 h at r.t. The crude was distributed between water (10 mL) and EtOAc (10 mL) and the aqueous phase was extracted with EtOAc (3×10 mL). The combined organic phases were dried over $MgSO_4$, filtered, and concentrated. The resulting compound was deprotected and converted into its HCl salt using the general procedure A, yielding 152 (89 mg, 65%) as a colourless solid.

mp: >200° C.; FTIR $v_{max}$/cm$^{-1}$ (neat): 2728, 1651, 1548; $^1$H NMR (500 MHz, $D_2O$, $\delta_H$): 6.57 (s, 1H, C3-H), 6.51 (s, 1H, C5-H), 4.14-4.05 (m, 3H, C7-H, $CH_2$), 3.97 (dd, J=6.0, 15.5 Hz, 1H, C7-H), 3.50-3.31 (m, $\delta_H$, C10-H, C11-H, C12-H), 2.79 (s, 1H, C10-H), 2.70 (s, 3H, NHMe), 2.13-2.00 (m, 2H, C9-H); $^{13}$C NMR (125 MHz, $D_2O$, $\delta_C$): 164.5 (CO), 148.3 (C6), 145.0 (C4), 117.2 (C3), 109.1 (C5), 50.4 ($CH_2$), 49.4, 48.1 (C11, C12), 48.7 (C7), 32.6 (NHMe), 31.7 (C10), 24.8 (C8), 22.5 (C9); HRMS (ESI+): calculated $C_{13}H_{20}N_3O$: 234.1601, found [M+H—HCl]$^+$: 234.1595.

Example 47a—Tert-butyl (1R, 5R)-10-(hydroxymethyl)-8-oxo-1,5,6,8-tetrahydro-2H-1,5-methanopyrido[1,2-a][1,5]diazocine-3(4H)-carboxylate (153)

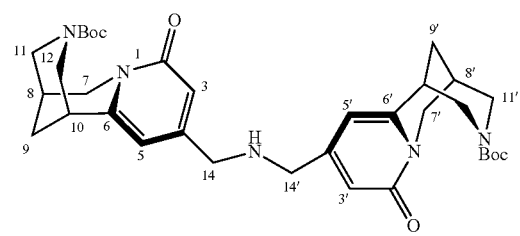

N-Boc-4-cyano-cytisine 139 (200 mg, 0.63 mmol) was dissolved in a mixture of pyridine, acetic acid and water in a proportion (2:1:1) and NaH$_2$PO$_2$ (340 mg, 3.27 mmol) and Ni Raney (1.0 mL, slurry in water) were added. The reaction mixture was stirred at 50° C. for 6 h. The solution was filtered through Celite® and concentrated. The crude was distributed between water (15 mL) and DCM (15 mL) and the aqueous phase was extracted with DCM (3×25 mL). The combined organic phases were dried over MgSO$_4$, filtered and concentrated. Purification of the crude reaction mixture by column chromatography [DCM/MeOH (4% MeOH)] yielded 153 (170 mg, 86%) as a colourless pale-yellow solid.

R$_f$: 0.10 [DCM/MeOH (4% MeOH)]; mp: 75-78° C., pale-yellow solid (toluene); FTIR $v_{max}$/cm$^{-1}$ (neat): 2928, 1651, 1543, 1423; $^1$H NMR (500 MHz, MeOD, $^6$H, 52° C.): 6.44 (s, 2H, C3-H), 6.39 (d, 2H, J=2.0 Hz, C5-H), 4.31 (m, 6H, C11-H, C12-H, NH), 4.15 (d, 2H, J=15.0 Hz, C7-H), 3.80 (dd, 2H, J=15.0, 6.5 Hz, C7-H), 3.64 (s, 4H, C14-H), 3.13 (s, $\delta_H$, C10-H, C11-H, C12-H), 2.45 (s, 2H, C8-H), 2.05 (m, 4H, C9-H), 1.28 (s, 18H, Boc); $^{13}$C NMR (125 MHz, MeOD, $\delta_C$, 52° C.): 164.1 (2×CO), 157.7 (2×CO), 153.3 (2×C4), 149.7 (2×C6), 113.6 (2×C3), 107.3 (2×C5), 80.0 (2×q Boc), 50.8, 50.7 (4×C11, C12), 50.6 (2×C14), 48.8 (2×C7), 35.0 (2×C10), 27.7 (2×C8), 27.0 (6×C Boc), 25.4 (2×C9); HRMS (ESI$^+$): calculated for C$_{34}$H$_{48}$N$_5$O$_6$: 622.3605, found [M+H]$^+$: 622.3591, calculated for C$_{34}$H$_{46}$NaN$_5$O$_6$: 644.3424, found [M+Na]$^+$: 644.3412.

Example 47b —Amine bis(cytisine) derivative (154)

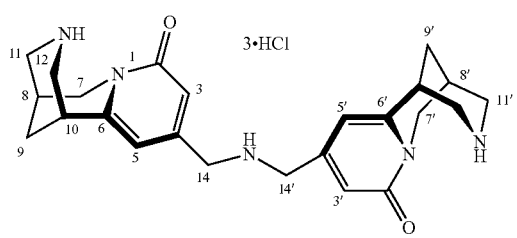

Following the general procedure A, tert-butyl(1R,5R)-10-(hydroxymethyl)-8-oxo-1,5,6,8-tetrahydro-2H-1,5-methano-pyrido [1,2-a][1,5]diazocine-3(4H)-carboxylate 153 (0.53 mmol) gave 154 (113 mg, 97%) as a colourless solid.

mp: >200° C.; colourless solid; [α]$_D^{23}$=+116 [c 0.18, DMF]; FTIR $v_{max}$/cm$^{-1}$ (neat): 2955, 2590, 1654,1584, 1547,1099, 857; $^1$H NMR (500 MHz, D$_2$O, $\delta_H$): 6.47 (s, 2H, C3-H), 6.44 (s, 2H, C5-H), 4.07 (s, 4H, C13-H), 4.00 (d, J=15.0 Hz, 2H, C7-H), 3.86 (dd, J=15.0, 6.65 Hz, 2H, C7-H), 3.40-3.20 (m, 10H, C11-H C12-H C10-H), 2.69 (s, 2H, C8-H), 1.98 (d, J=14.5 Hz, 2H, C9-H), 1.94 (d, J=14.5 Hz, 2H, C9-H); $^{13}$C NMR (125 MHz, D$_2$O, $\delta_C$): 164.6 (2×CO), 148.5 (2×C4), 144.6 (2×C6), 117.5 (2×C3), 109.2 (2×C5), 49.4, 48.2 (2×C11, 2×C12), 49.1, 48.8 (2×C7, 2×C13), 31.6 (2×C10), 24.7 (2×C8), 22.5 (2×C9); HRMS (ESI$^+$): calculated C$_{24}$H$_{32}$N$_5$O$_2$:422.2550, found [M+H]$^+$: 422.2544.

Example 48—Methylamino bis(cytisine) derivative (156)

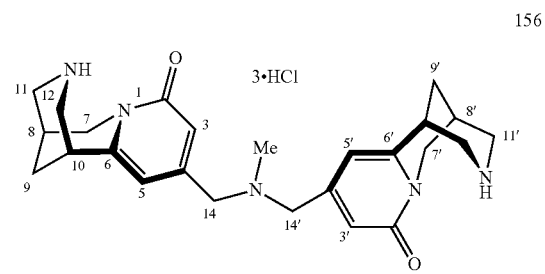

To a solution of 153 (200 mg, 0.32 mmol) in an equimolar mixture of MeOH/THF (3 mL) was added formaldehyde (0.14 mL, 6 eq., 37% aq. sol.) followed by NaCNBH$_3$ (74 mg, 3.5 eq.) and the reaction mixture was stirred for 24 h. The solution was concentrated and the crude was distributed between ammonia (20 mL, 15% aq. sol.) and DCM (20 mL), and the aqueous phase was extracted with DCM (3×20 mL). The combined organic layers were dried over MgSO$_4$, filtered and concentrated. Purification by flash column chromatography [DCM/MeOH (3% MeOH)] afforded the corresponding N-Boc protected bis(cytisine) derivative (160 mg, 82%) as a colourless solid. Subsequent deprotection and conversion into the HCl salt using the general procedure B gave 156 (89 mg, 87%) as a colourless solid.

mp: >200° C.; colourless solid; [α]$_D^{23}$=−30 [c 0.3, water]; FTIR $v_{max}$/cm$^{-1}$(neat): 3341, 1655, 1548, 1455; $^1$H NMR (500 MHz, D$_2$O, $\delta_H$): 6.67 (s, 2H, C3-H, C3'-H)), 6.65 (s, 2H, C5-H, C5'-H), 4.35 (s, 4H, C13-H, C13-H), 4.18 (d, 2H, J=15.0 Hz, C7-H, C7'-H), 4.04 (dd, 2H, J=6.0, 15.0 Hz, C7-H, C7'-H), 3.60-3.40 (m, 10H, C10-H, C10'-H, C11-H, C11'-H, C12-H, C12'-H), 2.93 (s, 3H, NMe), 2.89 (s, 2H, C8-H, C8'-H), 2.23-2.06 (m, 4H, C9-H, C9'-H); $^{13}$C NMR (125 MHz, D$_2$O, $\delta_C$): 161.9 (CO, CO'), 146.5 (C4, C4'), 140.6 (C6, C6'), 117.1 (C3, C3'), 107.9 (C5, C5'), 56.2 (C13, C13'), 47.0, 46.6 (C11, C11', C12, C12'), 45.9 (C7, C7'), 38.7 (C NMe), 29.4 (C10, C10'), 22.5 (C8, C8'), 20.2 (C9, C9'); HRMS (ESI$^+$): calculated C$_{25}$H$_{34}$N$_5$O$_2$: 436.2707, found [M+H]$^+$: 436.2692.

Example 49—(−)4-tetrazoylcytisine dihydrochloride salt (149)

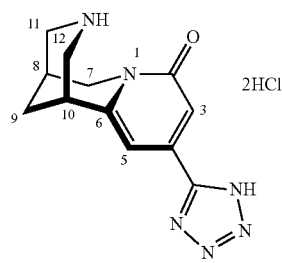

A Schlenk flask was charged with N-Boc-4-cyano-cytisine 139 (240 mg, 0.75 mmol), zinc bromide (170 mg, 0.75 mmol) and sodium azide (58 mg, 0.90 mmol) and placed under nitrogen. Water (2.5 mL, 0.3 M) and isopropanol (0.8 mL, 1.0 M) were added and the reaction mixture was heated at 60° C. for 18 h. The solvent was removed in vacuo and the residue was dissolved in DCM (20 mL) and poured over water (20 mL). The mixture was acidified with HCl (0.1 M aq. sol.) to pH≈4-5 and washed with DCM (3×20 mL). The aqueous phase was acidified to pH=1, and extracted with DCM (3×25 mL). The combined organic phases were dried over MgSO$_4$, filtered and the solvent was evaporated in vacuo. The product was converted into the HCl salt using the general procedure A yielding 149 (102 mg, 53%) as a colourless solid.

mp: >200° C., colourless solid; $[\alpha]_D{}^{23}$=−23 [c 0.13, DMF]; FTIR $v_{max}$/cm$^{-1}$ (neat): 3005, 2807, 1653, 1565; $^1$H NMR (500 MHz, D$_2$O, $\delta_H$): 6.47 (s, 1H, C3-H), 6.44 (s, 1H, C5-H), 4.07 (s, 2H, C13-H), 4.00 (d, J=15.0 Hz, 1H, C7-H), 3.86 (dd, J=15.0, 6.65 Hz, 1H, C7-H), 3.40-3.20 (m, $\delta_H$, C10-H, C11-H, C12-H), 2.69 (s, 1H, C8-H), 1.98 (d, J=14.5 Hz, 1H, C9-H), 1.94 (d, J=14.5 Hz, 1H, C9-H); $^{13}$C NMR (125 MHz, D$_2$O, $\delta_C$): 164.6 (CO), 155.9 (C4), 148.7 (C6), 137.3 (C13), 114.4 (C3), 106.7 (C5), 49.4, 48.2 (C11, C12), 48.8 (C7), 31.7 (C10), 24.8 (C8), 22.5 (C9); HRMS (ESI$^+$): calculated for C$_{12}$H$_{15}$N$_6$O: 259.1301, found [M+H-2HCl]$^+$: 259.1301.

Example 50—N-Boc-4-(dimethylamino)methyl-cytisine, and 4-(dimethylamino)methyl-(−)-cytisine dihydrochloride salt (151)

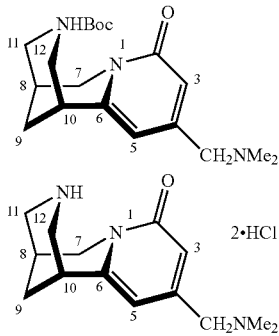

To a solution of amine 143 (320 mg, 1.0 mmol) in an equimolar mixture of THF/water (12 mL) were consecutively added formaldehyde (480 mg, 6 eq., 35% water sol.) and NaCNBH$_3$ (219 mg, 3.5 eq.). The reaction mixture was stirred at r.t for 18 h. The reaction was quenched with 10 mL of water and the aqueous phase was extracted with EtOAc (3×25 mL). The combined organic layers were dried over MgSO$_4$, filtered and concentrated in vacuo. The crude reaction mixture was purified by flash column chromatography on silica gel [DCM/MeOH (1% MeOH)] to give the product as green oil (207 mg, 60%).

Data for N-Boc4-((dimethylamino)methyl)cytisine: FTIR $v_{max}$/cm$^{-1}$ (neat): 2973, 2866, 1680, 1650, 1545; $^1$H NMR (500 MHz, CDCl$_3$, $\delta_H$): 6.35 (s, 1H, C3-H), 6.20 (s, 1H, C5-H), 4.44-4.08 (m, 3H, C11-H, C12-H, C7-H); 3.84 (dd, 1H, J=15.0, 6.0 Hz, C7-H), 3.29 (s, 1H, C13-H), 3.20 (s, 1H, C13-H), 3.13-2.91 (m, 3H, C10-H, C11-H, C12-H), 2.41 (s, 1H, C8-H), 2.27 (s, 6H, NMe$_2$), 2.03-1.90 (m, 2H, C9-H), 1.41-1.15 (m, 9H, Boc); $^{13}$C NMR (125 MHz, CDCl$_3$, $\delta_C$): 163.5 (CO), 154.4 (C4), 150.6/148.4 (C6 rotamers), 116.1 (C3), 106.5/105.5 (C5 rotamers), 80.3/79.7 (q Boc rotamers), 63.2 (C13), 51.6/50.5/49.3 (C11, C12 rotamers), 48.8 (C7), 45.5 (2C, NMe$_2$), 34.8 (C10), 28.0 (3C, Boc), 27.5 (C8), 26.2 (C9) (carbonyl carbon of the Boc group has not been found); HRMS (ESI$^+$): calculated for C$_{19}$H$_{30}$N$_3$O$_3$: 348.2282, found [M+H]$^+$: 348.2281.

Following the general procedure A, N-Boc-4-(Dimethylamino)methyl-cytisine (0.60 mmol) gave 151 (120 mg, 81%) as a colourless solid, which turned into a viscous oil after several days under air.

Data for 4-((dimethylamino)methyl)cytisine: mp: >200° C., colourless foam; $[\alpha]_D{}^{26}$=−46 [c 0.5, MeOH]; FTIR $v_{max}$/cm$^{-1}$ (neat): 2948, 1656, 1549, 1457; $^1$H NMR (500 MHz, D$_2$O, $\delta_H$): 6.70 (d, J=1.5 Hz, 1H, C3-H), 6.62 (d, J=1.5 Hz, 1H, C5-H), 4.24 (s, 2H, C13-H), 4.19 (d, J=15.0 Hz, 1H, C7-H), 4.06 (dd, J=15.0, 6.0 Hz, 1H, C7-H), 3.58-3.39 (m, $\delta_H$, C10-H, C11-H, C12-H), 2.92 (s, 6H, NMe$_2$), 2.88 (s, 1H, C8-H), 2.15 (m, 2H, C9-H); $^{13}$C NMR (MHz, D$_2$O, $\delta_C$): 164.5 (CO), 148.6 (C6), 143.2 (C4), 118.9 (C3), 109.7 (C5), 59.1 (C13), 49.3, 48.7 (C11, C12), 48.1 (C7), 42.7 (2C, NMe$_2$), 31.5 (C10), 24.7 (C8), 22.4 (C9); HRMS (ESI$^+$): calculated C$_{14}$H$_{22}$N$_3$O: 248.1757, found [M+H—HCl]$^+$: 248.1755.

Example 51—(−)4-((trimethylammonium)methyl) cytisine iodide salt (150)

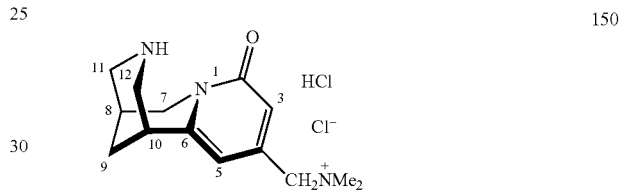

To a solution of amine 143 (220 mg, 0.63 mmol) in EtOH (6.3 mL) was added iodomethane (0.1 mL, 1.3 eq.) and the reaction was stirred for 18 h at 60° C. The solution was concentrated. Deprotection and conversion into the HCl salt using the general procedure A yielding 150 (80 mg, 42%) as a off-green amorphous solid.

Mp: 200° C.; $[\alpha]_D{}^{23}$=−65 [c 1.3, MeOH]; FTIR $v_{max}$/cm$^{-1}$ (neat): 1656, 1551, 1479; $^1$H NMR (500 MHz, D$_2$O, $\delta_H$): 6.77 (s, 1H, C3-H), 6.70 (s, 1H, C5-H), 4.42 (s, 2H, C13-H), 4.20 (d, J=15.0 Hz, 1H, C7-H), 4.09 (dd, J=15.0, 6.0 Hz, 1H, C7-H), 3.60-3.41 (m, $\delta_H$, C10-H C11-H C12-H), 3.19 (s, 9H, NMe$_3$), 2.89 (s, 1H, C8-H), 2.20 (d, J=14.0 Hz, 1H, C9-H), 2.12 (d, J=14.0 Hz, 1H, C9-H); $^{13}$C NMR (125 MHz, D$_2$O, $\delta_C$): 164.3 (CO), 148.4 (C4), 140.8 (C6), 121.9 (C3), 111.7 (C5), 67.5 (C13), 53.2 (3C, NMe$_3$), 49.4, 48.2 (C11, C12), 48.8 (C7), 31.6 (C10), 24.7 (C8), 22.5 (C9); HRMS (ESI+): calculated C15H$_{24}$N$_3$O: 262.1913, found [M+H$^+$—HCl—Cl$^-$]: 262.1924.

Example 52—(−)4-(N-acetyl)aminomethyl) cytisine (148)

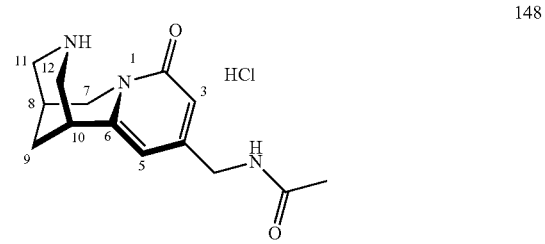

Amine 143 (310 mg, 1.0 mmol) was dissolved in isopropenyl acetate (0.33 mL, 3 eq.) and stirred at r.t. for 24 h. Then, the reaction was concentrated. The crude was purified by flash column chromatography on silica gel [DCM/MeOH (3% MeOH)] to give the product (330 mg, 92%) as a colourless solid. Deprotection and conversion using the general procedure A gave 148 (237 mg, 80%) as a colourless foam.

mp: >200° C., colourless foam; $[\alpha]_D^{23}$=−20 [c 0.5, MeOH]; FTIR $v_{max}$/cm$^1$(neat): 2197 (w), 1678, 1640, 1571, 1468; $^1$H NMR (500 MHz, D$_2$O, $\delta_H$): 6.54-6.44 (m, 2H, C3-H, C5-H), 4.29 (s, 2H, C13-H), 4.17 (d, J=15.0 Hz, 1H, C7-H), 4.04 (dd, J=15.0, 6.0 Hz, 1H, C7-H), 3.55-3.38 (m, $\delta_H$, C10-H, C11-H, C12-H), 2.83 (s, 1H, C8-H), 2.18-2.05 (m, $\delta_H$, C9-H C16-H); $^{13}$C NMR (125 MHz, D$_2$O, $\delta_C$): 174.6 (C14), 164.7 (CO), 153.3 (C4), 146.9 (C6), 112.3 (C3), 108.7 (C5), 49.5, 48.2 (C11, C12), 48.6 (C7), 41.7 (C13), 31.5 (C10), 24.8 (C8), 22.60 (C9), 21.7 (C15); HRMS (ESI+): calculated C$_{14}$H$_{20}$N$_3$O: 262.1550, found [M+H—HCl]$^+$: 262.1543.

Example 53—N-Boc 4-(4-((benzyloxy)carbonyl)piperazin-1-yl)cytisine (89)

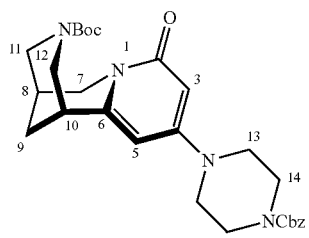

A solution of bromide 61 (180 mg, 0.5 mmol), Cu$_2$O (8 mg, 0.1 eq.) and 1-Z-piperazine (0.5 mL, 2.5 mmol) in water (1.0 mL) was stirred in a seal tube at 100° C. for 18 h. The reaction was cooled and the residue was extracted with EtOAc (3×25 mL). The combined organic layers were dried on MgSO$_4$, filtered and concentrated in vacuo. The crude reaction mixture was purified by flash column chromatography on silica gel [DCM/MeOH (2% MeOH)] to give 89 as colourless solid (220 mg, 89%), which was used in the next step without further purification.

$^1$H NMR (500 MHz, CDCl$_3$, $\delta_H$): 7.37-7.30 (m, $\delta_H$, Ar), 5.74 (d, J=2.5 Hz, 1H, C3-H), 5.64 (s, 1H, C5-H), 5.16 (s, 2H, CH$_2$-Ph), 4.39-4.06 (m, 3H, C7-H, C11-H, C12-H), 3.77 (dd, J=15.0, 6.0 Hz, 1H, C7-H), 3.60 (m, 4H, C13-H), 3.27 (m, 4H, C14-H), 3.01 (m, 2H, C11-H C12-H), 2.87 (s, 1H, C10-H), 2.35 (s, 1H, C8-H), 1.97 (d, J=12.5 Hz, 1H, C9-H), 1.89 (d, J=12.5 Hz, 1H, C9-H), 1.40-1.18 (s, 9H, Boc); $^{13}$C NMR (125 MHz, CDCl$_3$, $\delta_C$): 164.3 (CO), 156.4 (CO), 155.1 (CO), 154.6 (C4), 148.3 (C6), 136.4 (Ar), 128.5 (2C, Ar), 128.1 (Ar), 127.9 (2C, Ar), 96.4 (C3), 95.0 (C5), 80.1 (q Boc), 67.7 (CH$_2$-Ph), 50.6, 50.5 (C11, C12), 47.9 (C7), 46.1 (2C, C13), 43.1 (2C, C14), 35.4 (C10), 28.1 (3C, Boc), 27.7 (C8), 26.5 (C9); HRMS (ESI$^+$): calculated for C$_{28}$H$_{37}$N$_4$O$_5$: 509.2758, found [M+H]$^+$: 509.2733.

Example 54—N-Boc 4-(piperazin-1-yl) cytisine

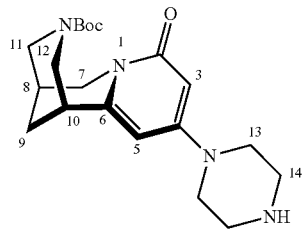

A solution of 89 (160 mg, 0.32 mmol) in methanol (5 mL) was placed under nitrogen and palladium on activated charcoal 10 wt % (5 mg, 0.1 eq.) was added. The vessel was placed under vacuum and backfilled with hydrogen for three times and stirred for 18 h. The reaction mixture was filtered through Celite® and the solvent was concentrated, giving the piperazinyl derivative (85 mg, 71%) as a colourless solid, which was used in the next step without further purification.

$^1$H NMR (500 MHz, CDCl$_3$, SH): 5.85 (s, 1H, C3-H), 5.72 (s, 1H, C5-H), 5.49 (br, 1H, NH), 4.33-4.01 (m, 3H, C7-H, C11-H, C12-H), 3.74 (dd, J=15.0, 6.0 Hz, 1H, C7-H), 3.55 (s, 4H, C13-H), 3.19 (s, 4H, C14-H), 3.07-2.94 (m, 2H, C11-H, C12-H), 2.92 (s, 1H, C10-H), 2.36 (s, 1H, C8-H), 1.96 (d, J=13.5 Hz, 1H, C9-H), 1.89 (d, J=13.5 Hz, 1H, C9-H); 1.38-1.19 (s, 9H, Boc); $^{13}$C NMR (125 MHz, CDCl$_3$, $\delta_C$): 164.6 (CO), 156.4 (CO), 154.5 (C4), 148.8 (C6), 96.9 (C3), 95.0 (C5), 80.0 (q Boc), 50.6, 50.5 (C11, C12), 48.2 (C7), 44.7 (2C, C13), 43.6 (2C, C14), 35.2 (C10), 28.1 (3C, Boc), 27.5 (C8), 26.4 (C9); HRMS (ESI$^+$): calculated C$_{20}$H$_{31}$N$_4$O$_3$: 375.2391, found [M+H]$^+$: 375.2383.

Example 55—(+)4-(N-piperazinyl)cytisine trihydrochloride salt (90)

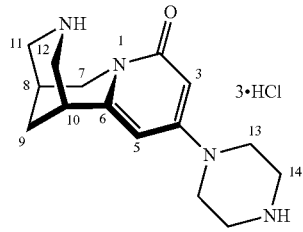

A solution of N-Boc 4-N—(N'—Cbz)-piperazine-cytisine (323 mg, 0.64 mmol) in MeOH (6.4 mL) was placed under nitrogen and Pd/C (10 wt %) (6.5 mg, 0.1 eq) was added. The vessel was placed under vacuum and backfilled with hydrogen for three times and stirred for 24 h. The mixture was filtered through Celite® and concentrated in vacuo. Deprotection and conversion into its HCl salt using the general procedure A gave 90 (237 mg, 96%) as a colourless solid.

mp: >200° C., colourless powder; $[\alpha]_D^{25}$=+52 [c 1.0, MeOH]; FTIR $v_{max}$/cm$^{-1}$ (neat): 3374, 2924, 2712, 2585, 2451, 1638, 1538; $^1$H NMR (400 MHz, D$_2$O, $\delta_H$): 6.55 (s, 1H, C3-H), 4.10 (d, J=15.0 Hz, 1H, C7-H$_a$), 3.98 (dd, J=6.5, 15.0 Hz, 1H, C7-H$_b$), 3.69-3.66 (m, 4H, C14-H), 3.47-3.26 (m, 9H, C10-H, C11-H, C12-H, C13-H), 2.70 (s, 1H, C8-H), 2.07-1.96 (m, 2H, C9-H), C5-H not detected due to deuterium exchange; $^{13}$C NMR (100 MHz, D$_2$O, $\delta_C$): 162.1 (CO), 157.2 (C4), 148.1 (C6), 102.4 (C3), 92.2-91.7 (m, C5), 49.2 (C11 or C12), 48.8 (C7), 48.1 (C11 or C12), 42.7 (2C, C13), 42.5 (2C, C14), 31.7 (C10), 24.5 (C8), 22.5 (C9); HRMS (ESI$^+$): calculated for C$_{15}$H$_{23}$N$_4$O: 275.1866, found [M+H-3HCl]$^+$: 275.1868.

Example 56a—N-Boc 3-(trifluoromethyl)-4-bromocytisine 161

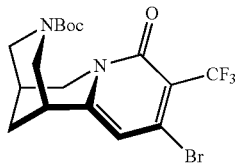

161

A solution of N-Boc 4-bromo-cytisine 61 (370 mg, 1.0 mmol) in a mixture of DMSO (3.8 mL) H$_2$O (1.6 mL) was cooled to 0° C. and sodium trifluoromethylsulfonate (470 mg, 3.0 mmol) was added. Tert-butyl hydroperoxide (0.7 mL, 70% aq.sol.) was added dropwise during 5 min. and the solution was allowed to warm to r.t. and stirred for 24 h. The solvent was removed in vacuo. The crude was distributed between ammonia (15 mL, 15% aq. sol.) and DCM (15 mL), and the aqueous phase was extracted with DCM (3×25 mL). The combined organic phases were dried over MgSO$_4$, filtered and concentrated. The crude was purified by flash column chromatography on silica gel [n-Hexane/EtOAc (1:1)] to give 161 (130 mg, 30%) as colourless solid, together with 3% of N-Boc-5-CF$_{3-4}$-Bromo-cytisine. [1H NMR: 98% (C3-substituted), 2% (C5-substituted; 87% conversion)].

FTIR $v_{max}$/cm$^{-1}$ (neat): 2972, 2923, 2865, 1677, 1645, 1543; $^1$H NMR (500 MHz, CDCl$_3$, $\delta_H$): 6.41 (s, 1H, C5-H), 4.45-4.10 (m, 3H, C7-H, C11-H, C12-H), 3.88-3.76 (dd, J=6.5, 15.5 Hz, 1H, C7-H), 3.23-2.91 (m, 3H, C11-H, C12-H, C10-H), 2.48 (s, 1H, C8-H), 1.99 (s, 2H, C9-H), 1.44-1.18 (m, 9H, Boc); $^{13}$C NMR (125 MHz, CDCl$_3$, $\delta_C$): 158.7 (CO), 154.5/154.0 (CO, rotamers), 152.2/151.7 (C6), 135.0/134.7 (C4), 122.6 (q, J=276 Hz, CF$_3$), 116.2 (q, J=30 Hz, C3), 121.3/110.5 (C5, rotamers), 80.9/80.3 (q Boc, rotamers), 51.2/50.4/49.8/49.1 (C11, C12, rotamers), 49.4 (C7, rotamers), 34.7 (C10), 28.0 (3C, Boc), 27.2 (C8), 25.5 (C9); HRMS (ESI+): calculated for C$_{17}$H$_{21}$BrF$_3$N$_2$O$_3$: 437.0682, found [M+H]$^+$: 437.0679.

Example 56b—(−)3-(Trifluoromethyl)-4-bromocytisine hydrochloride salt (162)

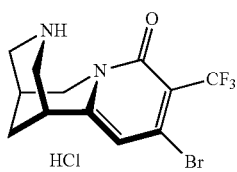

162

Following the general procedure A, bromide 161 (0.25 mmol) gave 162 (0.45 mg, 48%).

mp: >200° C., colourless powder; [α]$_D^{23}$=−19 [c 0.20, MeOH]; FTIR $v_{max}$/cm$^{-1}$ (neat): 1651, 1543, 1130, 1076; $^1$H NMR (400 MHz, D$_2$O, $\delta_H$): 6.83 (s, 1H, C5-H), 4.04 (d, J=15.5 Hz, 1H, C7-H), 3.89 (dd, J=6.5, 15.5 Hz, 1H, C7-H), 3.46-3.28 (m, $\delta_H$, C10-H, C11-H, C12-H), 2.76 (s, 1H, C8-H), 2.06 (d, J=13.5 Hz, 1H, C9-H), 2.00 (d, J=13.5 Hz, 1H, C9-H); $^{13}$C NMR (100 MHz, D$_2$O, $\delta_C$): 160.7 (CO), 150.3 (C6), 136.5 (C4), 122.4 (q, J=275 Hz, CF$_3$), 116.2 (q, J=30 Hz, C3-H), 114.3 (C5-H), 48.9, 48.0 (C11, C12), 48.8 (C7), 31.4 (C10), 24.5 (C8), 22.1 (C9); HRMS (ESI$^+$): calculated for C$_{12}$H$_{13}$BrF$_3$N$_2$O: 337.0158, found [M+H]$^+$: 337.0162.

Example 57a—N-Boc 3-bromo-4-iodocytisine (159)

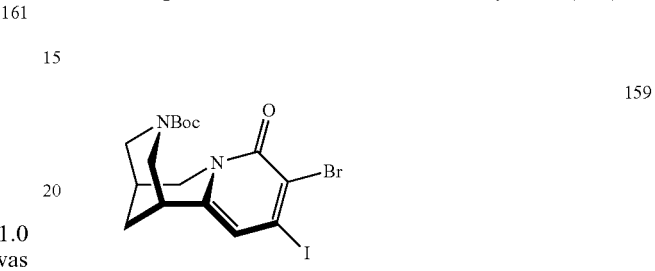

159

N-Boc-4-iodo-cytisine 65 (120 mg, 0.286 mmol) was dissolved in THF (6 mL, 0.05 M) and N-bromosuccinimide (51 mg, 0.286 mmol) was added. The reaction mixture was stirred at r.t. for 24 h. The reaction was diluted with water (15 mL), and the aqueous phase was extracted with EtOAc (3×25 mL). The combined organic phases were dried over MgSO$_4$, filtered and concentrated. The crude was purified by flash column chromatography on silica gel [n-Hexane/EtOAc (1:1)] to give 159 (91 mg, 65%), contaminated with N-Boc-5-bromo-4-iodo-cytisine (in a ratio 22:3).

FTIR $v_{max}$/cm$^{-1}$ (neat): 2925, 2865, 1669, 1634, 1569; $^1$H NMR (500 MHz, CDCl$_3$, $\delta_H$): 6.58 (s, 1H, C5-H), 4.43-4.06 (m, 3H, C7-H, C11-H, C12-H), 3.78 (dd, J=6.5, 15.5 Hz, 1H, C7-H), 3.16-2.86 (m, 3H, C10-H, C11-H, C12-H), 2.42 (s, 1H, C8-H), 1.96 (m, 2H, C9-H), 1.40-1.15 (m, 9H, Boc); $^{13}$C NMR (125 MHz, CDCl$_3$, $\delta_C$): 157.7 (CO), 156.5 (CO), 154.6/154.1 (C6, rotamers), 147.7/147.2 (C4, rotamers), 121.4 (C3), 115.5/114.9 (C5, rotamers), 80.6/80.1 (q Boc, rotamers), 51.8/51.5/50.0/49.4 (C11, C12, rotamers), 50.4 (C7, rotamers), 34.3 (C10), 28.1 (3C, Boc), 27.4 (C8), 25.9 (C9), HRMS (ESI$^+$): calculated for C$_{16}$H$_{21}$BrIN$_2$O$_3$: 494.9774, found [M+H]$^+$: 494.9761.

Example 57b—(+)3-Bromo-4-iodocytisine hydrochloride salt (160)

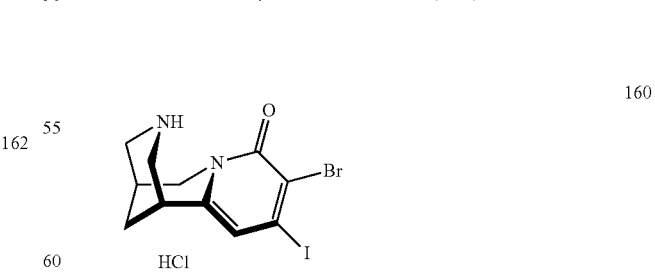

160

Following the general procedure A, iodide 159 (0.16 mmol) gave 160 (57 mg, 81%); contaminated with 5-bromo-4-iodo-cytisine (ratio 22:3).

[α]$_D^{23}$=+7 [c 0.3, water]; FTIR $v_{max}$/cm$^{-1}$ (neat): 2985, 1606, 1566, 1096; $^1$H NMR (500 MHz, DMSO, $\delta_H$): 6.83 (s, 1H, C5-H), 3.92 (d, J=15.5 Hz, 1H, C7-H), 3.79 (dd, J=6.5, 15.5 Hz, 1H, C7-H), 3.33-3.12 (m, $\delta_H$, C11-H, C12-H, C10-H), 2.62 (s, 1H, C8-H), 1.99 (d, J=13.5 Hz, 1H, C9-H), 1.87 (d, J=13.5 Hz, 1H, C9-H); $^{13}$C NMR (125 MHz, DMSO, $\delta_C$): 157.7 (CO), 147.7 (C6), 121.0 (C4), 116.4 (C3), 115.6 (C5), 49.8 (C7), 48.8, 48.0 (C11, C12), 30.9 (C10), 14.9 (C8), 22.9 (C9); HRMS (ESI$^+$): calculated for $C_{11}H_{13}BrIN_2O$: 394.9250, found [M+H—HCl]$^+$: 394.9249.

Example 58a—N-Boc 3-Bromo-4-methylaminocytisine (157)

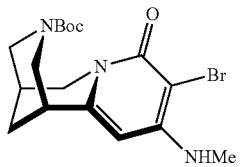

To a solution of N-methyl amine 83 (96 mg, 0.30 mmol) in THF (6.0 mL) was added N-bromosuccinimide (54 mg, 0.30 mmol) and the reaction was stirred at r.t. for 24 h. The reaction was diluted with water (15 mL) and the aqueous phase was extracted with EtOAc (3×25 mL). The combined organic phases were dried over MgSO$_4$, filtered and concentrated. The crude was purified by flash column chromatography on silica gel [DCM/MeOH (2% MeOH)] to give 157 (N-Boc-3-bromo-4-methylamino-cytisine) (84 mg, 70%), and N-Boc-5-bromo-4-methylamino (27 mg, 22%), which was used in the next step without further purification.

Data for 157: FTIR $v_{max}$/cm$^{-1}$ (neat): 3290, 2946, 2761, 2623, 1633, 1493, 1206, 1100, 1025, 567, 521; 1H NMR (500 MHz, CDCl$_3$, $\delta_H$): 5.68 (s, 1H, C5-H), 4.84 (s, 1H, NH), 4.36-4.05 (m, 3H, C11-H, C12-H, C7-H), 3.79 (dd, J=6.5, 15.5 Hz, 1H, C7-H), 3.13-2.85 (m, 6H, C11-H, C12-H, C10-H, NHMe), 2.33 (s, 1H, C8-H), 1.91 (m, 2H, C9-H), 1.36-1.13 (m, 9H, Boc); $^{13}$C NMR (125 MHz, CDCl$_3$, $\delta_C$): 159.2 (CO), 154.7, 154.2 (C6, rotamers), 152.4 (CO), 148.0, 147.7 (C4, rotamers), 93.0, 92.5 (C5-H), 90.4 (C3), 80.3, 79.7 (q Boc, rotamers), 51.6, 50.6, 50.2, 49.3 (C11, C12), 49.1 (C7), 35.0 (C10), 29.8 (C8), 28.0, 27.7 (Boc, rotamers), 26.2 (C9).

Example 58b—(+)3-Bromo-4-N-methylaminocytisine hydrochloride salt (158)

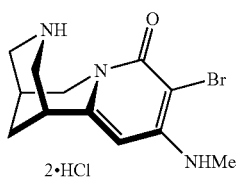

Following the general procedure A, N-Methyl amine 157 (0.21 mmol) gave 158 (45 mg, 73%) as a colourless solid, contaminated with 9% of 5-Bromo-4-methylamino-cytisine. $[\alpha]_D^{23}$=+38 [c 0.5, MeOH]; FTIR $v_{max}$/cm$^{-1}$ (neat): 3291, 2949, 2761, 2624, 1634, 1583; $^1$H NMR (500 MHz, D$_2$O, $\delta_H$): 6.14 (s, 1H, C5-H), 4.13 (d, J=15.5 Hz, 1H, C7-H), 3.88 (dd, J=6.5, 15.5 Hz, 1H, C7-H), 3.52-3.32 (m, $\delta_H$, C11-H, C12-H, C10-H), 2.84 (s, 3H, NHMe), 2.70 (s, 1H, C8-H), 2.04 (m, 2H, C9-H); $^{13}$C NMR (125 MHz, D$_2$O, $\delta_C$): 160.5 (CO), 154.3 (C6), 145.6 (C4), 97.0 (C3), 89.6 (C5), 49.3, 48.5 (C11, C12), 48.9 (C7), 31.6 (C10), 28.9 (NHMe), 24.9 (C8), 22.9 (C9); HRMS (ESI$^+$): calculated for $C_{12}H_{17}BrN_3O$: 298.0549, found [M+H]$^+$: 298.0549.

Example 59—Iridium-catalyzed C—H borylation of (−)-cytisine

Synthesis of 4-Bpincytisine

A Schlenk tube was charged with (−)-cytisine (190 mg, 1.0 mmol), [Ir(COD)(OMe)]$_2$ (6.6 mg, 0.01 eq), 4,4'-2,2'-di-tert-butylbispyridine (5.4 mg, 0.02 eq) and bis(pinacolato)diboron (380 mg, 1.50 eq). After purging with nitrogen, THF (1.4 mL) was added and the reaction mixture was heated at reflux for 24 h. After this time, the volatile materials were removed under reduced pressure and 4-Bpincytisine was partially characterized without further purification and obtained as a brown foam.

1H NMR (500 MHz, CDCl$_3$): δ=6.88 (d, 1H, J=1.0 Hz), 6.27 (s, 1H), 4.11 (d, 1H, J=15.5 Hz), 3.86 (dd, 1H, J=6.5, 15.5 Hz), 3.15-2.78 (m, $\delta_H$), 3.21 (s, 1H), 1.94-1.91 (m, 2H), 1.23 (s, 12H).

13C NMR (125 MHz, CDCl3): δ=163.1, 149.2, 124.1, 108.8, 84.4, 82.7, 53.3, 52.3, 49.6, 35.1, 27.5, 25.5, 14.5.

To confirm the identity of 4-Bpincytisine, that compound was further converted to 4-bromocytisine by treatment with an aqueous solution of CuBr$_2$ in MeOH. The spectroscopic properties of 4-bromocytisine were consistent with the data available in literature.

Example 60—Iridium-Catalyzed C—H Borylation of (−)—Cytisine

Synthesis of 4-Bpincytisine

The process of Example 59 was carried out, using the same apparatus and solvents, catalysts and ligands in the same molar amounts as outlined above, except that Me4phen was used as a ligand and the borylating agent B$_2$Pin$_2$ was present at 3.00 eq. The process resulted in 100% conversion of cytisine to 4-Bpincytisine.

Example 61—Iridium-Catalyzed C—H Borylation of (−)—Cytisine

Synthesis of 4-Bpincytisine

The process of Example 59 was carried out, using the same apparatus and solvents, catalysts and ligands in the same molar amounts as outlined above, except that neocuproine was used as a ligand. The process resulted in 100% conversion of cytisine to 4-Bpincytisine.

Example 62—Iridium-Catalyzed C—H Borylation of N-Boc Cytisine (56)

Synthesis of N-Boc 4-Bpincytisine (58)

A Schienk tube was charged with N-Boc cytisine (56) (290 mg, 1.0 mmol), [Ir(COD)(OMe)]$_2$ (6.6 mg, 0.01 eq), 4,4'-2,2'-di-tert-butylbispyridine (5.4 mg, 0.02 eq) and bis (pinacolato)diboron (178 mg, 0.70 eq). After purging with nitrogen, THE (1.4 mL) was added and the reaction mixture was heated at reflux for 18 h. After this time, 1H NMR showed essentially 100% conversion, the volatile materials were removed under reduced pressure.

The crude product N-Boc 4-Bpincytisine (58) was shown to be essentially pure by 1H NMR and although further purification is possible, this is unnecessary prior to using N-Boc 4-Bpincytisine (58) as a reactant.

Further purification of crude N-Boc 4-Bpincytisine (58) was achieved using chromatography (DCM-MeOH, 95:5) to give pure N-Boc 4-Bpincytisine (58) (180 mg, 43%) as a pale yellow foam;

Rf=0.23 (DCM-MeOH, 95:5).

IR (neat): 3433, 2977, 1688, 1657, 1563, 1423 cm−1.

1H NMR (400 MHz, CDCl$_3$): δ=6.85 (s, 1H), 6.31 (s, 1H), 4.34-4.10 (m, 3H), 3.80 (dd, 1H, J=6.5, 15.5 Hz), 3.07-2.91 (m, 3H), 2.41 (s, 1H), 1.95-1.88 (m, 2H), 1.41-1.09 (m, 21H).

13C NMR (100 MHz, CDCl$_3$): δ=162.9, 154.6/154.3 (rotamers), 147.9/147.5 (rotamers), 124.4, 109.3/108.8 (rotamers), 84.4, 82.6/80.3, 79.7/75.0 (2 C, rotamers), 51.7/50.6/50.3/49.2 (2 C, rotamers), 48.9, 34.7, 28.0 (4 C), 27.5, 26.1, 24.8/24.6 (3 C, rotamers); C-Bpin was not observed.

11B NMR (96.4 MHz, CDCl$_3$): δ=28.94 (br s).

HRMS-ESI: m/z [M+H]+ calcd for C22H33BN2NaO5: 439.2379; found: 439.2373.

Example 63—Iridium-Catalyzed C—H Borylation of N-Boc Cytisine (56)

Synthesis of N-Boc 4-Bpincytisine (58)

The process of Example 62 was carried out, using the same apparatus and solvents, catalysts and ligands in the same molar amounts as outlined above, except that N-methyl cytisine was used as a starting material of Formula IIa. The process resulted in 98% conversion of cytisine to 4-Bpincytisine.

Example 64—Iridium-catalyzed C—H borylation of N-Boc cytisine (56)

Synthesis of N-Boc 4-Bpincytisine (58)

The process of Example 62 was carried out, using the same apparatus and solvents, catalysts and ligands in the same molar amounts as outlined above, except that N-Cbz cytisine was used as a starting material of Formula IIa. The process resulted in 88% conversion of cytisine to 4-Bpincytisine.

Example 65—N-Boc 4-p-tolylcytisine (72)

N-Boc 4-Bpincytisine 58 was made following the general procedure discussed above on a 0.5 mmol scale. To crude N-Boc 4-Bpincytisine was added potassium carbonate (124 mg, 0.90 mmol), tetrakis (triphenylphosphine) palladium(0) (28 mg, 0.05 eq) and 4-bromotoluene (0.25 mL, 1.0 mmol) and a mixture of DME/water (5:1) (5 mL, 0.1 M) was added. The mixture was heated at 80° C. for 24 h, then cooled to room temperature and diluted with water (15 mL). The aqueous phase was extracted with DCM (3×15 mL) and the combined organic phases were dried over MgSO$_4$, filtered and concentrated. Purification by flash column chromatography [DCM/MeOH (1.5% MeOH)] afforded N-Boc 4-(p tolyl)cytisine (104 mg, 55%) as a colourless solid.

Example 66—N-Boc 4-methylcytisine (109)

N-Boc 4-Bpincytisine 58 was made following the general procedure discussed above for the borylation of cytisine on a 0.5 mmol scale.

Using a modification of a related procedure, to crude N-Boc 4-Bpincytisine 58 were added Pd$_2$dba$_3$ (11 mg, 0.025 eq), tri(p tolyl)phosphine (7.6 mg, 0.05 eq), potassium carbonate (138 mg, 2.0 eq), iodomethane (0.03 mL, 1.0 eq) and the vessel was placed under vacuum and backfilled with nitrogen three times. A mixture of DMF/water (9:1.5 mL) was added and the reaction mixture was stirred at 60° C. for 18 h. The mixture was cooled to r.t. and the solvent removed in vacuo. The residue was partitioned between EtOAc (15 mL) and water (15 mL) and the aqueous phase was extracted with EtOAc (3×15 mL). The combined organic phases were dried over MgSO$_4$, filtered, concentrated and purified by flash column chromatography on silica gel [DCM/MeOH (3% MeOH)] to give N-Boc 4-methylcytisine (98 mg, 64%) as a pale yellow solid.

Example 67a—N-Boc (3-bromo-4-hydroxy)cytisine

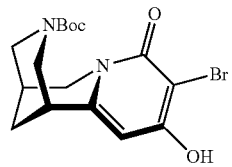

A solution of N-Boc 4-aminocytisine (512 mg, 1.67 mmol) in THF (32 mL) was cooled to 0° C., N-bromosuccinimide (312 mg, 1.76 mmol) was added, and the reaction mixture was stirred at 0° C. for 18 hours. Water (25 mL) was added and the aqueous phase was extracted with EtOAc (3×25 mL). The combined organic phases were dried over MgSO$_4$, filtered and concentrated. Purification of the crude reaction mixture by flash column chromatography [EtOAc/MeOH (1% MeOH)] afforded N-Boc (3-bromo-4-hydroxy)cytisine (350 mg, 55%) as a colourless solid.

R$_f$: 0.37 [DCM/MeOH (5% MeOH)]; FTIR $v_{max}$/cm$^{-1}$ (neat): 2864, 1698, 1581, 1408,1245,1129; $^1$H NMR (500 MHz, DMSO, $δ_H$): 11.00 (s, 1H), 5.94 (s, 1H), 4.18-3.81 (m, 3H), 3.58 (dd, J=15.0, 6.5 Hz, 1H), 3.14-2.85 (m, 3H), 2.30 (s, 1H), 1.85 (s, 2H), 1.29-1.02 (m, 9H); $^{13}$C NMR (500 MHz, DMSO, $δ_C$): 162.6, 160.4, 154.1, 149.0, 98.0, 93.2, 79.1, 51.7, 50.5, 49.6, 34.3, 28.0, 27.4, 25.7; HRMS (ESI$^+$): calculated for C$_{16}$H$_{22}^{79}$BrN$_2$O$_4$: 385.0757, found [M+H]$^+$: 385.0764.

Example 67b—(−)-(3-bromo-4-hydroxy)cytisine hydrochloride salt (BS70)

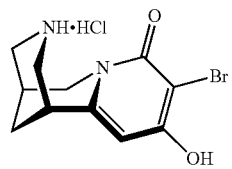

Following the general procedure A, N-Boc (3-bromo-4-hydroxy)cytisine (0.83 mmol) gave BS70 (236 mg, quantitative) as a colourless solid.

mp: >200° C.; $[\alpha]_D^{24}$=−0.12 [c 1.0, water]; FTIR $v_{max}$/cm$^{-1}$ (neat): 2573, 1646, 1550, 1408, 1310, 1097, 854; $^1$H NMR (500 MHz, D$_2$O, $\delta_H$): 6.34 (s, 1H), 4.26 (d, J=15.5 Hz, 1H), 4.00 (dd, J=15.5, 7.0 Hz, 1H), 3.60 (d, J=13.5 Hz, 1H), 3.50-3.40 (m, 4H), 2.82 (s, 1H), 2.13 (m, 2H); $^{13}$C NMR (500 MHz, D$_2$O, $\delta_C$): 163.3, 162.3, 146.4, 101.5, 94.8, 49.3, 49.2, 48.3, 31.4, 24.8, 22.7; HRMS (ESI$^+$): calculated for C$_{11}$H$_{14}^{79}$BrN$_2$O$_2$: 285.0160, found [M+H]$^+$: 285.0230.

Example 68a—N-Boc (3-bromo-4-amino)cytisine

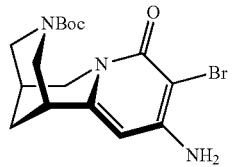

A solution of 4-aminocytisine (250 mg, 0.82 mmol) in THF (16 mL) was cooled to 0° C., N-bromosuccinimide (153 mg, 0.86 mmol) was added, and the reaction mixture was stirred at 0° C. for 18 hours. Water (25 mL) was added and the aqueous phase was extracted with EtOAc (3×25 mL). The combined organic phases were dried over MgSO$_4$, filtered and concentrated. Purification of the crude reaction mixture by flash column chromatography [EtOAc] afforded N-Boc (3-bromo-4-amino)cytisine (95 mg, 30%) as a colourless solid.

R$_f$: 0.43 [DCM/MeOH (6% MeOH)]; mp: α200° C. (toluene); FTIR $v_{max}$/cm$^{-1}$ (neat): 3441, 3178, 2917, 1682, 1633, 1591, 1427, 1124, 820, 751; $^1$H NMR (500 MHz, CDCl$_3$, $\delta_H$): 5.67 (s, 1H), 4.59 (s, 2H), 4.43-4.00 (m, 3H), 3.82 (dd, J=15.5, 6.5 Hz, 1H), 3.13-2.87 (m, 3H), 2.36 (s, 1H), 1.95 (d, J=12.5 Hz, 1H), 1.91 (d, J=12.5 Hz, 1H), 1.39-1.18 (m, 9H); $^{13}$C NMR (500 MHz, CDCl$_3$, $\delta_C$): 159.8, 154.4, 151.5, 146.9, 96.1, 91.4, 80.3, 51.5, 50.4, 49.3, 34.7, 28.0, 27.4, 26.3; HRMS (ESI$^+$): calculated for C$_{16}$H$_{22}^{81}$BrN$_3$NaO$_3$: 408.0737, found [M+Na]$^+$: 408.0713.

Example 68b—(+)-(3-bromo-4-amino)cytisine hydrochloride salt (BS71)

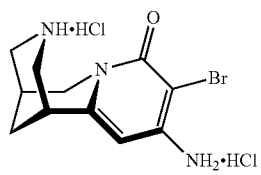

Following the general procedure A, N-Boc (3-bromo-4-amino)cytisine gave BS71 (62 mg, 64%) as a colourless solid.

mp: >200° C. (toluene); $[\alpha]_D^{24}$=+0.08 [c 1.0, water]; FTIR $v_{max}$/cm$^{-1}$ (neat): 3313, 3132, 2934, 2756, 1641, 1532, 1454, 1163; $^1$H NMR (500 MHz, MeOD, $\delta_H$): 6.15 (s, 1H), 4.37 (d, J=15.5 Hz, 1H), 3.92 (dd, J=15.5, 6.5 Hz, 1H), 3.54 (d, J=13.0 Hz, 1H), 3.49-3.36 (m, 3H), 3.31 (s, 1H), 2.70 (s, 1H), 2.15 (d, J=13.5 Hz, 1H), 2.07 (d, J=13.5 Hz, 1H); $^{13}$C NMR (500 MHz, MeOD, $\delta_C$): 159.9, 154.7, 144.9, 100.2, 89.3, 49.2, 48.9, 48.3, 31.6, 25.4, 23.2; HRMS (ESI$^+$): calculated for C$_{11}$H$_{15}^{79}$BrN$_3$O: 284.0393, found [M+H]$^+$: 284.0390.

Example 69a—N-Boc (3-bromo-4-ethyl)cytisine

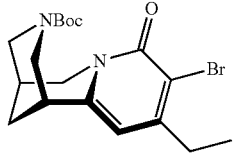

A solution of N-Boc 4-ethyl-cytisine (341 mg, 1.07 mmol) in THF (20 mL) was cooled to 0° C., N-bromosuccinimide (190 mg, 1.07 mmol) was added, and the reaction mixture was stirred at 0° C. for 18 hours. Water (25 mL) was added and the aqueous phase was extracted with EtOAc (3×25 mL). The combined organic phases were dried over MgSO$_4$, filtered and concentrated. Purification of the crude reaction mixture by flask column chromatography [DCM/MeOH (2% MeOH)] afforded N-Boc (3-bromo-4-ethyl) cytisine (296 mg, 70%) as a colourless solid.

R$_f$: 0.22 [DCM/MeOH (2% MeOH)]; $^1$H NMR (500 MHz, CDCl$_3$, $\delta_H$): 5.99 (s, 1H), 4.45-4.02 (m, 3H), 3.86 (dd, J=15.5, 6.5 Hz, 1H), 3.16-2.86 (m, 3H), 2.66 (m, 2H), 2.40 (s, 1H), 2.00-1.88 (m, 2H), 1.44-1.03 (m, 12H); $^{13}$C NMR (500 MHz, CDCl$_3$, $\delta_C$): 159.5, 154.5, 146.8, 112.9, 106.3, 80.3, 51.5, 50.4, 50.0, 29.8, 29.6, 28.0, 27.4, 26.2, 12.7, (C9 has not been found); HRMS (ESI$^+$): calculated for C$_{18}$H$_{28}^{79}$BrN$_2$O$_3$: 397.1121, found [M+H]$^+$: 397.1121.

Example 69b—(−)-(3-bromo-4-ethyl)cytisine (BS74)

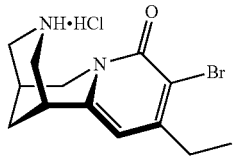

Following the general procedure A, N-Boc (3-bromo-4-ethyl)cytisine (296 mg, 0.75 mmol) gave BS74 (80 mg, 37%) as a colourless solid.

mp: ≥200° C.; $[\alpha]_D^{24}$=−0.21 [c 1.0, water]; FTIR $v_{max}$/cm$^{-1}$ (neat): 2935, 2544, 1635, 1572, 1450, 1101, 705; $^1$H NMR (500 MHz, MeOD, $\delta_H$): 6.50 (s, 1H), 4.45 (d, J=15.5 Hz, 1H), 4.02 (dd, J=15.5, 6.5 Hz, 1H), 3.63 (d, J=13.5 Hz, 1H), 3.54-3.42 (m, 4H), 2.81 (s, 1H), 2.72 (m, 2H), 2.22 (d, J=13.5 Hz, 1H), 2.12 (d, J=13.5 Hz, 1H), 1.25 (t, J 10=7.0 Hz, 3H); $^{13}$C NMR (500 MHz, MeOD, $\delta_C$): 159.9, 156.0, 144.9, 112.9, 108.8, 49.6, 49.3, 48.4, 31.6, 29.4, 25.4, 22.9, 11.5; HRMS (ESI$^+$): calculated for C$_{13}$H$_{18}^{79}$BrN$_2$O: 297.0597, found [M+H]$^+$: 297.0591.

Example 70 Binding to Nicotinic Receptor Subtypes

The binding of a group of compounds mentioned above were tested for their affinity at different nAChR subtypes, specifically the α4β2, the α3β4 and α7. The protocol for these tests is set out below, and the results are provided at Table 1 below.

Binding to Heterologously Expressed_α4β2 and α3β4 Human Subtypes

HEK 293 cells were grown in Dulbecco's modified Eagle medium supplemented with 10% fetal bovine serum, 1% L-Glutamine, 100 units/ml penicillin G, and 100 µg/streptomycin in a humidified atmosphere containing 10% $CO_2$. The cDNAs encoding α3 and β4 or α4 and 02 (were transfected into the HEK 293 cells at 30% confluency). The cell transfections were carried out in 100 mm Petri dishes using 30 µL of JetPEI™ (Polypus, France) (1 mg/ml, pH 7.2) and 3 µg of each cDNA. After 24 h transfection, the cells were collected, washed with PBS by centrifugation, and used for binding analysis.

[$^3$H]-epibatidine saturation binding experiments to HEK transfected α3β4 or α4β2 receptors were performed by means of overnight incubation at 4° C. at concentrations ranging from 0.005 to 1 nM in a buffer containing 50 mM Tris-HCl, pH 7, 150 mM NaCl, 5 mM KCl, 1 mM $MgCl_2$, 2.5 mM C≡$Cl_2$) and 2 mg/ml BSA, in the presence (aspecific binding) or absence (total binding) of 100 nM cold epibatidine. Specific ligand binding was defined as total binding minus the binding in the presence of 100 nM cold epibatidine.

The inhibition of [$^3$H]-epibatidine binding induced by the compounds or nicotinic ligands was measured by incubating increasing concentrations (10 pM-10 mM) of the test compounds for 30 min at room temperature (r. t.), followed by overnight incubation at 4° C. with a final concentration of 0.25 nM [$^3$H]-epibatidine (in the case of the α4β2* subtype) or 0.5 nM (in the case of the α3β4 subtype). After incubation, the membranes of HEK cells transfected with α4β2* or α3β4 subtypes were washed by filtration on GFC filters with ice-cold PBS. The GFC filters were pre-soaked in polyethylenimine and filtered through an harvester apparatus. [$^3$H]-epibatidine binding was determined by means of liquid scintillation counting in a beta counter.

Binding to Heterologously Expressed_α7 Subtype

The human α7 cDNA was transfected into SH-SY5Y human neuroblastoma cells. The cell transfections were carried out in 100 mm Petri dishes using 30 µL of JetPEI™ (Polypus, France) (1 mg/ml, pH 7.2) and 6 µg of α7 cDNA. After 24 h transfection, the cells were collected, washed with PBS by centrifugation, and used for binding analysis.

The [$^{125}$I]-α-Bungarotoxin (purchased from Perkin Elmer, Boston MA) saturation binding was performed by incubating SH-SY5Y membranes overnight with 0.1-10 nM concentrations of [$^{125}$I]-α-bungarotoxin at r. t. Non-specific binding was determined in parallel by means of incubation in the presence of 1 µM unlabelled α-bungarotoxin. After incubation, the samples were filtered as described above and the bound radioactivity directly counted in a γ counter. The inhibition of [$^{125}$I]-α-Bungarotoxin binding by the test compounds was measured by preincubating SH-SY5Y membranes with increasing concentrations (10 M-1 mM) of the drug to be tested for 30 min at r. t., followed by overnight incubation with a final concentration of 2-3 nM [$^{125}$I]-α-bungarotoxin at room temperature.

After overnight incubation, the membranes of SH-SY5Y cells transfected with α7 were washed by filtration on GFC filters with ice-cold PBS. The GFC filters were pre-soaked in polyethylenimine and filtered through an harvester apparatus. and [$^{125}$I]-α-Bungarotoxin binding was determined by directly counting in a gamma counter.

Data Analysis

The ligand binding data were analyzed by means of nonlinear regression using Prism version 5 (GraphPad Software, Inc., La Jolla, CA). The $K_i$ values were calculated from the experimental $IC_{50}$ values using the Cheng-Prusoff equation for a single population of competitive sites: $K_i=IC_{50}/[1+(L/K_d)]$, where L is the concentration of radioligand used in each experiment and the $K_d$ values were determined by saturation binding experiment. All of the assays were performed in duplicate and repeated at least two-three times.

TABLE 1

| | | | | | Ratio | | Human |
|---|---|---|---|---|---|---|---|
| CODE | COMPOUND | Mw | α4β2 nM | α3β4 nM | α3β4/ α4β2 | Rat α7 (Ki) nM | α7 K(i) nM |
| | Cytisine | 190.24 | 1.27 0.89-1.8 | 103 70.2-152 | 81.1 | 661.7 363/1206 nM | 690.7 362-1318 nM |
| | Nicotine | 162.23 | 8.6 4.8-15.6 | 172 109-274 | 20.0 | | |
| 68 | 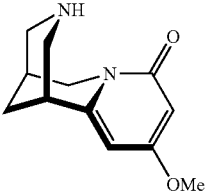 | 220.27 | 41 27.5-61.2 | 8452 4011-17810 | 206.1 | 21300 5347-84810 | |
| 70 | 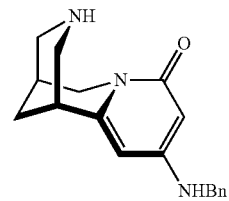 | 295.39 | 12.5 6.8-22.9 | 1563 832-2933 | 125.0 | 29000 8887-94320 | |

TABLE 1-continued
| | | | Binding Results | | | | |
|---|---|---|---|---|---|---|---|
| CODE | COMPOUND | Mw | α4β2 nM | α3β4 nM | Ratio α3β4/ α4β2 | Rat α7 (Ki) nM | Human α7 K(i) nM |
| 82 | 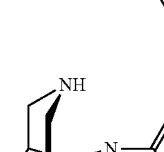 | 208.23 | 2.87 1.98-4.1 | 1921 1018-3626 | 699.3 | 9760 4689-20340 | |
| 60 | 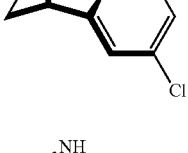 | 224.69 | 2.31 1.17-4.6 | 759 486-1186 | 328.6 | 223 94.04-527.5 | |
| 62 | 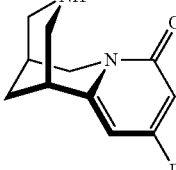 | 269.14 | 1.77 0.98-3.2 | 537 275-1049 | 303.4 | 323 69.02-1510 | |
| 73 | 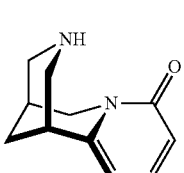 | 280.37 | 14.1 5.822-34.2 | 2280 759-6840 | 161.7 | 5630 2136-14830 | |
| 104 | 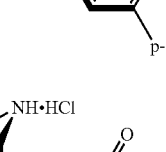 | 340.25 | 13.4 5.8-31.1 | 2260 1223-4182 | 168.7 | 11900 4432-31870 | |
| 101 | 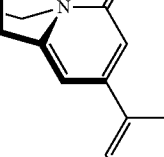 | 340.25 | 1.24 0.66-2.43 | 1953 1018-3746 | 1575.0 | 5780 3302-10130 | 4960 1956-12410 |

TABLE 1-continued

| | | | Binding Results | | | | |
|---|---|---|---|---|---|---|---|
| CODE | COMPOUND | Mw | α4β2 nM | α3β4 nM | Ratio α3β4/ α4β2 | Rat α7 (Ki) nM | Human α7 K(i) nM |
| 103 | (structure with pyridinone and pyridine·HCl) | 340.25 | 3.24 1.32-7.94 | 2785 1590-4881 | 859.6 | 3090 2161-4419 | |
| 92 | (structure with morpholine) | 311.81 | 18.5 8.74-39.4 | 1306 582-2928 | 70.6 | 7773 732.3-82500 (query?) | |
| 90 | (structure with piperazine·HCl) | 347.28 | 430 153-1209 | 6080 1116-33110 | 14.1 | 7879 2910-21330 | |
| 66 | (structure with OH) | 242.7 | 22.5 5.0-100.8 | 8951 4083-19620 | 397.8 | 12400 5329-28900 | |
| 81 | (structure with NH$_2$) | 278.18 | 6.36 5.37-20.4 | 9928 4005-24610 | 1561.0 | 9680 4992-13090 | 10270 5163-20420 |
| 84 | (structure with NHMe) | 292.2 | 10.8 5.37-20.4 | 27500 11170-66270 | 2546.3 | 15600 7638-32170 | 24550 5634-106900 (query) |

TABLE 1-continued
| | | | Binding Results | | | | |
|---|---|---|---|---|---|---|---|
| CODE | COMPOUND | Mw | α4β2 nM | α3β4 nM | Ratio α3β4/ α4β2 | Rat α7 (Ki) nM | Human α7 K(i) nM |
| 86 | 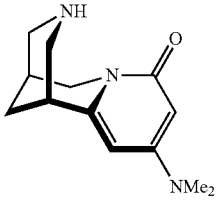 | 306.23 | 573 264-1245 | 3329 1769-6264 | 5.8 | 12400 6463-24050 | |
| 140 | 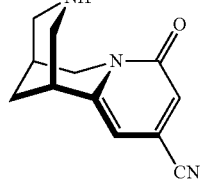 | 215.26 | 1.84 1.18-2.87 | 367 196-687 | 199.5 | 25600 9971-65750 | |
| 142 | 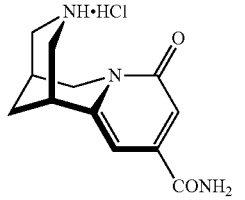 | 269.73 | 69 46.7-102.2 | 2497 739-8434 | 36.2 | 21900 9400-51230 | |
| 149 | 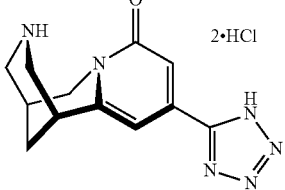 | 331.2 | 92.6 55.3-157 | 13820 2974-64230 | 149.2 | 10400 4684-23140 | |
| 77 | 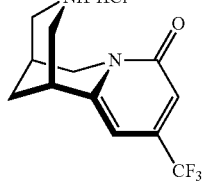 | 294.7 | 30.9 6.09-156 | 399 214-745 | 12.9 | 1820 762.5-4328 | |
| 119 | 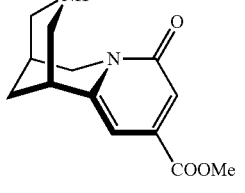 | 248.28 | 7.29 3.97-13.3 | 2672 1076-6631 | 366.5 | 77500 22320-268800 | |
| 120 | 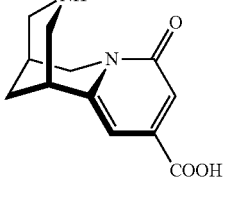 | 270.71 | 39.5 15.3-102.4 | 2281 691-7525 | 57.7 | 8890 3617-21860 | |

TABLE 1-continued

| | | | Binding Results | | | | |
|---|---|---|---|---|---|---|---|
| CODE | COMPOUND | Mw | α4β2 nM | α3β4 nM | Ratio α3β4/ α4β2 | Rat α7 (Ki) nM | Human α7 K(i) nM |
| 96 | *structure* | 345.83 | 11.9<br>3.64-39.4 | 1066<br>560-2028 | 89.6 | 5610<br>1391-22620 | |
| 94 | *structure* | 283.76 | 10.5<br>5.63-19.5 | 7886<br>2796-22240 | 751.0 | 14500<br>3731-57010 | |
| 144 | *structure* | 292.2 | 90.3<br>46-177.2 | 7046<br>2178-22800 | 78.0 | 1030<br>164.4-6456 | |
| 154 | *structure* | 256.73 | 3.5<br>2.28-5.38 | 26000<br>4031-167600 | 7428.0 | 8080<br>4992-13090 | 10600<br>1739-64410 |
| 79 | *structure* | 308.73 | 5.21<br>0.8-33.6 | 143<br>74.6-275 | 27.4 | 1040<br>314.2-3462 | |

TABLE 1-continued

Binding Results

| CODE | COMPOUND | Mw | α4β2 nM | α3β4 nM | Ratio α3β4/α4β2 | Rat α7 (Ki) nM | Human α7 K(i) nM |
|---|---|---|---|---|---|---|---|
| 127 | (bicyclic amine·HCl with pyridinone, ethynyl substituent) | 250.73 | 0.86<br>0.52-1.43 | 611<br>136-2733 | 710.5 | 8970<br>2302-34950 | |
| 114 | (bicyclic amine·HCl with pyridinone, styryl substituent, Ph) | 328.84 | 2.9<br>1.66-5.19 | 422<br>159-1124 | 145.5 | 5400<br>1577-18500 | |
| 112 | (bicyclic amine·HCl with pyridinone, CH=CH-CO$_2$Et substituent) | 324.81 | 8.1<br>4.8-13.5 | 1238<br>547-2801 | 152.8 | 3060<br>591.9-15780 | |
| 160 | (bicyclic amine·HCl with pyridinone, Br and I substituents) | 431.5 | 0.238<br>0.166-0.341 | 11.9<br>5-27.8 | 50.0 | | 26<br>19.4-35 |
| 162 | (bicyclic amine·HCl with pyridinone, CF$_3$ and Br substituents) | 373.6 | 0.88<br>0.69-1.18 | 120<br>43.8-328 | 136.4 | 5450<br>1676-17740 | |
| 74 | (bicyclic amine with pyridinone, pentafluorophenyl substituent) | 356.3 | 19.1<br>7.57-48.4 | 154<br>89-268 | 8.1 | 10890<br>1919-61830 | |

TABLE 1-continued

| | | | | | Ratio | | Human |
| | | | α4β2 | α3β4 | α3β4/ | Rat α7 (Ki) | α7 K(i) |
| CODE | COMPOUND | Mw | nM | nM | α4β2 | nM | nM |
|---|---|---|---|---|---|---|---|
| 116 | (structure) | 252.74 | 14.2<br>6.9-29.5 | 1422<br>419-4820 | 100.1 | | 40600<br>10090-163800 |
| 118 | (structure) | 254.76 | 3.01<br>2.06-4.39 | 5723<br>2403-13630 | 1901.3 | | 6928<br>2276-21080 |
| 137 | (structure) | 353.85 | No data | | | | |
| 138 | (structure) | 339.82 | 671.8<br>194-2326 | 1785<br>472-6746 | 2.7 | | 39810<br>12990-122000 |
| 129 | (structure) | 326.82 | 2.94<br>1.67-5.81 | 95<br>45-198 | 32.2 | | 3946<br>1856-8389 |
| 110 | (structure) | 240.73 | 2.63<br>1.59-4.36 | 2273<br>536-9633 | 864.3 | | 5027<br>1071-23590 |

TABLE 1-continued
| | | | Binding Results | | | | |
|---|---|---|---|---|---|---|---|
| CODE | COMPOUND | Mw | α4β2 nM | α3β4 nM | Ratio α3β4/ α4β2 | Rat α7 (Ki) nM | Human α7 K(i) nM |
| 108 | 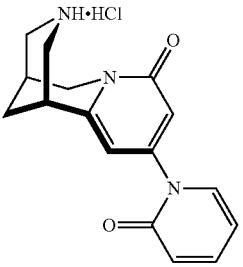 | 319.79 | 35.8 20.5-23.8 | 3233.00 1458-7171 | 90.3 | | 17080 1972-147900 |
| 98* | 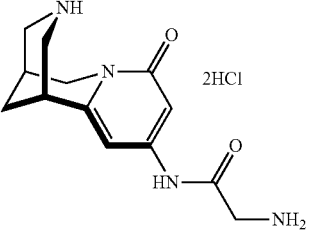 | 335.23 | 160 41.9-627 | 267200.00 13130-543700 | 1670.0 | | 54660 10480-285000 |
| 122 | 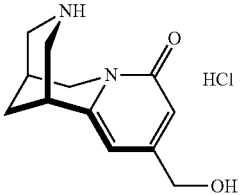 | 256.73 | 36.8 18-75 | 2685.00 864-8345 | 73.0 | | 116000 18400-731500 |
| ? | 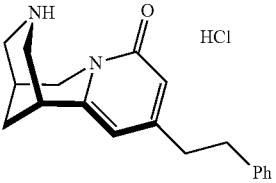 | 330.86 | 7.15 4.16-12.2 | 155.00 70.4-340 | 21.7 | | 22470 8590-58780 |
| 156 | 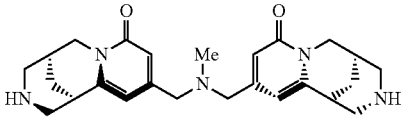 | 544.95 | 30.2 18.8-48.4 | 6278.00 1023-38510 | 207.9 | | 29270 6790-126200 |
| 151 | 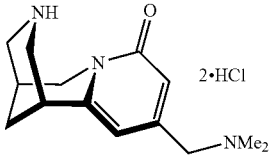 | 320.25 | 226 81.3-630 | 23890.00 6020-94800 | 105.7 | | 250900 5517-1141000 |
| 148 | 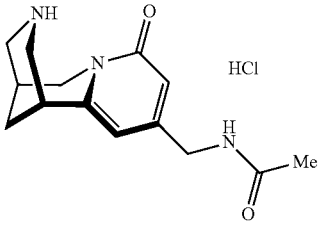 | 297.78 | 94.1 23.4-378 | 19270.00 6908-53760 | 204.8 | | 34150 5669-205700 |

TABLE 1-continued

Binding Results

| CODE | COMPOUND | Mw | α4β2 nM | α3β4 nM | Ratio α3β4/α4β2 | Rat α7 (Ki) nM | Human α7 K(i) nM |
|---|---|---|---|---|---|---|---|
| 87 | 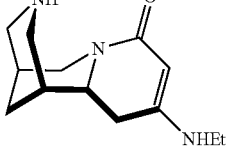 | 233.32 | 17.9<br>4.3-74.2 | 14950.00<br>7611-29370 | 835.2 | | 9804<br>1255-76600 |
| 152 | 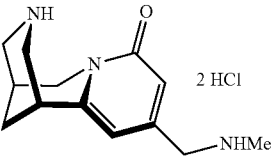 | 306.23 | 124.9<br>35.4-439 | 100800.00<br>14770-687400 | 807.0 | | 89600<br>19560-410500 |
| 124 | 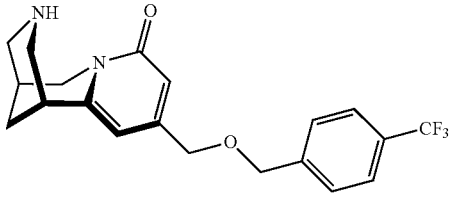 | 414.85 | 22.8<br>16.7-31.1 | 1402<br>322-6097 | 61.5 | | 56190<br>21780-144900 |
| 158 | 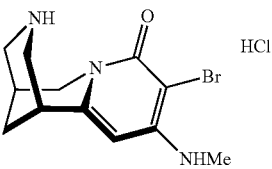 | 334.64 | 27.2<br>5.6-132 | 2908.00<br>973-8689 | 106.9 | | 6593<br>2235-19450 |

As can be seen from this data, the compounds of the present invention exhibit high selectivity at the human α4β2 receptor subtypes as compared to both α3β4 subtype and α7 (in both rat cells and human cells, where tested), minimising the likelihood of 'off-target' effects.

Example 71—Relative Efficacy at Nicotinic Receptor Subtypes

Compounds of the invention were tested for effects on the function of human α4β2, α3β4 and α7 nicotinic acetylcholine receptors (nAChRs) expressed heterologously in Xenopus oocytes. Human α4β2 nACh receptors were expressed as either $(α4)_3(β2)_2$ (low sensitivity for ACh) or $(α4)_2(β2)_3$ receptors (high sensitivity for ACh) (Moroni et al., 2006). Expression in oocytes was obtained as follows: pCI (Promega, UK) plasmid containing human α4, β2, β4 or α7 complementary DNA were injected as previously described (Moroni et al., 2006). To express $(α4)_3(β2)_2$ nACh receptors, a mixture of 10α4:1β2 cDNAs was injected into the nucleus of oocytes, whereas for $(α4)_2(β2)_3$ receptors the cDNA ratio injected was 1α4:10β2.

Functional studies: Recordings were performed manually using a Geneclamp amplifier (Molecular Devices, USA) or using an automated HiClamp system. In both cases the oocytes were impaled with two electrodes filled with 3 M KCl and the cells were held at −60 mV throughout the experiments.

Oocyte isolation and two-electrode voltage-clamp recordings on oocytes were carried out as previously described (Moroni et al., 2006; Carbone et al., 2009). Concentration-response curves for agonists were obtained by normalizing the compounds-induced responses to the responses elicited by 1 mM ACh, a concentration of ACh that maximally activates all the receptors tested (Abin-Carriquiry et al., 2006; Moroni et al., 2006; Carbone et al., 2009). A minimum interval of 5 min was allowed between agonist applications to ensure reproducible recordings. Oocytes were exposed to increasing concentrations of the compounds until no further increases in the response amplitude were obtained. This concentration was taken as the concentration that causes maximal responses on the receptors tested. The data summarised in Tables 1-4 were obtained from at least 5 experiments carried out on oocytes obtained from at least three different donors.

a) Effects of Compounds on $(α4)_3(β2)_2$ nAChRs (Low Sensitivity Stoichiometry)

Maximal gating efficacy of the compounds: The concentration of the compounds of the invention causing maximal activation of the $(α4)_3(β2)_2$ nAChRs expressed heterologously in Xenopus oocytes was determined using two electrode voltage clamping. The maximal currents elicited by the compounds was relativized to the maximal concentration elicited by 1 mM ACh (which induces maximal responses for $(α4)_3(β2)_2$ receptors.

TABLE 2

| Compound | Relative efficacy (ACh) |
| --- | --- |
| ACh | 1 |
| Cytisine | 0.19 ± 0.07 |
| Varenicline | 0.40 ± 0.09 |
| Nicotine | 0.48 ± 0.3 |
| 69 | 0.071 ± 0.009 |
| 82 | 0.12 ± 0.02 |
| 60 | 0.110 ± 0.08 |
| 62 | 0.057 ± 0.007 |
| 73 | 0.017 ± 0.019 |
| 101 | 0.009 ± 0.008 |
| 103 | 0.023 ± 0.006 |
| 67 | 0.07 ± 0.009 |
| 81 | 0.007 ± 0.01061 |
| 84 | 0.048 ± 0.040 |
| 140 | 0.050 ± 0.027 |
| 119 | 0.021 ± 0.007 |
| 94 | 0.153 ± 0.006 |
| 154 | 0.013 ± 0.008 |
| 127 | 0.071 ± 0.009 |
| 162 | 0.072 ± 0.026 |
| 75 | 0.011 ± 0.010 |
| 118 | 0.036 ± 0.055 |
| 110 | 0.014 ± 0.007 |
| 122 | 0.058 ± 0.057 |
| 156 | 0.052 ± 0.007 |
| 148 | 0.041 ± 0.057 |
| 87 | 0.011 ± 0.001 |
| 152 | 0.031 ± 0.043 |
| 158 | 0.049 ± 0.012 |
| BS70 | 0.114 ± 0.113 |
| BS71 | 0.152 ± 0.1223 |
| BS74 | 0.126 ± 0.067 | b) Effects on $(\alpha 4)_2(\beta 2)_3$ nAChRS

Maximal gating efficacy of compounds on $(\alpha 4)_2(\beta 2)_3$ receptors (high sensitivity receptors): The concentration of the compounds causing maximal activation of the $(\alpha 4)_2(\beta 2)_3$ nAChRs expressed heterologously in Xenopus oocytes was determined using two electrode voltage clamping. The maximal current elicited by the compounds was then relativized to the maximal concentration elicited by 1 mM ACh (which induces maximal responses on $(\alpha 4)_2(\beta 2)_3$ receptors.

TABLE 3

| Compound | Relative efficacy (ACh) |
| --- | --- |
| ACh | 1.0 |
| Cytisine | 0.02 ± 0.001 |
| Varenicline | 0.14 ± 0.03 |
| Nicotine | 0.31 ± 0.07 |
| 69 | 0.009 ± 0.0008 |
| 82 | 0.01 ± 0.001 |
| 60 | 0.01 ± 0.007 |
| 62 | 0.009 ± 0.0001 |
| 73 | 0.030 ± 0.013 |
| 101 | 0.0001 ± 0.00008 |
| 103 | 0.0067 ± 0.0006 |
| 67 | 0.005 ± 0.0001 |
| 81 | 0.024 ± 0.034 |
| 84 | 0.042 ± 0.059 |
| 140 | 0.026 ± 0.036 |
| 119 | 0.0065 ± 0.0005 |
| 94 | 0.001 ± 0.0006 |
| 154 | 0.0001 ± 0.00001 |
| 127 | 0.009 ± 0.0009 |
| 162 | 0.042 ± 0.060 |
| 75 | 0.050 ± 0.071 |
| 118 | 0.062 ± 0.025 |
| 110 | 0.041 ± 0.004 |
| 122 | 0.025 ± 0.000 |
| 156 | No response |
| 148 | 0.015 ± 0.021 |

TABLE 3-continued

| Compound | Relative efficacy (ACh) |
| --- | --- |
| 87 | 0.023 ± 0.032 |
| 158 | 0.038 ± 0.054 |
| BS74 | 0.121 ± 0.171 | c) Effects of the Compounds on $\alpha 3\beta 4$ nAChRs

Maximal gating efficacy of the compounds on $\alpha 3\beta 4$ nAChRs: The concentration of the compounds causing maximal activation of $\alpha 3\beta 4$ nAChRs expressed heterologously in Xenopus oocytes was determined using two electrode voltage clamping. The maximal currents elicited by the compounds were then relativized to the maximal concentration elicited by 1 mM ACh (which induces maximal responses on $\alpha 3\beta 4$ receptors).

TABLE 4

| Compound | Relative efficacy (ACh) |
| --- | --- |
| ACh | 1.0 |
| Cytisine | 0.54 ± 0.01 |
| Varenicline | 0.51 ± 0.09 |
| Nicotine | 0.71 ± 0.07 |
| 69 | 0.044 ± 0.059 |
| 82 | 0.073 ± 0.06 |
| 60 | 0.133 ± 0.017 |
| 62 | 0.184 ± 0.046 |
| 73 | 0.076 ± 0.093 |
| 101 | 0.066 ± 0.056 |
| 103 | 0.016 ± 0.010 |
| 67 | 0.047 ± 0.036 |
| 81 | 0.0210 ± 0.008 |
| 84 | 0.0233 ± 0.005 |
| 140 | 0.172 ± 0.064 |
| 119 | 0.040 ± 0.049 |
| 94 | 0.055 ± 0.047 |
| 154 | 0.093 ± 0.091 |
| 127 | 0.165 ± 0.064 |
| 162 | 0.250 ± 0.077 |
| 75 | 0.120 ± 0.039 |
| 118 | 0.086 ± 0.106 |
| 110 | 0.0708 ± 0.059 |
| 122 | 0.015 ± 0.020 |
| 156 | 0.012 ± 0.007 |
| 148 | 0.034 ± 0.038 |
| 87 | 0.010 ± 0.009 |
| 158 | 0.057 ± 0.016 |
| BS70 | 0.108 ± 0.149 |
| BS71 | 0.632 ± 0.067 |
| BS74 | 1.75 ± 0.56 | d) Effects of the Compounds on $\alpha 7$ nAChRs

Relative efficacy of the compounds on $\alpha 7$ nAChRs: The amplitude of currents elicited by the compounds at 100 μM was measured and then relativized to the amplitudes of the responses to 1 mM ACh, the concentration of ACh that causes maximal activation of $\alpha 7$ nAChRs.

TABLE 5

| Compound | Relative efficacy (ACh) |
| --- | --- |
| ACh | 1.0 |
| Cytisine | 1 ± 0.0.08 |
| Varenicline | 0.96 ± 0.03 |
| Nicotine | 0.96 ± 0.1 |
| 69 | 0.061 ± 0.09 |
| 82 | 0.18 ± 0.04 |
| 60 | 0.38 ± 0.09 |
| 62 | 0.28 ± 0.01 |
| 73 | 0.0027 ± 0.0021 |
| 101 | 0.16 ± 0.03 |

TABLE 5-continued

| Compound | Relative efficacy (ACh) |
|---|---|
| 103 | 0.07 ± 0.009 |
| 67 | No response at 100 µM |
| 94 | 0.0001 ± 0.00001 |
| 154 | No response at 100 µM |
| 127 | 0.17 ± 0.03 |
| 75 | 0.0007 ± 0.0006 |
| 118 | 0.0057 ± 0.0028 |
| 110 | 0.0017 ± 0.0024 |
| 122 | 0.0067 ± 0.0015 |

The data in Table 5 show that the compounds of the invention exhibit lower relative efficacy on the α7 receptor compared to cytisine and varenicline.

We claim:

1. A process for preparing a 4-substituted cytisine analog of formula (I):

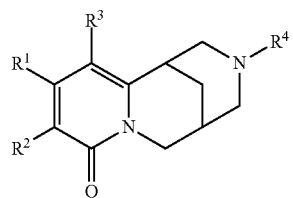

(I)

or a pharmaceutically acceptable salt, solvate and/or ester thereof, wherein:

$R^1$ is
hydroxyl;
halogen;
optionally substituted aliphatic;
optionally substituted cycloaliphatic;
optionally substituted heterocycloaliphatic;
optionally substituted aryl;
optionally substituted heteroaryl;
—$(CH_2)_m$—$NR^6R^7R^8$, wherein
$R^6$ and $R^7$ are each independently selected from the group consisting of hydrogen, halo, hydroxy, oxo, amino, amido, nitro, cyano, alkoxy, N-alkyl amino, N,N-dialkyl amino, phospho, carbonyl, carboxy, sulfoxy, sulfinyl, sulfonyl, sulfanyl, sulfamide, sulfo, mercapto, carbamoyl, methyl pivalate, trimethylsilyl, urea, thiourea, optionally substituted aryl, optionally substituted heteroaryl, optionally substituted alkyl, optionally substituted cycloaliphatic, optionally substituted heterocycloaliphatic, optionally substituted heteroaryl, optionally substituted haloalkyl, optionally substituted aroyl, optionally substituted heteroaroyl, optionally substituted acyl, optionally substituted alkenyl, optionally substituted alkynyl, optionally substituted aralkyl, optionally substituted cycloalkyl, optionally substituted cycloalkenyl, optionally substituted heterocycloalkyl or optionally substituted heterocycloalkenyl or
one of $R^6$ or $R^7$ is —CO—$R^9$, and the other of $R^6$ or $R^7$ is as defined above,
$R^8$ is selected from the group consisting of hydrogen, halo, hydroxy, oxo, amino, amido, nitro, cyano, alkoxy, N-alkyl amino, N,N-dialkyl amino, phospho, carbonyl, carboxy, sulfoxy, sulfinyl, sulfonyl, sulfanyl, sulfamide, sulfo, mercapto, carbamoyl, methyl pivalate, trimethylsilyl, urea, thiourea, optionally substituted aryl, optionally substituted heteroaryl, optionally substituted alkyl, optionally substituted cycloaliphatic, optionally substituted heterocycloaliphatic, optionally substituted heteroaryl, optionally substituted haloalkyl, optionally substituted aroyl, optionally substituted heteroaroyl, optionally substituted acyl, optionally substituted alkenyl, optionally substituted alkynyl, optionally substituted aralkyl, optionally substituted cycloalkyl, optionally substituted cycloalkenyl, optionally substituted heterocycloalkyl or optionally substituted heterocycloalkenyl, or is absent,
$R^9$ is selected from the group consisting of hydrogen, halo, hydroxy, oxo, amino, amido, nitro, cyano, alkoxy, N-alkyl amino, N,N-dialkyl amino, phospho, carbonyl, carboxy, sulfoxy, sulfinyl, sulfonyl, sulfanyl, sulfamide, sulfo, mercapto, carbamoyl, methyl pivalate, trimethylsilyl, urea, thiourea, optionally substituted aryl, optionally substituted heteroaryl, optionally substituted alkyl, optionally substituted cycloaliphatic, optionally substituted heterocycloaliphatic, optionally substituted heteroaryl, optionally substituted haloalkyl, optionally substituted aroyl, optionally substituted heteroaroyl, optionally substituted acyl, optionally substituted alkenyl, optionally substituted alkynyl, optionally substituted aralkyl, optionally substituted cycloalkyl, optionally substituted cycloalkenyl, optionally substituted heterocycloalkyl or optionally substituted heterocycloalkenyl,
and m is 0, 1, 2, 3, 4 or 5,
—$(CH_2)_m$—O—$(CH_2)_n$—$R^{10}$, wherein
$R^{10}$ is selected from the group consisting of hydrogen, halo, hydroxy, oxo, amino, amido, nitro, cyano, alkoxy, N-alkyl amino, N,N-dialkyl amino, phospho, carbonyl, carboxy, sulfoxy, sulfinyl, sulfonyl, sulfanyl, sulfamide, sulfo, mercapto, carbamoyl, methyl pivalate, trimethylsilyl, urea, thiourea, optionally substituted aryl, optionally substituted heteroaryl, optionally substituted alkyl, optionally substituted cycloaliphatic, optionally substituted heterocycloaliphatic, optionally substituted heteroaryl, optionally substituted haloalkyl, optionally substituted aroyl, optionally substituted heteroaroyl, optionally substituted acyl, optionally substituted alkenyl, optionally substituted alkynyl, optionally substituted aralkyl, optionally substituted cycloalkyl, optionally substituted cycloalkenyl, optionally substituted heterocycloalkyl or optionally substituted heterocycloalkenyl, and
m and n are each independently 0, 1, 2, 3, 4 or 5,
—CN
—$COOR^{12}$, wherein $R^{12}$ is selected from the group consisting of hydrogen, halo, hydroxy, oxo, amino, amido, nitro, cyano, alkoxy, N-alkyl amino, N,N-dialkyl amino, phospho, carbonyl, carboxy, sulfoxy, sulfinyl, sulfonyl, sulfanyl, sulfamide, sulfo, mercapto, carbamoyl, methyl pivalate, trimethylsilyl, urea, thiourea, optionally substituted aryl, optionally substituted heteroaryl, optionally substituted alkyl, optionally substituted cycloaliphatic, optionally substituted heterocycloaliphatic, optionally substituted heteroaryl, optionally substituted haloalkyl, optionally substituted aroyl, optionally substituted heteroaroyl, optionally substituted acyl, optionally substituted alkenyl, optionally substituted alkynyl, optionally substituted aralkyl, optionally substituted cycloalkyl, optionally substituted cycloalkenyl, optionally substituted heterocycloalkyl or optionally substituted heterocycloalkenyl, —(CH$_2$)$_o$—CO—(CH$_2$)$_p$—R$^{13}$, wherein R$^{13}$ is selected from the group consisting of hydrogen, halo, hydroxy, oxo, amino, amido, nitro, cyano, alkoxy, N-alkyl amino, N,N-dialkyl amino, phospho, carbonyl, carboxy, sulfoxy, sulfinyl, sulfonyl, sulfanyl, sulfamide, sulfo, mercapto, carbamoyl, methyl pivalate, trimethylsilyl, urea, thiourea, optionally substituted aryl, optionally substituted heteroaryl, optionally substituted alkyl, optionally substituted cycloaliphatic, optionally substituted heterocycloaliphatic, optionally substituted heteroaryl, optionally substituted haloalkyl, optionally substituted aroyl, optionally substituted heteroaroyl, optionally substituted acyl, optionally substituted alkenyl, optionally substituted alkynyl, optionally substituted aralkyl, optionally substituted cycloalkyl, optionally substituted cycloalkenyl, optionally substituted heterocycloalkyl or optionally substituted heterocycloalkenyl, and o and p are each independently 0, 1, 2, 3, 4 or 5, an amino acid or ester thereof, acyl chloride, a protecting group, or cytisinyl, R$^2$, R$^3$ and R$^4$ are each independently selected from the group consisting hydrogen, halo, hydroxy, oxo, amino, amido, nitro, cyano, alkoxy, N-alkyl amino, N,N-dialkyl amino, phospho, carbonyl, carboxy, sulfoxy, sulfinyl, sulfonyl, sulfanyl, sulfamide, sulfo, mercapto, carbamoyl, methyl pivalate, trimethylsilyl, urea, thiourea, optionally substituted aryl, optionally substituted heteroaryl, optionally substituted alkyl, optionally substituted cycloaliphatic, optionally substituted heterocycloaliphatic, optionally substituted heteroaryl, optionally substituted haloalkyl, optionally substituted aroyl, optionally substituted heteroaroyl, optionally substituted acyl, optionally substituted alkenyl, optionally substituted alkynyl, optionally substituted aralkyl, optionally substituted cycloalkyl, optionally substituted cycloalkenyl, optionally substituted heterocycloalkyl or optionally substituted heterocycloalkenyl, amino acid or cytisine, or R$^4$ is a protecting group, or a group having the structure —(CH$_2$)v-FORMULA 1, wherein v is 0, 1, 2, 3, 4, 5 or 6 and FORMULA 1 is a compound of Formula (I), the process comprising:

i) providing a compound of Formula IIa

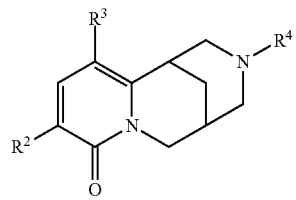

wherein R$^2$, R$^3$ and R$^4$ are as defined above;

ii) producing a compound of Formula IIb

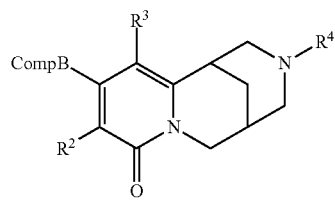

wherein R$^2$, R$^3$ and R$^4$ are as defined above, and BComp is a borylated complex, by contacting the compound of Formula IIa with a borylating agent;

iii) replacing BComp with R$^1$ to produce a compound of Formula I:

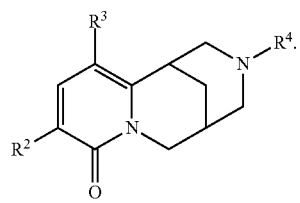

2. The process of claim 1, wherein when the compound of Formula IIa provided in step i) comprises a hydrogen atom at the R$^4$ position, that step further comprising the substitution of the hydrogen atom at the R$^4$ position with a protecting group.

3. The process of claim 2, wherein the protecting group is Boc.

4. The process of claim 2, wherein the compound of Formula IIa is cytisine.

5. The process of any one of claim 1, wherein the borylating agent is selected from:
   one having the formula (RO)$_2$—B—B—(OR)$_2$ or HB(OR)$_2$; and
   B$_2$Pin$_2$ or B$_2$Cat2.

6. The process of claim 1, wherein the molar ratio of borylating agent:starting material of Formula IIa is at least about 0.5:1, at least about 0.75:1, at least about 1:1, at least about 1.5:1 or at least about 2:1.

7. The process of claim 1, wherein the reaction in step ii) is carried out in the presence of a transition metal catalyst comprising iridium, palladium, zinc, nickel and/or rhodium.

8. The process of claim 1, wherein the reaction in step ii) is carried out in a solvent selected from an ester solvent, an ether solvent, a ketone solvent, a sulfoxide solvent, an aromatic solvent, a fluorinated aromatic solvent, an alkane solvent or mixtures thereof.

9. The process of claim 1, wherein step ii) is carried out in the presence of a ligand selected from:
tetramethyl-1,10-phenanthroline (Me₄phen), di-tert-butyl-2,2'-bipyridyl (dtbpy), 2,2'-bipyridine (bpy), 1,1'-bis(diphenylphosphino)ferrocene (dppf), bis(2-di-tert-butylphosphinophenyl)ether, 1,3-bis(diphenylphosphino)propane, (dppp) 1,2-bis(diphenylphosphino)ethane (dppe), hexamethylbenzene (C6Me₆), xantphos or 1,2-bis(dimethylphosphino)ethane (dmpe); and
phenanthroline (phen), dimethylphenanthroline (me2phen) tetramethyl-1,10-phenanthroline (me4phen), bathophenanthroline (bathophen), di-tert-butyl-2,2'-bipyridyl (dtbpy), 2,2'-bipyridine (bpy), dimethoxy-2,2'-bipyridyl (MeO-bpy), 1,1'-bis(diphenylphosphino)ferrocene (dppf), bis(2-di-tert-butylphosphinophenyl)ether, 1,3-bis(diphenylphosphino)propane (dppp), 1,2-bis(diphenylphosphino)ethane (dppe), hexamethylbenzene (C6Me₆), neocuproine, xantphos, 1,2-is(dimethylphosphino)ethane (dmpe), or one of

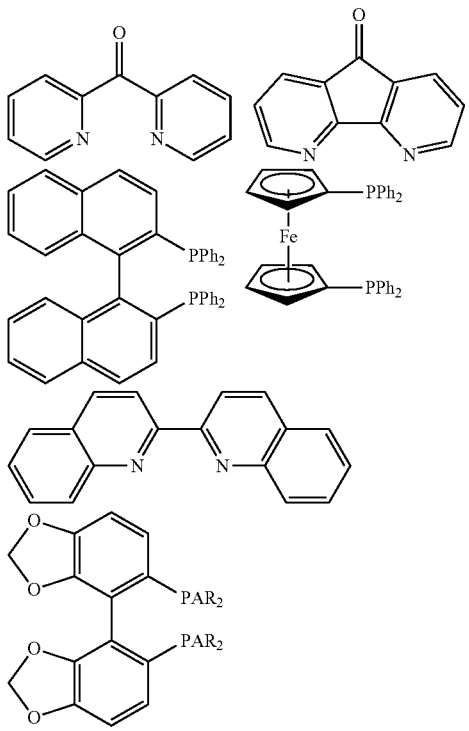

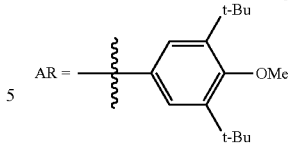

10. The process of claim 9, wherein the molar ratio of the ligand:starting material of Formula IIa is less than about 2:1, less than about 1.5:1, less than about 1:1, less than about 0.75:1, less than about 0.5:1, less than about 0.1:1, less than about 0.05:1 to at least about 0.001:1.

11. The process of claim 1, wherein the borylation in step ii) is carried out at a temperature of about 50° C. to about 100° C.

12. The process of claim 1, wherein prior to the commencement of step iii) the compound of Formula IIb is not isolated from the product mixture formed in step ii) and/or no purification step is carried out between steps ii) and iii).

13. The process of claim 1, wherein step iii) is commenced in the same reaction zone in which step ii) was carried out.

14. The process of claim 1, wherein, in step iii) BComp is replaced with a first intermediate $R^1$ substituent.

15. The process of claim 14, wherein the first intermediate substituent is replaced with a second intermediate $R^1$ substituent, or with a substituent $R^1$ to provide the compound of Formula I;
or the first intermediate substituent is replaced with a second intermediate $R^1$ substituent and the second intermediate substituent is replaced with a third intermediate $R^1$ substituent, or with a substituent $R^1$ to provide the compound of Formula I.

16. The process of claim 15, wherein the first, second and third intermediate $R^1$ substituents are independently selected from bromo, chloro, iodo, benzyloxypyridine, alkyl ester, methyl ester, alkenyl, vinyl, alkynyl, acetylenyl, trimethylsilylacetylene, 1,2,3-triazol-1-ylmethyl pivalate, cyano, aminomethyl, N-Boc-aminomethyl and (benzyloxy)carbonyl)piperazin-1-yl.

17. The process of claim 1, wherein the compound of Formula IIb or Formula I comprises a protecting group at the $R^4$ position, the process further comprising deprotecting the $R^4$ group of the compound of Formula IIb or Formula I and the deprotection of the $R^4$ group of the compound of Formula IIb or Formula I takes place after the completion of step ii), before the commencement of step iii), during step iii) or after the completion of step iii).

* * * * *